(12) United States Patent
Marliere

(10) Patent No.: US 9,169,496 B2
(45) Date of Patent: Oct. 27, 2015

(54) METHOD FOR THE ENZYMATIC PRODUCTION OF BUTADIENE

(71) Applicant: Scientist of Fortune, S.A., Luxembourg (LU)

(72) Inventor: Philippe Marliere, Mouscron (BE)

(73) Assignee: Scientist of Fortune, S.A., Luxembourg (LU)

( * ) Notice: Subject to any disclaimer, the term of this patent is extended or adjusted under 35 U.S.C. 154(b) by 0 days.

(21) Appl. No.: 14/352,825

(22) PCT Filed: Oct. 18, 2012

(86) PCT No.: PCT/EP2012/070661
§ 371 (c)(1),
(2) Date: Apr. 18, 2014

(87) PCT Pub. No.: WO2013/057194
PCT Pub. Date: Apr. 25, 2013

(65) Prior Publication Data
US 2014/0256009 A1    Sep. 11, 2014

Related U.S. Application Data

(60) Provisional application No. 61/549,149, filed on Oct. 19, 2011.

(30) Foreign Application Priority Data

Oct. 19, 2011    (EP) ...................................... 11185854

(51) Int. Cl.
*C12P 5/02*    (2006.01)
*C12P 7/04*    (2006.01)
(Continued)

(52) U.S. Cl.
CPC ............... *C12P 5/026* (2013.01); *C12N 9/1205* (2013.01); *C12N 9/1235* (2013.01); *C12N 9/88* (2013.01); *C12P 7/04* (2013.01); *C12P 7/24* (2013.01)

(58) Field of Classification Search
None
See application file for complete search history.

(56) References Cited

U.S. PATENT DOCUMENTS

| 5,855,881 A | * | 1/1999 | Loike et al. | ................... 424/94.2 |
| 2011/0300597 A1 | * | 12/2011 | Burk et al. | ..................... 435/167 |

FOREIGN PATENT DOCUMENTS

| WO | 2009111513 A1 | 9/2009 |
| WO | 2011140171 A | 11/2011 |

(Continued)

OTHER PUBLICATIONS

EC 1.1.1.34 (last viewed on Mar. 30, 2015).*

(Continued)

*Primary Examiner* — Alexander Kim
(74) *Attorney, Agent, or Firm* — Michael M. Wales; InHouse Patent Counsel, LLC

(57) ABSTRACT

Described is a method for the enzymatic production of butadiene which allows to produce butadiene from crotyl alcohol. Also described are enzyme combinations and compositions containing such enzyme combinations which allow the enzymatic conversion of crotyl alcohol into butadiene. Furthermore, the invention relates to microorganisms which have been genetically modified so as to be able to produce butadiene from crotyl alcohol.
Moreover, the invention relates to a method for the enzymatic production of crotyl alcohol from crotonyl-Coenzyme A. The obtained crotyl alcohol can be further converted into butadiene as described herein. Also described are enzyme combinations which allow to convert crotonyl-Coenzyme A into crotyl alcohol as well as (micro)organisms which express such enzyme combinations.

32 Claims, 10 Drawing Sheets

Figure 1:
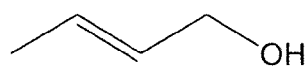

(51) Int. Cl.
*C12P 7/24* (2006.01)
*C12N 9/12* (2006.01)
*C12N 9/88* (2006.01)

(56) References Cited

FOREIGN PATENT DOCUMENTS

| WO | 2012081723 A1 | 6/2012 |
| WO | 2012106516 A1 | 8/2012 |
| WO | 2012177710 A1 | 12/2012 |

OTHER PUBLICATIONS

EC 1.1.1.1. (last viewed on Mar. 30, 2015).*
EC 1.2.1.n2 (last viewed on Mar. 30, 2015).*
Q08891-FACR2__ARATH (last viewed on Mar. 30, 2015).*
Q96533-ADHX__ARATH (last viewed on Mar. 30, 2015).*
Q9SAH9-CCR2__ARATH (last viewed on Mar. 30, 2015).*
Q60352-IPK__METJA (last viewed on Mar. 30, 2015).*
Q58270-IDSA__METJA (last viewed on Mar. 30, 2015).*
Q60337-THIL__METJA (last viewed on Mar. 30, 2015).*
Lin et al., Characterization of the monoterpene synthase gene tps26, the ortholog of a gene induced by insect herbivory in maize., Plant Physiol. (2008), vol. 146(3), pp. 940-951.*

Osterman et al., Characterization of mutation-induced changes in the maize (*Zea mays* L.) ADH1-1S1108 alcohol dehydrogenase, Journal Biochem. Genet. (1993), vol. 31 (11-12), pp. 497-506. Copy provided with the Abstract only.*
XP__008660506.1 (last viewed on Mar. 31, 2015).*
International Preliminary Examination Report (IPER) for PCT/EP2012/070661 mailed on May 1, 2014.
Database CAPLUS [Online] Chemical Abstracts Service; 1958, Gorin, Y.A. et al.: "Diene hydrocarbons from unsaturated alcohols. I. Catalytic dehydration of crotyl alcohol to butadiene", XP002673746, Database accession No. 1958:72071.
Database WPI Week 198927 Thomson Scientific, London, GB; AN 1989-195596 XP002673747, & JP 1 132391 A (Showa Denko KK) May 24, 1989.
Database WPI Week 201244 Thomson Scientific, London, GB; AN 2012-H02951 XP002694246, & WO 2012/081723 A1 (Mitsubishi Chem Corp) Jun. 21, 2012.
Havel, C. AL., Isopentenoid synthesis in isolated embryonic *Drosophila* cells. Possible regulation of 3-hydroxy-3-methylglutaryl coenzyme A reductase activity by shunted mevalonate carbon, Journal of Biological Chemistry, Aug. 5, 1986, pp. 10150-10156, vol. 261, No. 22, XP008160854.

* cited by examiner

METHOD FOR THE ENZYMATIC PRODUCTION OF BUTADIENE

This Application is a 371 National Phase filing of EP 2012070661 filed Oct. 18, 2012, which is a continuation of EP 11 858 544 which was filed on Oct. 19, 2011 and a nonprovisional of U.S Ser. No. 61/545,149 filed Oct. 19, 2011, which are all incorporated by reference in their entirety.

The present invention relates to a method for the enzymatic production of butadiene which allows to produce butadiene from crotyl alcohol. The present invention also relates to microorganisms which have been genetically modified so as to produce butadiene.

The present invention also relates to a method for the enzymatic production of crotyl alcohol from crotonyl-Coenzyme A. The obtained crotyl alcohol can be further converted into butadiene as described herein. The present invention furthermore relates to enzyme combinations which allow to convert crotonyl-Coenzyme A into crotyl alcohol as well as to (micro)organisms which express such enzyme combinations.

Figure 4:
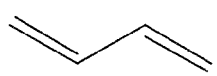

Butadiene (1,3-butadiene) is a conjugated diene with the formula $C_4H_6$ (see FIG. 4). It is an important industrial chemical used as a monomer in the production of synthetic rubber. There exist different possibilities to produce butadiene. Butadiene is, for example, produced as a by product of the steam cracking process used to produce ethylene and other olefins. In this process butadiene occurs in the C4 stream and is normally isolated from other byproducts by extraction into a polar aprotic solvent, such as acetonitrile, from which it is then stripped. Butadiene can also be produced by the catalytic dehydrogenation of normal butane or it can be produced from ethanol. In the latter case, two different processes are in use. In a single-step process, ethanol is converted to butadiene, hydrogen and water at 400-450° C. over a metal oxide catalyst (Kirshenbaum, I. (1978), Butadiene. In M. Grayson (Ed.), *Encyclopedia of Chemical Technology*, 3rd ed., vol. 4, pp. 313-337. New York: John Wiley & Sons). In a two-step process, ethanol is oxidized to acetaldehyde which reacts with additional ethanol over a tantalum-promoted porous silica catalyst at 325-350° C. to yield butadiene (Kirshenbaum, I. (1978), loc cit.). Butadiene can also be produced by catalytic dehydrogenation of normal butenes.

For the past two decades, genetic engineering technologies have made possible the modification of the metabolism of micro-organisms, and hence their use to produce key substances which they would otherwise produce at a low yield. By enhancing naturally occurring metabolic pathways, these technologies open up new ways to bio-produce numerous compounds of industrial relevance. Several industrial compounds such as amino-acids for animal feed, biodegradable plastics or textile fibres are now routinely produced using genetically modified organisms. There are however no bioprocesses using micro-organisms in place for the production of the major petrochemically derived molecules, in particular butadiene, since no micro-organisms are known as natural producers of butadiene even in small quantities. Given the large amounts of rubber produced worldwide and the increasing environmental concerns and the limited resources for producing butadiene using chemical processes, there is a need to provide alternative, environmentally-friendly and sustainable processes for the production of butadiene.

The present invention addresses this need and provides for the first time a process by which butadiene can be produced enzymatically starting from crotyl alcohol. Crotyl alcohol itself can be provided by the enzymatic conversion of crotonyl CoA which, in turn, can be provided starting from the metabolic intermediate acetyl-Coenzyme A (in the following acetyl-CoA) as described herein.

Thus, in a first aspect, the present invention relates to a process for the production of butadiene in which butadiene is produced by the enzymatic conversion of crotyl alcohol. Crotyl alcohol, also referred to as crotonyl alcohol or crotonol, is an unsaturated alcohol of formula $C_4H_8O$ (see FIG. 1). Another name for crotyl alcohol is But-2-en-1-ol. It can be produced by reduction of crotonaldehyde (see FIG. 3). According to the present invention crotyl alcohol can be converted into butadiene by enzymatic reactions involving as intermediates crotyl phosphate and/or crotyl diphosphate. Thus, the principle underlying the present invention is that crotyl alcohol is first enzymatically activated by the conversion into crotyl phosphate or crotyl diphosphate and is then further converted into butadiene by the use of appropriate enzymes as described below.

Thus, the present invention relates, in a first aspect, to a method for the production of butadiene comprising the enzymatic conversion of crotyl alcohol into butadiene via crotyl phosphate or crotyl diphosphate.

The enzymatic conversion of crotyl alcohol into butadiene can occur via different alternative routes. In a first aspect (A), the present invention relates to a method for the production of butadiene comprising the enzymatic conversion of crotyl alcohol into butadiene via crotyl phosphate wherein said method comprises the steps of (i) enzymatically converting crotyl alcohol into crotyl phosphate; and
(ii) enzymatically converting crotyl phosphate into butadiene.

This alternative is in the following referred to as Alternative A and the different steps are referred to as A(i) and A(ii).

As regards step A(i), the enzymatic conversion of crotyl alcohol into crotyl phosphate is a phosphorylation step and can be achieved by enzymes which catalyze the transfer of a phospho group onto a molecule, such as kinases. For example, enzymes which can be employed in this reaction are enzymes which are classified as E.C. 2.7.1, i.e. phosphotransferases with an alcohol group as acceptor, preferably enzymes which are classified as 2.7.1.50 (hydroxyethylthiazole kinase) or which are classified as E.C. 2.7.1.89 (thiamine kinase). Preferably, ATP is the donor of the phospho group in such a reaction. Thus, in one embodiment the enzymatic conversion of crotyl alcohol into crotyl phosphate can, e.g., be achieved by the use of a hydroxyethylthiazole kinase (EC 2.7.1.50). Hydroxyethylthiazole kinase is an enzyme which catalyzes the following reaction

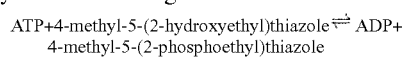
ATP+4-methyl-5-(2-hydroxyethyl)thiazole ⇌ ADP+ 4-methyl-5-(2-phosphoethyl)thiazole The occurrence of this enzyme has been described for several organisms, e.g. for *E. coli, Bacillus subtilis, Rhizobium leguminosarum, Pyrococcus horikoshii* OT3, *Saccharomyces cerevisiae*.

In another embodiment the enzymatic conversion of crotyl alcohol into crotyl phosphate can, e.g., be achieved by the use of a thiamine kinase (EC 2.7.1.89). Thiamine kinase is an enzyme which catalyzes the following reaction

ATP+thiamine ⇌ ADP+thiamine phosphate

The occurrence of this enzyme has been described for several organisms, e.g. for *E. coli* and *Salmonella enterica*.

Hydroxyethylthiazole is a moiety of thiamine and shares with crotyl alcohol the following common structural motif CH—C—CH—$CH_2$—OH.

Thus, the inventor considers that a hydroxyethylthiazole kinase or a thiamine kinase could also act on other substrates which contain this motif and found that, indeed, different tested hydroxyethylthiazole kinases and thiamine kinases were capable of using crotyl alcohol as a substrate and converting it into crotyl phosphate In principle, any known hydroxyethylthiazole kinase can be employed in the method according to the invention. In one aspect of the present invention, a hydroxyethylthiazole kinase of bacterial origin is used, such as a hydroxyethylthiazole kinase from a bacterium belonging to the genus *Escherichia*, *Bacillus* or *Rhizobium*, preferably of *E. coli*, *Bacillus subtilis* or of *R. leguminosarum*. Amino acid and nucleotide sequences for these enzymes are available. Examples for corresponding amino acid sequences are provided in SEQ ID NOs: 1 to 3. In a particularly preferred embodiment any protein showing an amino acid sequence as shown in any one of SEQ ID NOs: 1 to 3 or showing an amino acid sequence which is at least 80% homologous to any of SEQ ID NOs: 1 to 3 and having the activity of a hydroxyethylthiazole kinase can be employed in a method according to the present invention.

Moreover, in principle, any known thiamine kinase can be employed in the method according to the invention. In one aspect of the present invention, a thiamine kinase of bacterial origin is used, such as a thiamine kinase from a bacterium belonging to the genus *Escherichia* or *Salmonella*, preferably of *E. coli* or of *Salmonella enterica*. Amino acid and nucleotide sequences for these enzymes are available.

In one embodiment of this method, step A(ii) consists of a single enzymatic reaction in which crotyl phosphate is directly converted into butadiene. This option is in the following referred to as option A(ii1). In this conversion of crotyl phosphate into butadiene the phospho group is removed from crotyl phosphate with the simultaneous production of butadiene. An enzyme which can catalyze this reaction is referred to as a crotyl phosphate phosphate-lyase (butadiene forming). Examples of enzymes which can catalyze the dephosphorylation of crotyl phosphate into butadiene are enzymes which can be classified as belonging to the terpene synthase family. Preferably such an enzyme belongs to the family of plant terpene synthases. The terpene synthases constitute an enzyme family which comprises enzymes catalyzing the formation of numerous natural products always composed of carbon and hydrogen (terpenes) and sometimes also of oxygen or other elements (terpenoids). Terpenoids are structurally diverse and widely distributed molecules corresponding to well over 30000 defined natural compounds that have been identified from all kingdoms of life. In plants, the members of the terpene synthase family are responsible for the synthesis of the various terpene molecules from two isomeric 5-carbon precursor "building blocks", isoprenyl diphosphate and prenyl diphosphate, leading to 5-carbon isoprene, 10-carbon monoterpene, 15-carbon sesquiterpene and 20-carbon diterpenes" (Chen et al.; The Plant Journal 66 (2011), 212-229).

The ability of terpene synthases to convert a prenyl diphosphate containing substrate to diverse products during different reaction cycles is one of the most unique traits of this enzyme class. The common key step for the biosynthesis of all terpenes is the reaction of terpene synthase on corresponding diphosphate esters. The general mechanism of this enzyme class induces the removal of the diphosphate group and the generation of an intermediate with carbocation as the first step. In the various terpene synthases, such intermediates further rearrange to generate the high number of terpene skeletons observed in nature. In particular, the resulting cationic intermediate undergoes a series of cyclizations, hydride shifts or other rearrangements until the reaction is terminated by proton loss or the addition of a nucleophile, in particular water for forming terpenoid alcohols (Degenhardt et al., Phytochemistry 70 (2009), 1621-1637).

The different terpene synthases share various structural features. These include a highly conserved C-terminal domain, which contains their catalytic site and an aspartate-rich DDXXD (SEQ ID NO: 19)motif essential for the divalent metal ion (typically Mg2+ or Mn2+) assisted substrate binding in these enzymes (Green et al. Journal of biological chemistry, 284, 13, 8661-8669). In principle, any known enzyme which can be classified as belonging to the EC 4.2.3 enzyme superfamily can be employed for the conversion of crotyl phosphate into butadiene.

Even more preferably the method according to the invention makes use of an isoprene synthase (EC 4.2.3.27), a myrcene/ocimene synthase (EC 4.2.3.15), a farnesene synthase (EC 4.2.3.46 or EC 4.2.3.47) or a pinene synthase (EC 4.2.3.14). Also enzymes which are generally classified as monoterpene synthases can be used.

In a particularly preferred embodiment, the dephosphorylation of crotyl phosphate to butadiene is achieved by an isoprene synthase (EC 4.2.3.27). Isoprene synthase is an enzyme which catalyzes the following reaction:

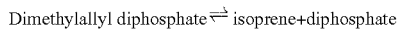

Dimethylallyl diphosphate ⇌ isoprene+diphosphate

This enzyme occurs in a number of organisms, in particular in plants and some bacteria. The occurrence of this enzyme has, e.g., been described for *Arabidopsis thaliana*, a number of *Populus* species like *P. alba* (UniProt accession numbers Q50L36, A9Q7C9, D8UY75 and D8UY76), *P. nigra* (UniProt accession number A0PFK2), *P. canescence* (UniProt accession number Q9AR86; see also Köksal et al., J. Mol. Biol. 402 (2010), *P. tremuloides, P. trichocarpa, P. lobata*, in *Quercus petraea, Quercus robur, Salix discolour, Pueraria montana* (UniProt accession number Q6EJ97), *Mucuna pruriens, Vitis vinifera, Embryophyta* and *Bacillus subtilis*. In principle, any known isoprene synthase can be employed in the method according to the invention. In a preferred embodiment, the isoprene synthase employed in a method according to the present invention is an isoprene synthase from a plant of the genus *Populus*, more preferably from *Populus trichocarpa* or *Populus alba*. In another preferred embodiment the isoprene synthase employed in a method according to the present invention is an isoprene synthase from *Pueraria montana*, preferably from *Pueraria montana* var. *lobata* (an example for such a sequence is provided in SEQ ID NO: 7), or from *Vitis vinifera*. Preferred isoprene synthases to be used in the context of the present invention are the isoprene synthase of *Populus alba* (Sasaki et al.; FEBS Letters 579 (2005), 2514-2518) or the isoprene synthases from *Populus trichocarpa* and *Populus tremuloides* which show very high sequence homology to the isoprene synthase from *Populus alba*. A particularly preferred isoprene synthase is the isoprene synthase from *Pueraria montana* var. *lobata* (kudzu) (Sharkey et al.; Plant Physiol. 137 (2005), 700-712). In a particularly preferred embodiment a protein showing an amino acid sequence as shown in SEQ ID NOs: 7 or showing an amino acid sequence which is at least 80% homologous to SEQ ID NOs: 7 and having the activity of an isoprene synthase can be employed in a method according to the present invention.

The activity of an isoprene synthase can be measured according to methods known in the art, e.g. as described in Silver and Fall (Plant Physiol (1991) 97, 1588-1591). In a typical assay, the enzyme is incubated with dimethylallyl diphosphate in the presence of the required co-factors, $Mg^{2+}$ or $Mn^{2+}$ and K+ in sealed vials. At appropriate time volatiles compound in the headspace are collected with a gas-tight syringe and analyzed for isoprene production by gas chromatography (GC). Crotyl monophosphate and crotyl diphosphate are structurally closely related to dimethylallyl diphosphate. In particular, the difference between crotyl diphosphate and dimethylallyl diphosphate is just a methyl group (see FIG. 8). The inventor considers that, therefore, an isoprene synthase can also use crotyl diphosphate or crotyl monophosphate as a substrate. In principle, any known isoprene synthase can be employed in the method according to the invention.

In another particularly preferred embodiment, the enzyme used for the conversion of crotyl phosphate into butadiene is a myrcene/ocimene synthases (EC 4.2.3.15). Myrcene/ocimene synthases (EC 4.2.3.15) are enzymes which naturally catalyze the following reaction:

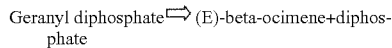
Geranyl diphosphate ⇒ (E)-beta-ocimene+diphosphate or

Geranyl diphosphate ⇒ myrcene+diphosphate

These enzymes occur in a number of organisms, in particular in plants and animals, for example in *Lotus japanicus*, *Phaseolus lunatus*, *Abies grandis*, *Arabidopsis thaliana* (UniProt accession number Q9ZUH4), *Actinidia chinensis*, *Perilla fructescens*, *Vitis vinifera*, *Ochtodes secundiramea* and in *Ips pini* (UniProt accession number Q58GE8. In principle, any known myrcene/ocimene synthase can be employed in the method according to the invention. In a preferred embodiment, the myrcene/ocimene synthase employed in a method according to the present invention is a beta-ocimene synthase from *Lotus japanicus* (Arimura et al.; Plant Physiol. 135 (2004), 1976-1983; an example for such an enzyme is provided in SEQ ID NO: 9) or from *Phaseolus lunatus* (UniProt accession number B1P189; an example for such an enzyme is provided in SEQ ID NO: 10). In a particularly preferred embodiment the myrcene/ocimene synthase is an (E)-beta-ocimene synthase from *Vitis vinifera* (an example for such an enzyme is provided in SEQ ID NO: 12). In a particularly preferred embodiment any protein showing an amino acid sequence as shown in any one of SEQ ID NOs: 9, 10 or 12 or showing an amino acid sequence which is at least 80% homologous to any of SEQ ID NOs: 9, 10 or 12 and having the activity of a beta-ocimene synthase can be employed in a method according to the present invention.

The activity of an ocimene/myrcene synthase can be measured as described, for example, in Arimura et al. (Plant Physiology 135 (2004), 1976-1983. In a typical assay for determining the activity, the enzyme is placed in screwcapped glass test tube containing divalent metal ions, e.g. $Mg^{2+}$ and/or $Mn^{2+}$, and substrate, i.e. geranyl diphosphate. The aqueous layer is overlaid with pentane to trap volatile compounds. After incubation, the assay mixture is extracted with pentane a second time, both pentane fractions are pooled, concentrated and analyzed by gas chromatography to quantify ocimene/myrcene production.

Beta-farnesene synthases (EC 4.2.3.47) naturally catalyze the following reaction:

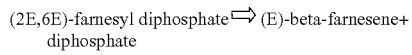
(2E,6E)-farnesyl diphosphate ⇒ (E)-beta-farnesene+diphosphate

This enzyme occurs in a number of organisms, in particular in plants and in bacteria, for example in *Artemisia annua* (UniProt accession number Q4VM12), *Citrus junos* (UniProt accession number Q94JS8), *Oryza sativa* (UniProt accession number Q0J7R9), *Pinus sylvestris* (UniProt accession number D7PCH9), *Zea diploperennis* (UniProt accession number C7E5V9), *Zea mays* (UniProt accession numbers Q2NM15, C7E5V8 and C7E5V7), *Zea perennis* (UniProt accession number C7E5W0) and *Streptococcus coelicolor* (Zhao et al., J. Biol. Chem. 284 (2009), 36711-36719). In principle, any known beta-farnesene synthase can be employed in the method according to the invention. In a preferred embodiment, the beta-farnesene synthase employed in a method according to the present invention is a beta-farnesene synthase from *Mentha piperita* (Crock et al.; Proc. Natl. Acad. Sci. USA 94 (1997), 12833-12838).

Methods for the determination of farnesene synthase activity are known in the art and are described, for example, in Green et al. (Phytochemistry 68 (2007), 176-188). In a typical assay farnesene synthase is added to an assay buffer containing 50 mM BisTrisPropane (BTP) (pH 7.5), 10% (v/v) glycerol, 5 mM DTT. Tritiated farnesyl diphosphate and metal ions are added. Assays containing the protein are overlaid with 0.5 ml pentane and incubated for 1 h at 30° C. with gentle shaking. Following addition of 20 mM EDTA (final concentration) to stop enzymatic activity an aliquot of the pentane is removed for scintillation analysis. The olefin products are also analyzed by GC-MS.

Pinene synthase (EC 4.2.3.14) is an enzyme which naturally catalyzes the following reaction:

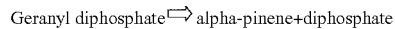
Geranyl diphosphate ⇒ alpha-pinene+diphosphate

This enzyme occurs in a number of organisms, in particular in plants, for example in *Abies grandis* (UniProt accession number O244475), *Artemisia annua*, *Chamaecyparis formosensis* (UniProt accession number C3RSF5), *Salvia officinalis* and *Picea sitchensis* (UniProt accession number Q6XDB5).

For the enzyme from *Abies grandis* a particular reaction was also observed (Schwab et al., Arch. Biochem. Biophys. 392 (2001), 123-136), namely the following:

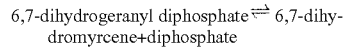
6,7-dihydrogeranyl diphosphate ⇌ 6,7-dihydromyrcene+diphosphate

In principle, any known pinene synthase can be employed in the method according to the invention. In a preferred embodiment, the pinene synthase employed in a method according to the present invention is a pinene synthase from *Abies grandis* (UniProt accession number O244475; Schwab et al., Arch. Biochem. Biophys. 392 (2001), 123-136).

Methods for the determination of pinene synthase activity are known in the art and are described, for example, in Schwab et al. (Archives of Biochemistry and Biophysics 392 (2001), 123-136). In a typical assay, the assay mixture for pinene synthase consists of 2 ml assay buffer (50 mM Tris/HCl, pH 7.5, 500 mM KCl, 1 mM MnCl2, 5 mM dithiothreitol, 0.05% NaHSO3, and 10% glycerol) containing 1 mg of the purified protein. The reaction is initiated in a Teflon-sealed screw-capped vial by the addition of 300 mM substrate. Following incubation at 25° C. for variable periods (0.5-24 h), the mixture is extracted with 1 ml of diethyl ether. The biphasic mixture is vigorously mixed and then centrifuged to separate the phases. The organic extract is dried (MgSO4) and subjected to GC-MS and MDGC analysis.

As indicated above, it is also possible to employ a monoterpene synthases in a method according to the invention. Particularly preferred are the monoterpene synthase from *Melaleuca alternifolia* described in Shelton et al. (Plant Physiol. Biochem. 42 (2004), 875-882; an example for such an enzyme is provided in SEQ ID NO: 11) or the monoterpene synthase from *Eucalyptus globulus* (UniProt accession number Q0PCI4; an example for such an enzyme is provided in SEQ ID NO: 8). In a particularly preferred embodiment any protein showing an amino acid sequence as shown in any one of SEQ ID NO: 11 or 8 or showing an amino acid sequence which is at least 80% homologous to any of SEQ ID NO: 11 or 8 and having the activity of a monoterpene synthase can be employed in a method according to the present invention.

Figure 11:
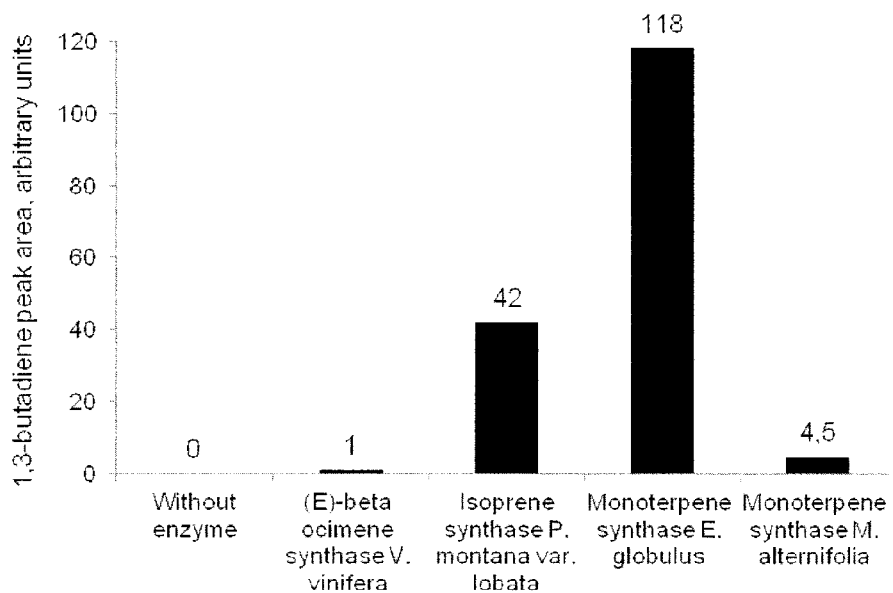

The present inventors have shown that different types of terpene synthases, e.g. isoprene synthases, (E)-beta-ocimene and monoterpene synthase from different plant organisms are able to convert crotyl phosphate into butadiene (see Examples 12 and 13 and FIG. 11).

The reactions catalyzed by the various terpene synthases, in particular the terpene synthases mentioned above, show certain common features. For example, the reactions catalyzed by isoprene synthases, by myrcene/ocimene synthases, by farnesene synthases, by pinene synthase and by monoterpene synthases, respectively, are all believed to proceed through a common mechanism in which, in a first step a carbocation is created by elimination of the diphosphate ($PP_i$), which is then followed by direct deprotonation so as to form the corresponding diene. It could be shown by the present inventors that enzymes which belong to the family of terpene synthases are able to convert crotyl phosphate into butadiene.

In another embodiment of the method according to the invention step A(ii) consists of two enzymatic reactions comprising:
(a) the enzymatic conversion of crotyl phosphate into crotyl diphosphate; and
(b) the enzymatic conversion of crotyl diphosphate into butadiene.

This option is in the following referred to as option A(ii2) and the different steps are referred to as steps A(ii2a) and A(ii2b).

As regards step A(ii2a), the enzymatic conversion of crotyl phosphate into crotyl diphosphate can be achieved by the use of an enzyme which can catalyze the transfer of a phospho group onto a molecule, such as kinases. Preferably, ATP is the donor of the phospho group in such a reaction. The conversion can in particular, e.g., be achieved by the use of an isopentenyl phosphate kinase. This enzyme has so far not yet been classified and, therefore, no EC number is available. It is predicted to be a member of the amino acid kinase superfamily, in particular the aspartokinase superfamily. The enzyme isopentenyl phosphate kinase catalyzes the following reaction:

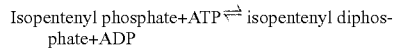
Isopentenyl phosphate+ATP ⇌ isopentenyl diphosphate+ADP

This enzyme participates in an alternative branch of the mevalonate pathway which has been discovered in the archaeon *Methanocaldococcus jannaschii*. It is a small molecule kinase. The primary amino acid sequence and the crystal structure of the isopentenyl phosphate kinase of *Methanocaldococcus jannaschii* has already been disclosed as well as mutants which are able to use oligoprenyl monophosphates as substrate (Dellas and Noel, ACS Chem. Biol. 5 (2010), 589-601). The active site has been characterized and the amino acid residues crucial for binding and catalysis of the reaction have been identified. Because of the high structural similarity of isopentenyl phosphate and crotyl phosphate and the fact that mutants of the isopentenyl phosphate kinase of *Methanocaldococcus jannaschii* have already been shown to be able to use other oligoprenyl monophosphates as substrates, it can be expected that this enzyme or mutants thereof will also be able to convert crotyl phosphate into crotyl diphosphate. The sequence of the isopentenyl phosphate kinase from *Methanocaldococcus jannaschii* is shown in SEQ ID NO: 6.

Genes encoding an isopentenyl phosphate kinase are also known from *Methanothermobacter thermautotrophicus* (MTH) and from *Thermoplasma acidophilum* (THA) (Chen and Poulter, Biochemistry 49 (2010), 207-217). For both these enzymes crystal structures have been determined (Mabanglo et al., ACS Chem. Biol. 5 (2010), 517-527). The sequence of the isopentenyl phosphate kinase from *Methanothermobacter thermautotrophicus* is shown in SEQ ID NO: 5. The sequence of the isopentenyl phosphate kinase from *Thermoplasma acidophilum* is shown in SEQ ID NO: 4. In a particularly preferred embodiment any protein showing an amino acid sequence as shown in any one of SEQ ID NOs: 4 to 6 or showing an amino acid sequence which is at least 80% homologous to any of SEQ ID NOs: 4 to 6 and having the activity of an isopentenyl phosphate kinase can be employed in a method according to the present invention.

As regards step A(ii2b), the enzymatic conversion of crotyl diphosphate into butadiene involves the removal of a diphosphate group from crotyl diphosphate with the simultaneous production of butadiene. An enzyme which can catalyze this reaction is referred to as a crotyl diphosphate diphosphate-lyase (butadiene forming). Examples of enzymes which can catalyze the dephosphorylation of crotyl diphosphate into butadiene are enzymes which can be classified as belonging to the terpene synthase family. Preferably such an enzyme belongs to the family of plant terpene synthases. These enzymes have already been disclosed in detail hereinabove in connection with the conversion of crotyl phosphate into butadiene and the same applies here.

Preferably the terpene synthase is an isoprene synthase (EC 4.2.3.27), a myrcene/ocimene synthase (EC 4.2.3.15), a farnesene synthase (EC 4.2.3.46 or EC 4.2.3.47) or a pinene synthase (EC 4.2.3.14). Also enzymes which are generally classified as monoterpene synthases can be used. Particularly preferred the terpene synthase is an isoprene synthase, an (E)-beta ocimene synthase or a monoterpene synthase.

In a particularly preferred embodiment the dephosphorylation of crotyl diphosphate into butadiene is achieved by the use of an isoprene synthase (EC 4.2.3.27). As regards the isoprene synthase to be employed in the method, the same applies as has been described herein above. In a particularly preferred embodiment the isoprene synthase employed is an isoprene synthase from *P. montana* var. *lobata*. As explained above, crotyl diphosphate is structurally closely related to dimethylallyl diphosphate. Therefore, it is considered that an isoprene synthase can also use crotyl diphosphate as a substrate and can convert it into butadiene.

In another particularly preferred embodiment, the dephosphorylation of crotyl diphosphate into butadiene is achieved by the use of a myrcene/ocimene synthase (EC 4.2.3.15). As regards the myrcene/ocimene synthase to be employed in the method, the same applies as has been described herein above. In a particularly preferred embodiment the myrcene/ocimene synthase employed is an (E)-beta ocimene synthase, most preferably an (E)-beta ocimene synthase from *Vitis vinifera* or from *L. japonicus* or from *P. lunatus*.

In another particularly preferred embodiment, the dephosphorylation of crotyl diphosphate into butadiene is achieved by the use of a monoterpene synthase. As regards the monoterpene synthase to be employed in the method, the same applies as has been described herein above. In a particularly preferred embodiment the monoterpene synthase employed is a monoterpene synthase from *Eucalyptus globulus*.

Figure 13:
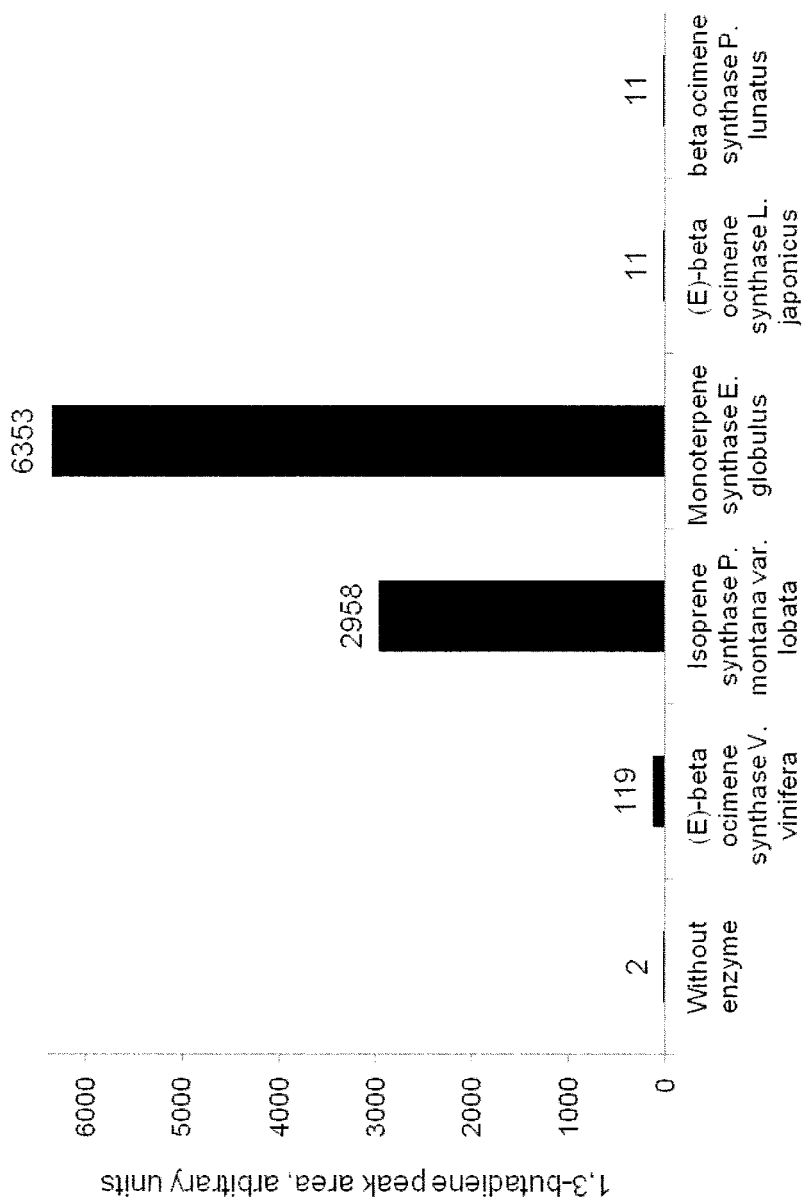

The present inventors have shown that different types of terpene synthases, e.g. isoprene synthase, (E)-beta-ocimene and monoterpene synthase from different plant organisms are able to convert crotyl diphosphate into butadiene (see Examples 14 and 15 and FIG. 13).

In another aspect (B), the method according to the invention comprises the two enzymatic steps of
(I) enzymatically converting crotyl alcohol into crotyl diphosphate; and
(II) enzymatically converting crotyl diphosphate into butadiene.

This alternative is in the following referred to as Alternative B and the different steps are referred to as B(I) and B(II).

In this embodiment the enzymatic conversion of crotyl alcohol into crotyl diphosphate according to step B(I) consists of a single enzymatic reaction in which crotyl alcohol is directly converted into crotyl diphosphate.

The direct enzymatic conversion of crotyl alcohol into crotyl diphosphate in one step can, e.g., be achieved by the use of an enzyme which is able to catalyze the transfer of a diphosphate group, such as a diphosphotransferase, for example enzymes which are classified as EC 2.7.6 (diphosphotransferases). Examples are 2-amino-4-hydroxy-6-hydroxymethyldihydropteridine diphosphokinase (EC 2.7.6.3) and thiamine diphosphokinase (EC 2.7.6.2). Preferably, ATP is the donor of the diphosphate group in such a reaction.

Thus, in one embodiment the direct enzymatic conversion of crotyl alcohol into crotyl diphosphate in one step can be achieved by the use of a 2-amino-4-hydroxy-6-hydroxymethyldihydropteridine diphosphokinase (EC 2.7.6.3). This enzyme catalyzes the following reaction:

2-amino-4-hydroxy-6-hydroxymethyl-7,8-dihydropteridine+ATP $\rightleftharpoons$ 2-amino-7,8-dihydro-4-hydroxy-6-(diphosphooxymethyl)pteridine+AMP The occurrence of this enzyme has been described for several organisms, e.g. for *E. coli, Plasmodium falciparum, Plasmodium chabaudi, Streptococcus pneumoniae, Toxoplasma gondii, Yersinia pestis, Pneumocystis carinii, Haemophilus influenzae, S. cerevisiae, Arabidopsis thaliana* and *Pisum sativum*.

In principle, any known 2-amino-4-hydroxy-6-hydroxymethyldihydropteridine diphosphokinase can be employed in the method according to the invention.

In another embodiment the direct enzymatic conversion of crotyl alcohol into crotyl diphosphate in one step can be achieved by the use of a thiamine diphosphokinase (EC 2.7.6.2). This enzyme catalyzes the following reaction:

ATP+thiamine $\rightleftharpoons$ AMP+thiamine diphosphate

The occurrence of this enzyme has been described for several organisms, e.g. for *Salmonella enterica, Plasmodium falciparum, Saccharomyces cerevisiae, Schizosaccharomyces pombe, Candida albicans, Arabidopsis thaliana, Caenorhabditis elegans, Rattus norvegicus, Mus musculus* and *Homo sapiens*. In principle, any known thiamine diphosphokinase can be employed in the method according to the invention.

In step B(II) the obtained crotyl diphosphate is then further converted enzymatically into butadiene. This enzymatic conversion of crotyl diphosphate into butadiene involves the removal of a diphosphate group and can, e.g., be achieved by the use of terpene synthase as described herein above. As regards the preferred embodiments, the same applies as set forth herein above.

In a particularly, preferred embodiment an isoprene synthase (EC 4.2.3.27) is employed for the conversion of crotyl diphosphate into butadiene.

The crotyl alcohol which is used as a substrate for the enzymatic production of butadiene according to the invention can either be supplied externally or it can itself be provided by the reduction of crotonaldehyde (but-2-enal). This reduction can, e.g., be achieved by chemical reactions as known to the person skilled in the art. However, according to the present invention it is preferable that the provision of crotyl alcohol is achieved by the enzymatic conversion of crotonyl-Coenzyme A (in the following crotonyl-CoA; see FIG. 9) or of crotonaldehyde into crotyl alcohol. Thus, in another embodiment the method according to the invention further comprises the step of providing crotyl alcohol by the enzymatic conversion of crotonaldehyde into crotyl alcohol as described herein below. Crotonaldehyde ($CH_3CH=CHCHO$; (2E)-but-2-enal) occurs naturally, e.g. in soybean oils, and can be synthesized chemically by the aldol condensation of acetaldehyde. Alternatively, the method according to the invention further comprises the step of providing crotyl alcohol by the enzymatic conversion of crotonyl-CoA into crotyl alcohol as described below. Crotonyl-coenzyme A is a thioester between crotonic acid and Coenzyme A. It is an intermediate in the fermentation of butyric acid, and in the metabolism of lysine and tryptophan. During degradation of these amino acids, α-ketoadipate is produced which is converted into glutaryl-CoA by oxidative decarboxylation. Glutaryl-CoA is then converted by glutaryl-CoA dehydrogenase into crotonyl-CoA, which can be converted in two further steps into two molecules of acetyl-CoA. Crotonyl-CoA is also a metabolite in the fermentation of glucose by some obligatory anaerobe bacteria in which butyric acid is produced, such as *Clostridium acetobutylicum*. Moreover, crotonyl-CoA had been isolated in some microorganisms which assimilate acetate via the so-called ethyl-malonyl-CoA pathway. It also occurs as an intermediate in some metabolic pathways leading to the assimilation of carbon dioxide, e.g. in the 3-hydroxyproprionate/4-hydroxybutyrate cycle or the dicarboxylate/4-hydroxybutyrate cycle.

The present inventor also developed a method for enzymatically producing crotyl alcohol enzymatically starting from crotonaldehyde or from crotonyl-CoA.

Thus, in a second aspect, the present invention relates to a method for producing crotyl alcohol. Such a method comprises the enzymatic conversion of crotonyl-CoA into crotonaldehyde and the subsequent enzymatic conversion of crotonaldehyde into crotyl alcohol. The first reaction may occur according to the following schemes:

Crotonyl-CoA+NADH+H+ $\rightleftharpoons$ crotonaldehyde+CoA+NAD$^+$ or

Crotonyl-CoA+NADPH+H+ $\rightleftharpoons$ crotonaldehyde+CoA+NADP$^+$

This reaction is a reduction and can be catalyzed by various enzymes. In one aspect, it is possible to use for the above indicated conversion of crotonyl-CoA to crotonaldehyde a hydroxymethylglutaryl-CoA reductase (EC 1.1.1.34). This enzyme normally catalyzes the following reaction (S)-3-hydroxy-methylglutaryl-CoA+2NADPH+H+ $\rightleftharpoons$ (R)-mevalonate+CoA+2NADP$^+$ Enzymes belonging to this class and catalyzing the above shown conversion occur in organisms of all kingdoms, i.e. plants, animals, fungi, bacteria etc. and have extensively been described in the literature. Nucleotide and/or amino acid sequences for such enzymes have been determined for numerous organisms, in particular bacterial organisms. In principle, any hydroxymethylglutaryl-CoA reductase (EC 1.1.1.34) can be used in the context of the present invention.

Alternatively or in addition, the above described conversion of crotonyl-CoA into crotonaldehyde can also be achieved by using an enzyme referred to as acetaldehyde dehydrogenase (EC 1.2.1.10). This enzyme normally catalyzes the following reaction Acetyl-CoA+NADH+H+ ⇌ acetaldehyde+CoA+ NAD+

Enzymes belonging to this class and catalyzing the above shown conversion occur in several types of bacteria, like *e. coli, Acinetobacter* sp., *Leuconostoc mesenteroides, Pseudomonas* sp, *Clostridium beijerinckii, Clostridium kluyveri, Giardia intestinalis, Propionibacterium freudenreichii* and *Thermoanaerobacter ethanolicus* In principle, any acetaldehyde dehydrogenase (EC 1.2.1.10) can be used in the context of the present invention.

Alternatively or in addition, the above described conversion of crotonyl-CoA into crotonaldehyde can also be achieved by using an enzyme referred to as aldehyde-alcohol dehydrogenase, such as the aldehyde-alcohol dehydrogenase as encoded by an adhE gene. Such an enzyme is bifunctional in that it shows at least the enzymatic activities of an alcohol dehydrogenase and an aldehyde dehydrogenase, such as an acetaldehyde dehydrogenase. An example for such an enzyme is the aldehyde-alcohol dehydrogenase of *E. coli* (adhE; UniProtKB/Swiss-Prot Accession number P0A9Q7; Jul. 27, 2011; Version 58). Corresponding enzymes are also known from other organisms, such as, e.g. *Leuconostoc mesenteroides* (Koo et al., Biotechnology Letters 27, 505-510), *Polytomella* sp. and *Chlamydomonas reinhardtii* (Atteia et al., Plant Mol. Biol. 53 (2003), 175-188). Genes encoding such enzymes have been found in the genomes of several Gram-positive bacteria belonging to the categories bacilli and clostridia, in several gamma-proteobacteria, in actinobacteria, in cyanobacteria and some amitochondriate protists (see Atteia et al., loc. cit.).

Alternatively or in addition, the above described conversion of crotonyl-CoA into crotonaldehyde can also be achieved by using enzymes referred to as acyl-CoA reductases. Examples for such enzymes are cinnamoyl-CoA reductase (EC 1.2.1.44), long-chain-fatty-acyl-CoA reductase (EC 1.2.1.50) and malonyl-CoA reductase (malonate semialdehyde-forming; EC 1.2.1.75).

According to the present invention the produced crotonaldehyde is further converted into crotyl alcohol. The enzymatic conversion of crotonaldehyde into crotyl alcohol is a reduction/hydrogenation and may occur according to the following schemes:

Crotonaldehyde+NADH+H+ ⇌ crotyl alcohol+NAD+ or

Crotonaldehyde+NADPH+H+ ⇌ crotyl alcohol+ NADP+

This reaction can be catalyzed by various enzymes. In one aspect, it is possible to use for the above indicated conversion of crotonaldehyde to crotyl alcohol an enzyme which is known to be able to catalyze this reaction. One example is the aldo-keto reductase (AKR) encoded by the sakR1 gene. This enzyme had been identified in *Synechococcus* sp. PCC 7002 and has been described in Dongyi et al. (Microbiol. 152 (2006), 2013-2021). It uses NADPH/NADP+ as a cofactor. Another example is the aldo-keto reductase (AKR) encoded by the At2g37770 gene, which had been identified in *Arabidopsis* (Yamauchii et al. (J. Biol. Chem. 286 (2011) 6999-7009). It uses NADPH/NADP+ as a cofactor. A further example is the 321-MB dehydrogenase from the soil bacterium *Pseudomonas putida* MB-1 (Malone et al., Appl. Environm. Microbiol. 65 (1999), 2622-2630) which uses NADH/NAD+ as a cofactor.

In another embodiment it is also possible to use for the above indicated conversion of crotonaldehyde to crotyl alcohol a hydroxymethylglutaryl-CoA reductase (EC 1.1.1.34). This enzyme has already been described above and that what had been said above holds also true for this reaction.

Alternatively or in addition, the above described conversion of crotonaldehyde into crotyl alcohol can also be achieved by using an alcohol dehydrogenase (EC 1.1.1.1). Such an enzyme normally catalyzes the following reaction Primary alcohol+NAD+ ⇌ aldehyde+NADH+H+

Enzymes belonging to this class and catalyzing the above shown conversion occur in organisms of all kingdoms, i.e. plants, animals, fungi, bacteria etc. and have extensively been described in the literature. Nucleotide and/or amino acid sequences for such enzymes have been determined for numerous organisms, in particular bacterial organisms. In principle, any alcohol dehydrogenase (EC 1.1.1.1) can be used in the context of the present invention.

Moreover, the conversion of crotonaldehyde to crotyl alcohol can also be achieved by the use of an enzyme referred to as an aldehyde reductase. Examples for such enzymes are alcohol dehydrogenase (NADP+; EC 1.1.1.2), allyl-alcohol dehydrogenase (EC 1.1.1.54), retinol dehydrogenase (EC 1.1.1.105), sulcatone dehydrogenase (EC 1.1.1.260) and 3-methylbutanal reductase (EC 1.1.1.265)

The enzymatic conversion of crotonyl-CoA into crotyl alcohol may also occur according to the following schemes:

Crotonyl-CoA+2NADH+2H+ ⇌ crotyl alcohol+ CoA+2NAD+ or

Crotonyl-CoA+2NADPH+2H+ ⇌ crotyl alcohol+ CoA+2NADP+

Similar to the above described conversions, this reaction goes via crotonaldehyde as an intermediate. However, in this embodiment of the invention, the conversion of crotonyl-CoA into crotyl alcohol is catalyzed by one enzyme which catalyses both reduction/hydrogenation steps. An enzyme which may be employed in this conversion is an aldehyde-alcohol dehydrogenase, such as the aldehyde-alcohol dehydrogenase as encoded by an adhE gene which had already been described above.

Another enzyme which may be used in this conversion is a hydroxymethylglutaryl-CoA reductase (EC 1.1.1.34) which has already been described above. In a further preferred embodiment the conversion of crotonyl-CoA into crotyl alcohol is achieved by the use of a short-chain dehydrogenase/fatty acyl-CoA reductase.

The term "short-chain dehydrogenase/fatty acyl-CoA reductase" or "short-chain dehydrogenases/reductases (SDR)" in the context of the present invention refers to enzymes which are characterized by the following features:
1. They catalyze a two-step reaction in which fatty acy-CoA is reduced to fatty alcohol.
2. They show a substrate specificity for acyl-CoA containing an aliphatic chain from 8 to 20 carbon atoms.

Preferably such enzymes are furthermore characterized by the feature that they show a specific motif in their primary structure, i.e. amino acid sequence, namely they show two specific glycine motifs for NADP(H) binding.

The short-chain dehydrogenase/fatty acyl-CoA reductase or short-chain dehydrogenases/reductases (SDR) enzymes constitute a family of enzymes, most of which are known to be NAD- or NADP-dependent oxidoreductase (Jornvall H. et al., Biochemistry 34 (1995), 6003-6013). Recently, a novel bacterial NADP-dependent reductase from *Marinobacter aquaeolei* VT8 was characterized (Willis et al., Biochemistry 50 (2011), 10550-10558). This enzyme catalyzes the four-electron reduction of fatty acyl-CoA substrates to the corresponding fatty alcohols. The enzymatic conversion of fatty acyl-CoA into fatty alcohol occurs through an aldehyde intermediate according to the following scheme:

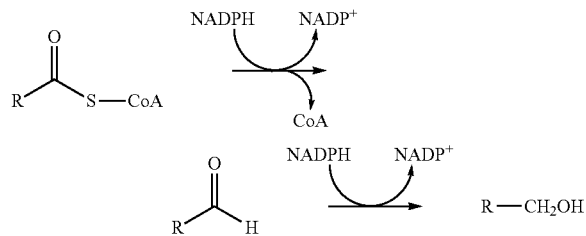

The enzyme displays activity on fatty acyl-CoA substrates ranging from 8 to 20 carbons in length (both saturated and unsaturated) as well as on fatty aldehyde substrates. Characteristically, proteins of this family possess two NAD(P)(H)-binding motifs, which have the conserved sequence GXGX (1-2×)G (SEQ ID NO: 20) (Willis et al., Biochemistry 50 (2011), 10550-10558; Jornvall H. et al., Biochemistry 34 (1995), 6003-6013). The first pattern, GTGFIG (SEQ ID NO: 18), is identified near the N-terminus and the second signature sequence, GXXXGXG (SEQ ID NO: 21), is located between residues 384-390.

In principle any "short-chain dehydrogenase/fatty acyl-CoA reductase" or "short-chain dehydrogenases/reductases (SDR)" can be applied in the method according to the invention.

Preferably, the short-chain dehydrogenase/fatty acyl-CoA reductase is a short-chain dehydrogenase/fatty acyl-CoA reductase from a marine bacterium, preferably from the genus *Marinobacter* or *Hahella*, even more preferably from the species *Marinobacter aquaeolei*, more preferably *Marinobacter aquaeolei* VT8, *Marinobacter manganoxydans*, *Marinobacter algicola*, *Marinobacter* sp. ELB17 or *Hahelly chejuensis*. Examples of such enzymes are the short-chain dehydrogenase/fatty acyl-CoA reductase from *Marinobacter aquaeolei* VT8 (Uniprot accession number A1U3L3; Willis et al., Biochemistry 50 (2011), 10550-10558), the short-chain dehydrogenase from *Marinobacter manganoxydans* (Uniprot accession number G6YQS9), the short-chain dehydrogenase from *Marinobacter algicola* (Uniprot accession number A6EUH6), the short-chain dehydrogenase from *Marinobacter* sp. ELB17 (Uniprot accession number A3JCC5) and the short-chain dehydrogenase from *Hahella chejuensis* (Uniprot accession number Q2SCE0).

The sequence of the short-chain dehydrogenase/fatty acyl-CoA reductase from *Marinobacter aquaeolei* VT8 is shown in SEQ ID NO: 13. The sequence of the short-chain dehydrogenase/fatty acyl-CoA reductase from *Marinobacter manganoxydans* is shown in SEQ ID NO: 14. The sequence of the short-chain dehydrogenase/fatty acyl-CoA reductase from *Marinobacter* sp. ELB17 is shown in SEQ ID NO: 15. The sequence of the short-chain dehydrogenase/fatty acyl-CoA reductase from *Marinobacter algicola* is shown in SEQ ID NO: 16. The sequence of the short-chain dehydrogenase/fatty acyl-CoA reductase from *Hahella chejuensis* is shown in SEQ ID NO: 17. In a particularly preferred embodiment any protein showing an amino acid sequence as shown in any one of SEQ ID NOs: 13 to 17 or showing an amino acid sequence which is at least 80% homologous to any of SEQ ID NOs: 13 to 17 and having the activity of a short-chain dehydrogenase/fatty acyl-CoA reductase can be employed in a method according to the present invention.

The methods according to the first and second aspect of the present invention as described above may also be combined, i.e. it is possible that a method according to the first aspect of the invention for the production of butadiene from crotyl alcohol further comprises the steps of a method according to the second aspect of the invention for the provision of crotyl alcohol by enzymatic reactions as described above.

In another embodiment the methods according to the first and/or second aspect of the invention may also include the further step of enzymatically providing crotonyl-CoA. This may be achieved by the enzymatic conversion of 3-hydroxybutyryl-Coenzyme A into crotonyl-Coenzyme A. This reaction may occur according to the following scheme:

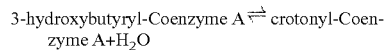

This reaction corresponds to a Michael elimination and can, for example, be catalyzed by an enzyme called 3-hydroxybutyryl-CoA dehydratase which is classified as EC 4.2.1.55. This enzyme belongs to the family of lyases, specifically the hydro-lyases, which cleave carbon-oxygen bonds. The systematic name of this enzyme class is (3R)-3-hydroxybutanoyl-CoA hydro-lyase (crotonoyl-CoA-forming). Other names in common use include D-3-hydroxybutyryl coenzyme A dehydratase, D-3-hydroxybutyryl-CoA dehydratase, enoyl coenzyme A hydrase (D), and (3R)-3-hydroxybutanoyl-CoA hydro-lyase. This enzyme participates in butanoate metabolism. Enzymes belonging to this class and catalyzing the above shown conversion of 3-hydroxybutyryl-Coenzyme A into crotonyl-Coenzyme A have been described to occur, e.g. in rat (*Rattus norvegicus*) and in *Rhodospirillum rubrum*. Nucleotide and/or amino acid sequences for such enzymes have been determined, e.g. for *Aeropyrum pernix*. In principle, any 3-hydroxybutyryl-CoA dehydratase (EC 4.2.1.55) can be used in the context of the present invention.

Alternatively or in addition, the above described conversion of 3-hydroxybutyryl-Coenzyme A into crotonyl-Coenzyme A can also be achieved by using an enzyme referred to as enoyl-CoA hydratase (EC 4.2.1.17). Enoyl-CoA hydratase is an enzyme that normally hydrates the double bond between the second and third carbons on acyl-CoA. However, it can also be employed to catalyze the reaction in the reverse direction. This enzyme, also known as crotonase, is naturally involved in metabolizing fatty acids to produce both acetyl-CoA and energy. Enzymes belonging to this class have been described to occur, e.g. in rat (*Rattus norvegicus*), humans (*Homo sapiens*), mouse (*Mus musculus*), wild boar (*Sus scrofa*), Bos taurus, E. coli, Clostridium acetobutylicum and Clostridium aminobutyricum. Nucleotide and/or amino acid sequences for such enzymes have been determined, e.g. for rat, humans and *Bacillus subtilits*. In principle, any enoyl-CoA hydratase (EC 4.2.1.17) can be used in the context of the present invention.

In another embodiment it is also possible to use for the above described conversion of 3-hydroxybutyryl-Coenzyme A into crotonyl-Coenzyme A an enoyl-CoA hydratase 2 (EC 4.2.1.119) or a crotonyl-[acyl-carrier-protein] hydratase (EC 4.2.1.58).

In another embodiment the methods according to the first and/or second aspect of the invention may also include the further step of enzymatically providing 3-hydroxybutyryl-Coenzyme A. This can be achieved by the enzymatic conversion of acetoacetyl-CoA into 3-hydroxybutyryl-Coenzyme A. This reaction may occur according to the following scheme:

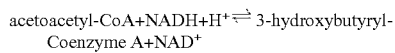

or

This reaction is a reduction and can, e.g., be catalyzed by an enzyme called acetoacetyl-CoA reductase which is classified as EC 1.1.1.36. Enzymes belonging to this class and catalyzing the above shown conversion of acetoactyl-CoA into 3-hydroxybutyryl-Coenzyme A occur in organisms of all kingdoms, i.e. plants, animals, fungi, bacteria etc. and have extensively been described in the literature. Nucleotide and/or amino acid sequences for such enzymes have been determined for numerous organisms, in particular bacterial organisms. In principle, any acetoacetyl-CoA reductase (EC 1.1.1.36) can be used in the context of the present invention. In one embodiment the enzyme employed in the method according to the invention originates from *E. coli*.

In yet a further embodiment the methods according to the first and/or second aspect of the invention may also include the further step of enzymatically providing acetoacetyl-CoA. This can be achieved by the enzymatic conversion of two molecules acetyl-CoA into one molecule of acetoacetyl-CoA. Acetyl-CoA is a metabolic intermediate which occurs in all living organisms and plays a central role in metabolism. Thus, according to the present invention, acetyl-CoA can, for example, be converted into acetoacetyl-CoA by the following reaction:

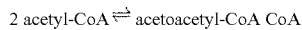

This reaction is catalyzed by enzymes called acetyl-CoA C-acetyltransferases which are classified as EC 2.3.1.9. Enzymes belonging to this class and catalyzing the above shown conversion of two molecules of acetyl-CoA into acetoacetyl-CoA and CoA occur in organisms of all kingdoms, i.e. plants, animals, fungi, bacteria etc. and have extensively been described in the literature. Nucleotide and/or amino acid sequences for such enzymes have been determined for a variety of organisms, like *Homo sapiens, Arabidopsis thaliana, E. coli, Bacillus subtilis* and *Candida*, to name just some examples. In principle, any acetyl-CoA C-acetyltransferase (EC 2.3.1.9) can be used in the context of the present invention.

Alternatively, the provision of acetoacetyl-CoA may also be achieved by the enzymatic conversion of acetyl-CoA and malonyl-CoA into acetoacetyl-CoA. This reaction is catalyzed by an enzyme called acetoacetyl-CoA synthase. The gene encoding this enzyme was identified in the mevalonate pathway gene cluster for terpenoid production in a soil-isolated Gram-positive *Streptomyces* sp. Strain CL190 (Okamura et al., PNAS USA 107 (2010) 11265-11270, 2010). Moreover a biosynthetic pathway using this enzyme for acetoacetyl-CoA production was recently developed in *E. coli* (Matsumoto K et al., Biosci. Biotechnol. Biochem, 75 (2), 364-366, 2011, enclosed)

The methods according to the present invention may be carried out in vitro or in vivo. An in vitro reaction is understood to be a reaction in which no cells are employed, i.e. an acellular reaction. Thus, in vitro preferably means in a cell-free system. The term "in vitro" in one embodiment means in the presence of isolated enzymes (or enzyme systems optionally comprising possibly required cofactors). In one embodiment, the enzymes employed in the method are used in purified form. For carrying out the process in vitro the substrates for the reaction and the enzymes are incubated under conditions (buffer, temperature, cosubstrates, cofactors etc.) allowing the enzymes to be active and the enzymatic conversion to occur. The reaction is allowed to proceed for a time sufficient to produce butadiene. The production of butadiene can be measured by methods known in the art, such as gas chromatography possibly linked to mass spectrometry detection.

The enzymes may be in any suitable form allowing the enzymatic reaction to take place. They may be purified or partially purified or in the form of crude cellular extracts or partially purified extracts. It is also possible that the enzymes are immobilized on a suitable carrier.

In one embodiment of the method according to the invention the substrate which is used in such an in vitro method is crotyl alcohol which is converted by the use of the above-mentioned enzymes to butadiene. In another embodiment, the substrate used in such an in vitro method is crotonaldehyde which is first converted into crotyl alcohol as described above which is then in turn converted into butadiene as described above.

The in vitro method according to the invention may be carried out in a one-pot-reaction, i.e. the substrate is combined in one reaction mixture with the above described enzymes necessary for the conversion into butadiene and the reaction is allowed to proceed for a time sufficient to produce butadiene. Alternatively, the method may also be carried out by effecting one or more enzymatic steps in a consecutive manner, i.e. by first mixing the substrate with one or more enzymes and allowing the reaction to proceed to an intermediate and then adding one or more further enzymes to convert the intermediate further either into an intermediate or into butadiene.

The in vitro method according to the invention furthermore may comprise the step of collecting gaseous products, in particular butadiene, degassing out of the reaction, i.e. recovering the products which degas, e.g., out of the culture. Thus, in one embodiment, the method is carried out in the presence of a system for collecting butadiene under gaseous form during the reaction.

As a matter of fact, butadiene adopts the gaseous state at room temperature and atmospheric pressure. The method according to the invention therefore does not require extraction of the product from the reaction mixture, a step which is always very costly when performed at industrial scale. The evacuation and storage of butadiene and its possible subsequent physical separation from other gaseous substances as well as its chemical conversion can be performed according to any method known to one of skill in the art. For example, butadiene can be separated from $CO_2$ by the condensation of $CO_2$ at low temperatures. $CO_2$ can also be removed by polar solvents, e.g. ethanolamine. Moreover, it can be isolated by adsorption on a hydrophobic membrane.

In another embodiment the method according to the invention is carried out in culture, in the presence of an organism, preferably a microorganism, producing at least the enzymes described above which are necessary to produce butadiene according to a method of the invention according to the first aspect by using one of the alternative routes A or B described above and starting either from crotyl alcohol or from crotonaldehyde. Thus, in such an embodiment of the invention, an organism, preferably a microorganism, that produces the enzymes specified in the description of alternatives A or B, above, is used. It is possible to use a (micro)organism which naturally produces one or more of the required enzymes and to genetically modify such a (micro)organism so that it expresses also those enzymes which it does not naturally express. Preferably a (micro)organism is used which has been genetically modified as described hereinabove in connection with the second aspect of the invention so as to be able to produce crotyl alcohol.

In alternative A1 it is for example possible to use *Bacillus subtilis* which possesses a gene encoding the enzyme hydroxyethylthiazole kinase and a gene encoding, a terpene synthase, e.g. an isoprene synthase. Such a bacterium may be further genetically modified as described herein above so as to be able to produce crotyl alcohol.

In alternative B it is, e.g., possible to use *E. coli* or *S. cerevisiae*, which both possess a gene encoding 2-amino-4-hydroxy-6-hydroxymethyldihydropteridine diphosphokinase, and to introduce into such a microorganism a gene, for example from *Bacillus subtilis* encoding a terpene synthase, e.g. an isoprene synthase. Similarly, it is possible to use in alternative B as a microorganism *B. subtilis* and to genetically modify it with a gene encoding a 2-amino-4-hydroxy-6-hydroxymethyldihydropteridine diphosphokinase, e.g. from *E. coli* or from *S. cerevisiae*. Again, such microorganisms may be further genetically modified as described herein above so as to be able to produce crotyl alcohol.

If a (micro)organism is used which naturally expresses one of the required enzyme activities, it is possible to modify such a (micro)organism so that this activity is overexpressed in the (mircro)organism. This can, e.g., be achieved by effecting mutations in the promoter region of the corresponding gene so as to lead to a promoter which ensures a higher expression of the gene. Alternatively, it is also possible to mutate the gene as such so as to lead to an enzyme showing a higher activity.

By using (micro)organisms which express the enzymes which are necessary according to alternative A or B as described above, it is possible to carry out the method according to the invention directly in the culture medium, without the need to separate or purify the enzymes.

In one embodiment, a (micro)organism is used having the natural or artificial property of endogenously producing crotyl alcohol, and also expressing or overexpressing the enzymes as described in connection with alternatives A and B, above, so as to produce butadiene directly from a carbon source present in solution. In another embodiment, the (micro)organism which is used has the natural or artificial property of endogenously producing crotonaldehyde and to convert it into crotyl alcohol which can then be further converted into butadiene.

In one embodiment the organism employed in the method according to the invention is an organism, preferably a microorganism, which has been genetically modified to contain one or more foreign nucleic acid molecules encoding one or more of the enzymes as described above in connection with alternatives A or B. The term "foreign" in this context means that the nucleic acid molecule does not naturally occur in said organism/microorganism. This means that it does not occur in the same structure or at the same location in the organism/microorganism. In one preferred embodiment, the foreign nucleic acid molecule is a recombinant molecule comprising a promoter and a coding sequence encoding the respective enzyme in which the promoter driving expression of the coding sequence is heterologous with respect to the coding sequence. Heterologous in this context means that the promoter is not the promoter naturally driving the expression of said coding sequence but is a promoter naturally driving expression of a different coding sequence, i.e., it is derived from another gene, or is a synthetic promoter or a chimeric promoter. Preferably, the promoter is a promoter heterologous to the organism/microorganism, i.e. a promoter which does naturally not occur in the respective organism/microorganism. Even more preferably, the promoter is an inducible promoter. Promoters for driving expression in different types of organisms, in particular in microorganisms, are well known to the person skilled in the art.

In a further embodiment the nucleic acid molecule is foreign to the organism/microorganism in that the encoded enzyme is not endogenous to the organism/microorganism, i.e. is naturally not expressed by the organism/microorganism when it is not genetically modified. In other words, the encoded enzyme is heterologous with respect to the organism/microorganism. The foreign nucleic acid molecule may be present in the organism/microorganism in extrachromosomal form, e.g. as a plasmid, or stably integrated in the chromosome. A stable integration is preferred. Thus, the genetic modification can consist, e.g. in integrating the corresponding gene(s) encoding the enzyme(s) into the chromosome, or in expressing the enzyme(s) from a plasmid containing a promoter upstream of the enzyme-coding sequence, the promoter and coding sequence preferably originating from different organisms, or any other method known to one of skill in the art.

In a preferred embodiment the (micro)organism of the present invention is also genetically modified so as to be able to produce crotyl alcohol as described herein above.

The organisms used in the invention can be prokaryotes or eukaryotes, preferably, they are microorganisms such as bacteria, yeasts, fungi or molds, or plant cells or animal cells. In a particular embodiment, the microorganisms are bacteria, preferably of the genus *Escherichia* or *Bacillus* and even more preferably of the species *Escherichia coli* or *Bacillus subtilis*.

In another embodiment, the microorganisms are recombinant bacteria of the genus *Escherichia* or *Bacillus*, preferably of the species *Escherichia coli* or *Bacillus subtilis*, having been modified so as to endogenously produce crotyl alcohol and to convert it into butadiene.

It is also possible to employ an extremophilic bacterium such as *Thermus thermophilus*, or anaerobic bacteria from the family Clostridiae.

In one embodiment the microorganism is a fungus, more preferably a fungus of the genus *Saccharomyces, Schizosaccharomyces, Aspergillus, Trichoderma, Pichia* or *Kluyveromyces* and even more preferably of the species *Saccharomyces cerevisiae, Schizosaccharomyces pombe, Aspergillus niger, Trichoderma reesei, Pichia pastoris* or of the species *Kluyveromyces lactis*. In a particularly preferred embodiment the microorganism is a recombinant yeast capable of producing crotyl alcohol and converting it into butadiene due to the expression of the enzymes described in connection with alternatives A or B, above.

In another embodiment, the method according to the invention makes use of a photosynthetic microorganism expressing at least the enzymes as described in connection with alternatives A or B, above. Preferably, the microorganism is a photosynthetic bacterium, or a microalgae. In a further embodiment the microorganism is an algae, more preferably an algae belonging to the diatomeae. Even more preferably such a microorganism has the natural or artificial property of endogenously producing crotyl alcohol. In this case the microorganism would be capable of producing butadiene directly from $CO_2$ present in solution.

In another embodiment, it is possible to use a microorganism which belongs to the group of acetogenic bacteria which are capable of converting CO (or $CO_2+H_2$) to produce acetyl-CoA via the so-called Wood-Ljungdahl pathway (Köpke et al.; PNAS 10 (2010), 13087-13092). A fermentation process using such microorganisms is known as syngas fermentation. Strictly mesophilic anaerobes such as *C. ljungdahlii, C. aceticum, Acetobacterium woodii, C. autoethanogenum*, and C. carboxydeviron, are frequently being used in syngas fermentation (Munasingheet et al.; Bioresource Technology 101 (2010), 5013-5022).

It is also conceivable to use in the method according to the invention a combination of (micro)organisms wherein different (micro)organisms express different enzymes as described above. In a further embodiment at least one of the microorganisms is capable of producing crotyl alcohol or, in an alternative embodiment, a further microorganism is used in the method which is capable of producing crotyl alcohol.

In another embodiment the method according to the invention makes use of a multicellular organism expressing at least the enzymes as described in connection with alternatives A or B, above. Examples for such organisms are plants or animals.

In a particular embodiment, the method according to the invention involves culturing microorganisms in standard culture conditions (30-37° C. at 1 atm, in a fermenter allowing aerobic growth of the bacteria) or non-standard conditions (higher temperature to correspond to the culture conditions of thermophilic organisms, for example).

In a further embodiment the method of the invention is carried out under microaerophilic conditions. This means that the quantity of injected air is limiting so as to minimize residual oxygen concentrations in the gaseous effluents containing butadiene.

In another embodiment the method according to the invention furthermore comprises the step of collecting the gaseous butadiene degassing out of the reaction. Thus in a preferred embodiment, the method is carried out in the presence of a system for collecting butadiene under gaseous form during the reaction.

As a matter of fact, butadiene adopts the gaseous state at room temperature and atmospheric pressure. The method according to the invention therefore does not require extraction of butadiene from the liquid culture medium, a step which is always very costly when performed at industrial scale. The evacuation and storage of butadiene and its possible subsequent physical separation and chemical conversion can be performed according to any method known to one of skill in the art and as described above.

In a particular embodiment, the method also comprises detecting butadiene which is present in the gaseous phase. The presence of butadiene in an environment of air or another gas, even in small amounts, can be detected by using various techniques and in particular by using gas chromatography systems with infrared or flame ionization detection, or by coupling with mass spectrometry.

When the process according to the invention is carried out in vivo by using an organism/microorganism providing the respective enzyme activities, the organism, preferably microorganism, is cultivated under suitable culture conditions allowing the occurrence of the enzymatic reaction. The specific culture conditions depend on the specific organism/microorganism employed but are well known to the person skilled in the art. The culture conditions are generally chosen in such a manner that they allow the expression of the genes encoding the enzymes for the respective reactions.

Various methods are known to the person skilled in the art in order to improve and fine-tune the expression of certain genes at certain stages of the culture such as induction of gene expression by chemical inducers or by a temperature shift.

In another embodiment the organism employed in the method according to the invention is a plant. In principle any possible plant can be used, i.e. a monocotyledonous plant or a dicotyledonous plant. It is preferable to use a plant which can be cultivated on an agriculturally meaningful scale and which allows to produce large amounts of biomass. Examples are grasses like *Lolium*, cereals like rye, wheat, barley, oat, millet, maize, other starch storing plants like potato or sugar storing plants like sugar cane or sugar beet. Conceivable is also the use of tobacco or of vegetable plants such as tomato, pepper, cucumber, egg plant etc. Another possibility is the use of oil storing plants such as rape seed, olives etc. Also conceivable is the use of trees, in particular fast growing trees such as eucalyptus, poplar or rubber tree (*Hevea brasiliensis*). Particularly preferred is the use of plants which naturally produce crotonaldehyde, e.g. soybeans. Such plants are preferably further modified so as to be able to convert crotonaldehyde into crotyl alcohol.

In another embodiment, the method according to the invention is characterized by the conversion of a carbon source, such as glucose, into crotyl alcohol (preferably via crotonyl-CoA and crotonaldehyde) followed by the conversion of crotyl alcohol into butadiene.

In another embodiment, the method according to the invention comprises the production of butadiene from atmospheric $CO_2$ or from $CO_2$ artificially added to the culture medium. In this case the method is implemented in an organism which is able to carry out photosynthesis, such as for example microalgae.

As described above, it is possible to use in the method according to the invention a (micro)organism which is genetically modified so as to contain a nucleic acid molecule encoding at least one of the enzymes as described above in connection with alternatives A or B. Such a nucleic acid molecule encoding an enzyme as described above can be used alone or as part of a vector. The nucleic acid molecules can further comprise expression control sequences operably linked to the polynucleotide comprised in the nucleic acid molecule. The term "operatively linked" or "operably linked", as used throughout the present description, refers to a linkage between one or more expression control sequences and the coding region in the polynucleotide to be expressed in such a way that expression is achieved under conditions compatible with the expression control sequence.

Expression comprises transcription of the heterologous DNA sequence, preferably into a translatable mRNA. Regulatory elements ensuring expression in fungi as well as in bacteria, are well known to those skilled in the art. They encompass promoters, enhancers, termination signals, targeting signals and the like. Examples are given further below in connection with explanations concerning vectors.

Promoters for use in connection with the nucleic acid molecule may be homologous or heterologous with regard to its origin and/or with regard to the gene to be expressed. Suitable promoters are for instance promoters which lend themselves to constitutive expression. However, promoters which are only activated at a point in time determined by external influences can also be used. Artificial and/or chemically inducible promoters may be used in this context.

The vectors can further comprise expression control sequences operably linked to said polynucleotides contained in the vectors. These expression control sequences may be suited to ensure transcription and synthesis of a translatable RNA in bacteria or fungi.

In addition, it is possible to insert different mutations into the polynucleotides by methods usual in molecular biology (see for instance Sambrook and Russell (2001), Molecular Cloning: A Laboratory Manual, CSH Press, Cold Spring Harbor, N.Y., USA), leading to the synthesis of polypeptides possibly having modified biological properties. The introduction of point mutations is conceivable at positions at which a modification of the amino acid sequence for instance influences the biological activity or the regulation of the polypeptide.

Moreover, mutants possessing a modified substrate or product specificity can be prepared. Preferably, such mutants show an increased activity. Furthermore, the introduction of mutations into the polynucleotides encoding an enzyme as defined above allows the gene expression rate and/or the activity of the enzymes encoded by said polynucleotides to be optimized.

For genetically modifying bacteria or fungi, the polynucleotides encoding an enzyme as defined above or parts of these molecules can be introduced into plasmids which permit mutagenesis or sequence modification by recombination of DNA sequences. Standard methods (see Sambrook and Russell (2001), Molecular Cloning: A Laboratory Manual, CSH Press, Cold Spring Harbor, N.Y., USA) allow base exchanges to be performed or natural or synthetic sequences to be added. DNA fragments can be connected to each other by applying adapters and linkers to the fragments. Moreover, engineering measures which provide suitable restriction sites or remove surplus DNA or restriction sites can be used. In those cases, in which insertions, deletions or substitutions are possible, in vitro mutagenesis, "primer repair", restriction or ligation can be used. In general, a sequence analysis, restriction analysis and other methods of biochemistry and molecular biology are carried out as analysis methods.

The polynucleotide introduced into a (micro)organism is expressed so as to lead to the production of a polypeptide having any of the activities described above. An overview of different expression systems is for instance contained in Methods in Enzymology 153 (1987), 385-516, in Bitter et al. (Methods in Enzymology 153 (1987), 516-544) and in Sawers et al. (Applied Microbiology and Biotechnology 46 (1996), 1-9), Billman-Jacobe (Current Opinion in Biotechnology 7 (1996), 500-4), Hockney (Trends in Biotechnology 12 (1994), 456-463), Griffiths et al., (Methods in Molecular Biology 75 (1997), 427-440). An overview of yeast expression systems is for instance given by Hensing et al. (Antonie van Leuwenhoek 67 (1995), 261-279), Bussineau et al. (Developments in Biological Standardization 83 (1994), 13-19), Gellissen et al. (Antonie van Leuwenhoek 62 (1992), 79-93, Fleer (Current Opinion in Biotechnology 3 (1992), 486-496), Vedvick (Current Opinion in Biotechnology 2 (1991), 742-745) and Buckholz (Bio/Technology 9 (1991), 1067-1072).

Expression vectors have been widely described in the literature. As a rule, they contain not only a selection marker gene and a replication-origin ensuring replication in the host selected, but also a bacterial or viral promoter, and in most cases a termination signal for transcription. Between the promoter and the termination signal there is in general at least one restriction site or a polylinker which enables the insertion of a coding DNA sequence. The DNA sequence naturally controlling the transcription of the corresponding gene can be used as the promoter sequence, if it is active in the selected host organism. However, this sequence can also be exchanged for other promoter sequences. It is possible to use promoters ensuring constitutive expression of the gene and inducible promoters which permit a deliberate control of the expression of the gene. Bacterial and viral promoter sequences possessing these properties are described in detail in the literature. Regulatory sequences for the expression in microorganisms (for instance E. coli, S. cerevisiae) are sufficiently described in the literature. Promoters permitting a particularly high expression of a downstream sequence are for instance the T7 promoter (Studier et al., Methods in Enzymology 185 (1990), 60-89), lacUV5, trp, trp-lacUV5 (DeBoer et al., in Rodriguez and Chamberlin (Eds), Promoters, Structure and Function; Praeger, New York, (1982), 462-481; DeBoer et al., Proc. Natl. Acad. Sci. USA (1983), 21-25), Ip1, rac (Boros et al., Gene 42 (1986), 97-100). Inducible promoters are preferably used for the synthesis of polypeptides. These promoters often lead to higher polypeptide yields than do constitutive promoters. In order to obtain an optimum amount of polypeptide, a two-stage process is often used. First, the host cells are cultured under optimum conditions up to a relatively high cell density. In the second step, transcription is induced depending on the type of promoter used. In this regard, a tac promoter is particularly suitable which can be induced by lactose or IPTG (=isopropyl-β-D-thiogalactopyranoside) (deBoer et al., Proc. Natl. Acad. Sci. USA 80 (1983), 21-25). Termination signals for transcription are also described in the literature.

The transformation of the host cell with a polynucleotide or vector according to the invention can be carried out by standard methods, as for instance described in Sambrook and Russell (2001), Molecular Cloning: A Laboratory Manual, CSH Press, Cold Spring Harbor, N.Y., USA; Methods in Yeast Genetics, A Laboratory Course Manual, Cold Spring Harbor Laboratory Press, 1990. The host cell is cultured in nutrient media meeting the requirements of the particular host cell used, in particular in respect of the pH value, temperature, salt concentration, aeration, antibiotics, vitamins, trace elements etc.

The present invention also relates to an organism, preferably a microorganism, which is able to express the enzymes required for the conversion of crotyl alcohol into butadiene according to alternative A or B of the method of the invention (according to the first aspect) as described above and which is able to convert crotyl alcohol into butadiene.

Thus, the present invention also relates to a (micro)organism which expresses

A) (a) (i) a hydroxyethylthiazole kinase (EC 2.7.1.50); or
    (ii) a thiamine kinase (EC 2.7.1.89); and
  (b) (i) a terpene synthase, e.g. an isoprene synthase (EC 4.2.3.27); or
    (ii) an isopentenyl phosphate kinase and a terpene synthase, e.g. an isoprene synthase (EC 4.2.3.27); or B) (a) (i) a 2-amino-4-hydroxy-6-hydroxymethyldihydropteridine diphosphokinase (EC 2.7.6.3); or
    (ii) a thiamine diphosphokinase (EC 2.7.6.2); and
  (b) a terpene synthase, e.g. an isoprene synthase (EC 4.2.3.27), and which is capable of converting crotyl alcohol into butadiene. As regards preferred embodiments, the same applies as has been set forth above in connection with the method according to the invention.

As regards in particular the terpene synthase and the preferred embodiments of terpene synthases to be expressed by the (micro)organism, the same applies as has been set forth above in connection with the method according to the invention.

Thus, in one preferred embodiment the terpene synthase is
(a) an isoprene synthase (EC 4.2.3.27); or
(b) a myrcene/ocimene synthase (EC 4.2.3.15); or
(c) a farnesene synthase (EC 4.2.3.46 or EC 4.2.3.47); or
(d) a pinene synthase (EC 4.2.3.14); or
(e) a monoterpene synthase.

The present invention also relates to an organism, preferably a microorganism, which is able to express the enzymes required for the conversion of crotonyl-CoA into crotonaldehyde and/or crotyl alcohol as described in connection with the second aspect of the invention. Thus, the present invention also relates to a (mirco)organism which expresses
(i) a hydroxymethylglutaryl-CoA reductase (EC 1.1.1.34); and/or
(ii) an acetaldehyde dehydrogenase (EC 1.2.1.10); and/or
(iii) an alcohol dehydrogenase (EC 1.1.1.1); and/or
(iv) an aldehyde/alcohol dehydrogenase; and/or
(v) an acyl-CoA reductase; and/or
(vi) an aldo-keto reductase (AKR); and/or
(vii) an aldehyde reductase; and/or
(viii) a short-chain dehydrogenase/fatty acyl-CoA reductase
(ix) and which is capable of converting crotonyl-CoA into crotonaldehyde and/or crotyl alcohol.

The present invention also relates to an organism, preferably a microorganism, which is further able to express the enzymes required for the conversion of 3-hydroxybutyryl-CoA into crotonyl-CoA. Thus, the present invention also relates to a (mirco)organism which expresses a 3-hydroxybutyryl-CoA dehydratase (EC 4.2.1.55) and/or an enoyl-CoA hydratase (EC 4.2.1.17) and/or an enoyl-CoA hydratase 2 (EC 4.2.1.119) and/or a crotonyl-[acyl-carrier-protein] hydratase (EC 4.2.1.58) and which is capable of converting 3-hydroxybutyryl-CoA into crotonyl-CoA.

The present invention also relates to an organism, preferably a microorganism, which is further able to express the enzymes required for the conversion of acetoacetyl-CoA into 3-hydroxybutyryl-CoA. Thus, the present invention also relates to a (mirco)organism which further expresses an acetoacetyl-CoA reductase (EC 1.1.1.36) and which is capable of converting acetoacetyl-CoA into 3-hydroxybutyryl-CoA.

Finally, the present invention also relates to an organism, preferably a microorganism, which is further able to express the enzymes required for the enzymatic production of acetoacetyl-CoA. This production may be achieved by the conversion of acetyl-CoA into acetoacetyl-CoA or by the conversion of acetyl-CoA and malonyl-CoA into acetoacetyl-CoA. Thus, the present invention also relates to a (mirco) organism which further expresses an acetyl-CoA C-acetyltransferase (EC 2.3.1.9) and which is capable of converting acetyl-CoA into acetoacetyl-CoA and/or which further expresses a acetoacetyl-CoA synthase and which is capable of converting acetyl-CoA and malonyl-CoA into acetoacetyl-CoA.

In one embodiment an organism according to the present invention is a recombinant organism in the sense that it is genetically modified due to the introduction of at least one nucleic acid molecule encoding at least one of the above mentioned enzymes. Preferably such a nucleic acid molecule is heterologous with regard to the organism which means that it does not naturally occur in said organism.

The microorganism is preferably a bacterium, a yeast or a fungus. In another preferred embodiment the organism is a plant or non-human animal. As regards other preferred embodiments, the same applies as has been set forth above in connection with the method according to the invention.

In an embodiment according to the present invention in which an organism, preferably a microorganism, is employed which is capable of providing crotonyl-CoA, such a (micro) organism is advantageously further genetically modified so as to avoid diverting of the crotonyl-CoA into other pathways. It is known, for example, that crotonyl-CoA can be reduced by a variety of enzymes to lead to butyryl-CoA. These enzymes generally belong to the EC classification EC 1.3.1 and include acyl-CoA dehydrogenase (NADP+, EC 1.3.1.8), enoyl-[acyl-carrier-protein] reductase (NADH; EC 1.3.1.9), enoyl-[acyl-carrier-protein] reductase (NADPH; EC 1.3.1.10), cis-2-enoyl-CoA reductase (NADPH; EC 1.3.1.37) and trans-2-enoyl-CoA reductase (NADPH; EC 1.3.1.38). Thus, in one embodiment the organism is genetically modified so as to decrease the activity of enzymes which may lead to a reduction of crotonyl-CoA to butyryl-CoA and thus to a diversion of crotonyl-CoA into other pathways. Such a reduction of activity can be achieved by methods known to the person skilled in the art and include, for example, the decrease of the expression of the respective gene(s) coding for the respective enzyme(s) by known methods such as antisense approaches, siRNA approaches or the like. In case the respective enzyme activity is not necessary for survival of the microorganism, it can also be knocked out completely, e.g. by disrupting the gene or completely deleting the gene.

The present invention also relates to a composition comprising
A) (a) (i) a hydroxyethylthiazole kinase (EC 2.7.1.50); or
    (ii) a thiamine kinase (EC 2.7.1.89); and
  (b) (i) a terpene synthase, e.g. an isoprene synthase (EC 4.2.3.27); or
    (ii) an isopentenyl phosphate kinase and a terpene synthase, e.g. an isoprene synthase (EC 4.2.3.27); or
B) (a) (i) a 2-amino-4-hydroxy-6-hydroxymethyldihydropteridine diphosphokinase EC 2.7.6.3); or
    (ii) a thiamine diphosphokinase (EC 2.7.6.2); and
  (b) a terpene synthase, e.g. an isoprene synthase (EC 4.2.3.27).

Such a composition may also comprise crotyl alcohol. As regards preferred embodiments, the same applies as has been set forth above in connection with the method according to the invention.

As regards in particular the terpene synthase and the preferred embodiments of terpene synthases to be expressed by the (micro)organism, the same applies as has been set forth above in connection with the method according to the invention.

Thus, in one preferred embodiment the terpene synthase is
(f) an isoprene synthase (EC 4.2.3.27); or
(g) a myrcene/ocimene synthase (EC 4.2.3.15); or
(h) a farnesene synthase (EC 4.2.3.46 or EC 4.2.3.47); or
(i) a pinene synthase (EC 4.2.3.14); or
(i) a monoterpene synthase.

The present invention also relates to a composition comprising
(i) a hydroxymethylglutaryl-CoA reductase (EC 1.1.1.34); and/or
(ii) an acetaldehyde dehydrogenase (EC 1.2.1.10); and/or
(iii) an alcohol dehydrogenase (EC 1.1.1.1); and/or
(iv) an aldehyde/alcohol dehydrogenase; and/or
(v) an acyl-CoA reductase; and/or
(vi) an aldo-keto reductase (AKR); and/or
(vii) an aldehyde reductase; and/or
(viii) a short-chain dehydrogenase/fatty acyl-CoA reductase.

Moreover, the present invention also relates to such a composition which further comprises a 3-hydroxybutyryl-CoA dehydratase (EC 4.2.1.55) and/or an enoyl-CoA hydratase (EC 4.2.1.17) and/or an enoyl-CoA hydratase 2 (EC 4.2.1.119) and/or a crotonyl-[acyl-carrier-protein] hydratase (EC 4.2.1.58). The present invention also relates to a composition which also comprises an acetoacetyl-CoA reductase (EC 1.1.1.36). Finally, the present invention also relates to a composition which also comprises an acetyl-CoA C-acetyltransferase (EC 2.3.1.9) or an acetoacetyl-CoA synthase.

The present invention also relates to the use of a combination of enzymes comprising:
A) (a) (i) a hydroxyethylthiazole kinase (EC 2.7.1.50); or
    (ii) a thiamine kinase (EC 2.7.1.89); and
  (b) (i) a terpene synthase, e.g. an isoprene synthase (EC 4.2.3.27); or
    (ii) an isopentenyl phosphate kinase and a terpene synthase, e.g. an isoprene synthase (EC 4.2.3.27); or
B) (a) (i) a 2-amino-4-hydroxy-6-hydroxymethyldihydropteridine diphosphokinase EC 2.7.6.3); or
    (ii) a thiamine diphosphokinase (EC 2.7.6.2); and
  (b) a terpene synthase, e.g. an isoprene synthase (EC 4.2.3.27);
for the production of butadiene from crotyl alcohol. As regards preferred embodiments, the same applies as has been set forth above in connection with the method according to the invention.

As regards in particular the terpene synthase and the preferred embodiments of terpene synthases to be expressed by the (micro)organism, the same applies as has been set forth above in connection with the method according to the invention.

Thus, in one preferred embodiment the terpene synthase is
(k) an isoprene synthase (EC 4.2.3.27); or
(l) a myrcene/ocimene synthase (EC 4.2.3.15); or
(m) a farnesene synthase (EC 4.2.3.46 or EC 4.2.3.47); or
(n) a pinene synthase (EC 4.2.3.14); or
(o) a monoterpene synthase.

The present invention also relates to the use of
(i) a hydroxymethylglutaryl-CoA reductase (EC 1.1.1.34); and/or
(ii) an acetaldehyde dehydrogenase (EC 1.2.1.10); and/or
(iii) an alcohol dehydrogenase (EC 1.1.1.1); and/or
(iv) an aldehyde/alcohol dehydrogenase; and/or
(v) an acyl-CoA reductase; and/or
(vi) an aldo-keto reductase (AKR); and/or
(vii) an aldehyde reductase; and/or
(viii) a short-chain dehydrogenase/fatty acyl-CoA reductase
for the conversion of crotonyl-CoA into crotonaldehyde and/or crotyl alcohol.

Furthermore the present invention also relates to the use of a combination of enzymes comprising
(a) an acetoacetyl-CoA reductase (EC 1.1.1.36); and
(b) (i) a 3-hydroxybutyryl-CoA dehydratase (EC 4.2.1.55); and or
    (ii) an enoyl-CoA hydratase (EC 4.2.1.17); and/or
    (iii) an enoyl-CoA hydratase 2 (EC 4.2.1.119); and/or
    (iv) a crotonyl-[acyl-carrier-protein] hydratase (EC 4.2.1.58)
for the production of crotonyl-CoA from acetoacetyl-CoA.

The present invention also relates to the use of a combination of enzymes comprising
(a) (i) an acetyl-CoA C-acetyltransferase (EC 2.3.1.9) and/or
    (ii) an acetoacetyl-CoA synthase; and
(b) an acetoacetyl-CoA reductase (EC 1.1.1.36);
(c) (i) a 3-hydroxybutyryl-CoA dehydratase (EC 4.2.1.55); and/or
    (ii) an enoyl-CoA hydratase (EC 4.2.1.17); and/or
    (iii) an enoyl-CoA hydratase 2 (EC 4.2.1.119); and/or
    (iv) a crotonyl-[acyl-carrier-protein] hydratase (EC 4.2.1.58)
for the production of crotonyl-CoA from acetyl-CoA.

Figure 2:
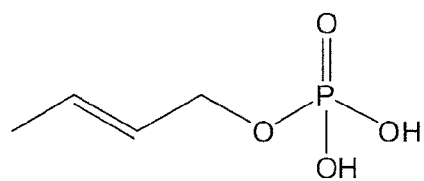
Figure 2:
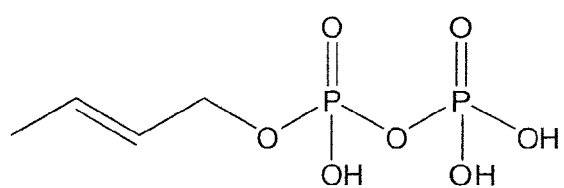
Figure 3:
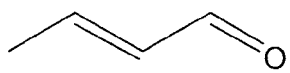

FIG. 1 shows the chemical structure of crotyl alcohol.
FIG. 2 shows the chemical structure of crotyl phosphate. and crotyl diphosphate
FIG. 3 shows the chemical structure of crotonaldehyde.
FIG. 4 shows the chemical structure of butadiene.

Figure 5:
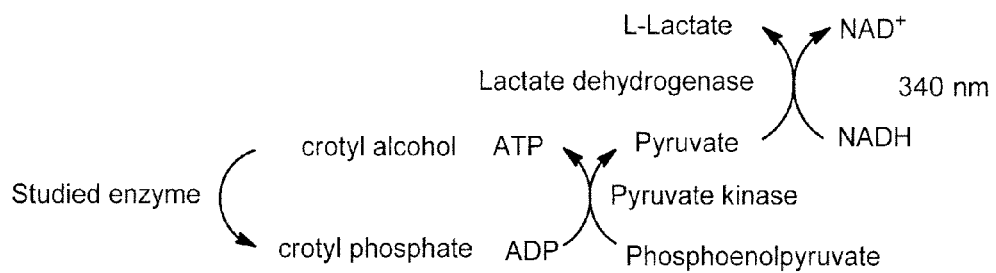
Figure 6:
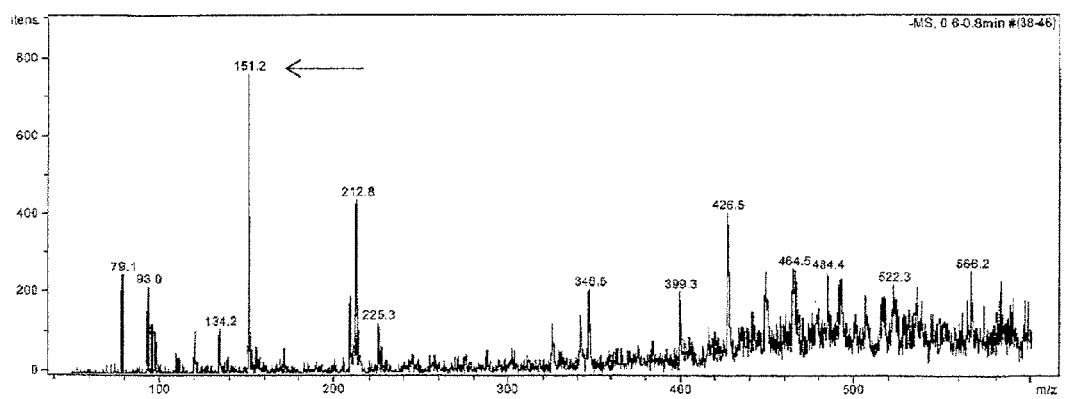
Figure 7:
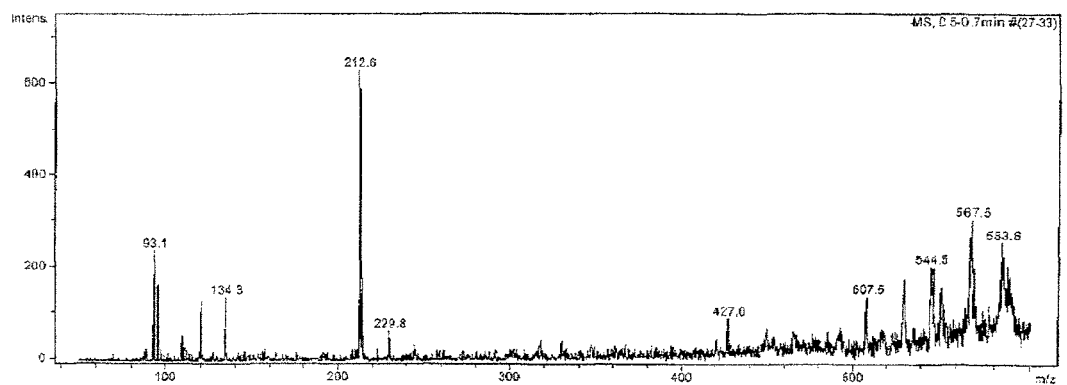
Figure 8:
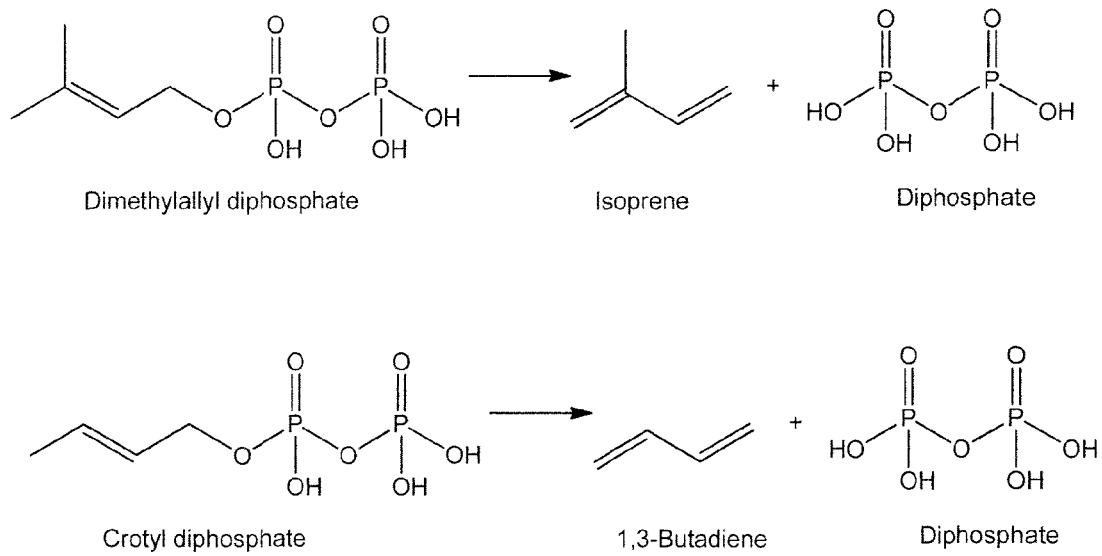
Figure 9:
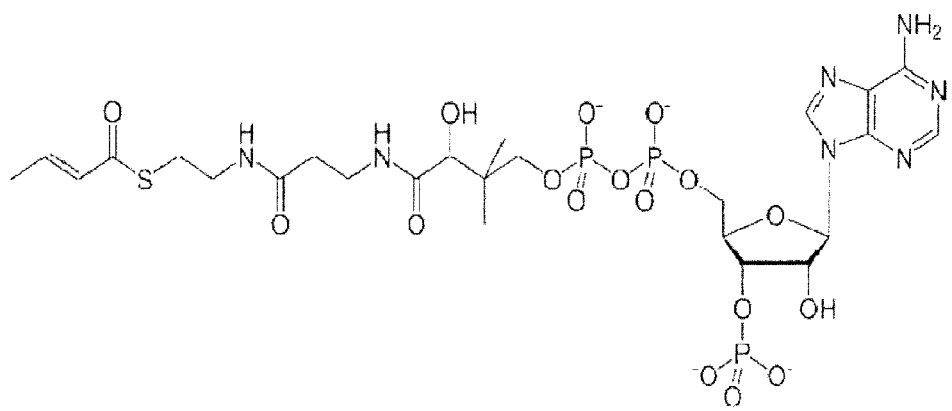
Figure 14:
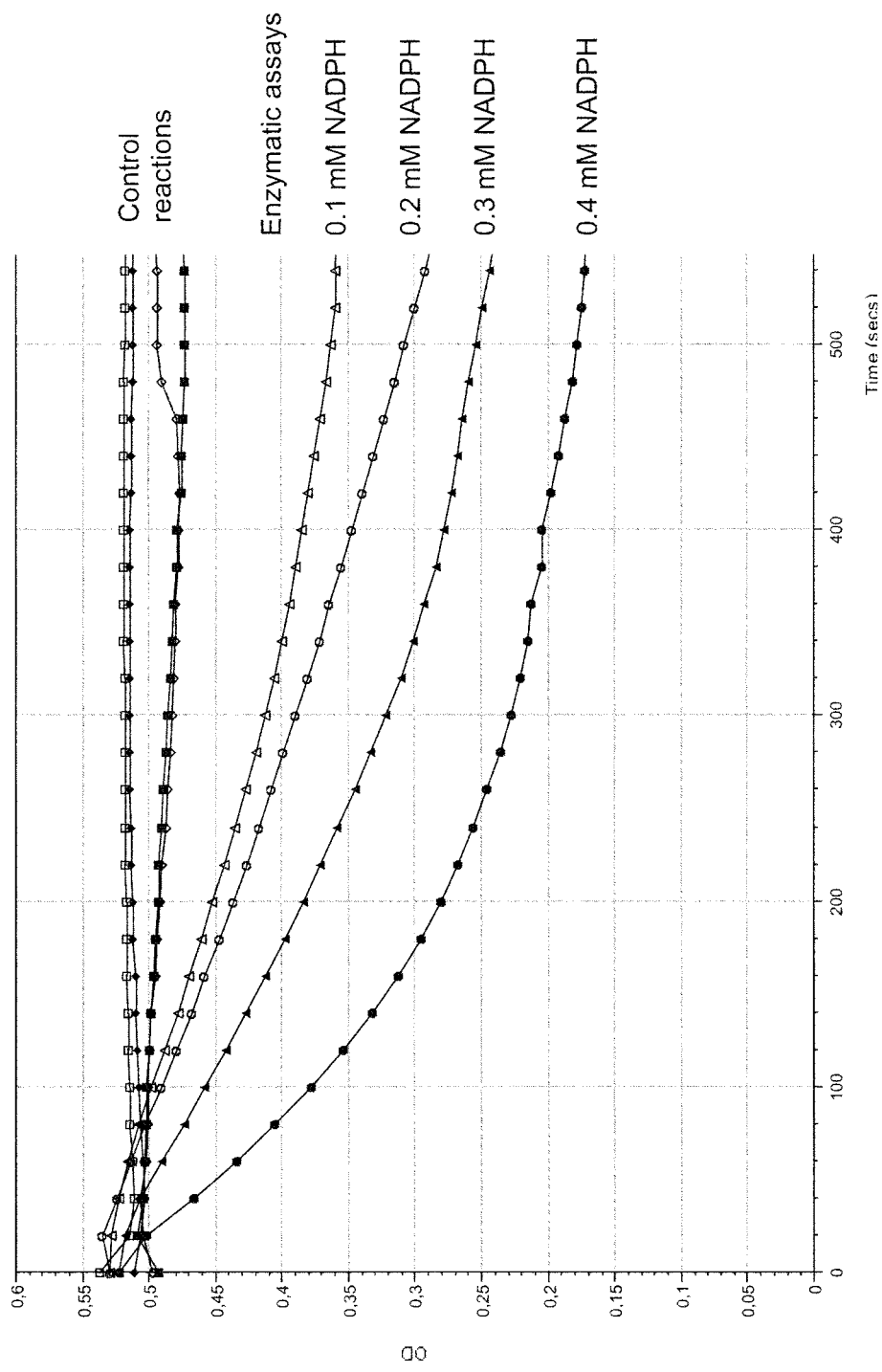
Figure 15:
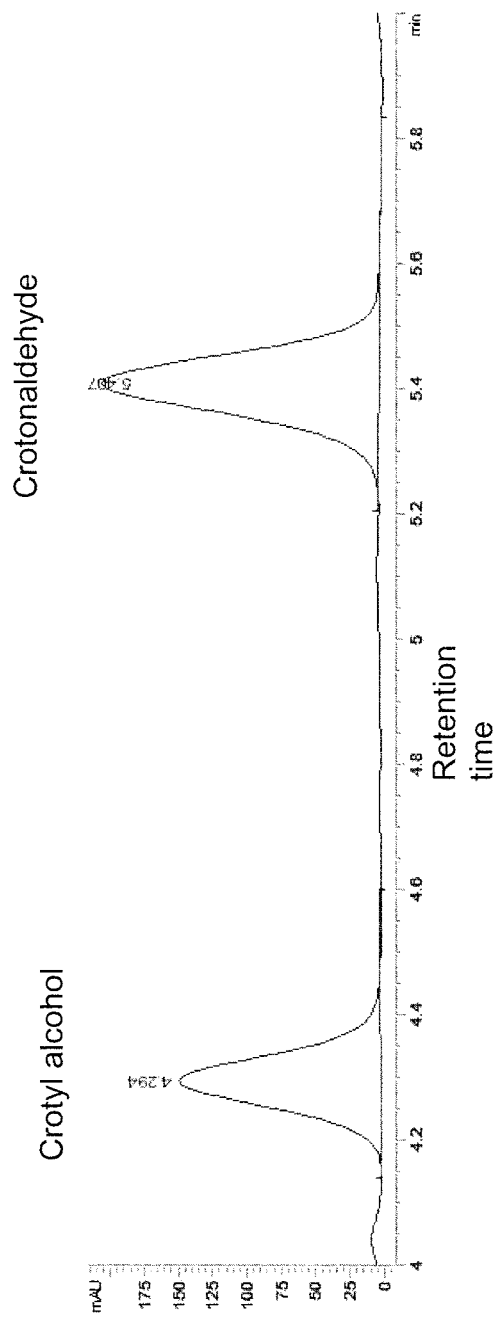

FIG. 5 shows a scheme of the ADP quantification assay, monitoring NADH consumption by the decrease of absorbance at 340 nm.
FIG. 6 shows a mass spectrum of an enzymatic assay with hydroxyethylthiazole kinase from $E.\ coli$.
FIG. 7 shows a mass spectrum of a control assay without enzyme.
FIG. 8 shows a comparison between dimethylallyl diphosphate and crotyl diphosphate and their conversion into isoprene (2-methyl-buta-1,3-diene) and butadiene, respectively.
FIG. 9 shows the formula of crotonyl-Coenzyme A
FIG. 10 shows the MS spectrum of the trans crotyl monophosphate phosphorylation reaction catalyzed by isopentenyl monophosphate kinase from $M.\ jannaschii$ (a) and of a control assay without enzyme (b).
FIG. 11 shows 1,3-butadiene production from trans crotyl monophosphate catalyzed by terpene synthases.
FIG. 12 shows the mass spectrum of commercial 1,3-butadiene (a) and 1,3-butadiene produced from trans crotyl monophosphate in an enzymatic reaction catalyzed by monoterpene synthase from $E.\ globulus$ (b).
FIG. 13 shows 1,3-butadiene production from trans crotyl diphosphate catalyzed by terpene synthases.
FIG. 14 shows a time courses of NADPH oxidation in crotonyl-CoA reduction assay with reductase from $Hahella\ chejuensis$ and varying concentrations of NADPH.
FIG. 15 shows a chromatogram of the crotonyl-CoA reduction reaction catalyzed by acyl-CoA reductase from $H.\ chejuensis$.

Other aspects and advantages of the invention will be described in the following examples, which are given for purposes of illustration and not by way of limitation.

EXAMPLES

Example 1

Cloning, Expression and Purification of Enzymes

Cloning, Bacterial Cultures and Expression of Proteins
The genes encoding studied enzymes were cloned in pET 25b vector (Novagen). A stretch of 6 histidine codons was inserted after the methionine initiation codon to provide an affinity tag for purification. Competent $E.\ coli$ BL21(DE3) cells (Novagen) were transformed with these vectors according to the heat shock procedure. The transformed cells were grown with shaking (160 rpm) on ZYM-5052 auto-induction medium (Studier F W, $Prot.\ Exp.\ Pur.$ 41 (2005), 207-234) for 6 h at 37° C. and protein expression was continued at 28° C. or 20° C. overnight (approximately 16 h). The cells were collected by centrifugation at 4° C., 10,000 rpm for 20 min and the pellets were frozen at −80° C.

Protein Purification and Concentration
The pellets from 200 ml of culture cells were thawed on ice and resuspended in 5 ml of $Na_2HPO_4$ pH 8 containing 300 mM NaCl, 5 mM $MgCl_2$ and 1 mM DTT. Twenty microliters of lysonase (Novagen) were added. Cells were incubated 10 minutes at room temperature and then returned to ice for 20 minutes. Cell lysis was completed by sonication for 3×15 seconds. The bacterial extracts were then clarified by centrifugation at 4° C., 10,000 rpm for 20 min. The clarified bacterial lysates were loaded on PROTINO-1000 Ni-TED column (Macherey-Nagel) allowing adsorption of 6-His tagged proteins. Columns were washed and the enzymes of interest were eluted with 4 ml of 50 mM $Na_2HPO_4$ pH 8 containing 300 mM NaCl, 5 mM $MgCl_2$, 1 mM DTT, 250 mM imidazole. Eluates were then concentrated and desalted on Amicon Ultra-4 10 kDa filter unit (Millipore) and resuspended in 0.25 ml 50 mM Tris-HCl pH 7.4 containing 0.5 mM DTT and 5 mM MgCl$_2$. Protein concentrations were quantified according to the Bradford method. The purity of proteins thus purified varied from 50% to 90%.

Example 2

Screening for Crotyl Alcohol Phosphorylation Activity

The release of ADP that is associated with crotyl alcohol phosphorylation was quantified using the pyruvate kinase/lactate dehydrogenase coupled assay (FIG. 5). The purified 4-methyl-5-(2-hydroxyethyl)thiazole kinases from *Escherichia coli* (SEQ ID NO:2), *Bacillus subtilis* (SEQ ID NO:1), *Rhizobium leguminosarum* (SEQ ID NO:3) were evaluated for their ability to phosphorylate crotyl alcohol releasing ADP. The studied enzymatic reaction was carried out under the following conditions at 37° C.:
50 mM Tris-HCl pH 7.5
10 mM MgCl$_2$
100 mM KCl
5 mM ATP
0.4 mM NADH
1 mM Phosphoenolpyruvate
3 U/ml Lactate dehydrogenase
1.5 U/ml Pyruvate kinase
50 mM crotyl alcohol, mixture cis and trans
The pH was adjusted to 7.5

Each assay was started by addition of a particular enzyme at a concentration 0.05 mg/ml and the disappearance of NADH was monitored by following the absorbance at 340 nM.

Assays with hydroxyethylthiazole kinase from the *E. coli* and *Rh. leguminosarum* gave rise to a reproducible and significant increase in ADP production in the presence of crotyl alcohol (Table 1). Mass spectrometry was then used to verify the formation of crotyl monophosphate in the assay with the *E. coli* enzyme.

TABLE 1

| 4-methyl-5-(2-hydroxyethyl) thiazole kinase | Activity, micromole/ min · mg protein |
| --- | --- |
| *E. coli* | 0.220 |
| *Rh. leguminosarum* | 0.087 |
| *B. subtilis* | 0.014 |

Example 3

Mass Spectrometry Analysis of the Crotyl Alcohol Phosphorylation Reaction

The desired enzymatic reactions were carried out under the following conditions:
50 mM Tris-HCl pH7.5
10 mM MgCl2
50 mM cis or trans crotyl alcohol
20 mM ATP
0.1 mg/ml purified hydroxythiazole kinase from *E. coli* (SEQ ID NO:2)

The control reactions without enzyme, without substrate and without ATP were run in parallel. The assays were incubated overnight without shaking at 37° C. Typically, an aliquot of 2001 reaction was removed, centrifuged and the supernatant was transferred into a clean vial. The MS spectra were obtained on an ion trap mass spectrometer (Esquire 3000, Bruker) in negative ion mode by direct injection of the sample using a syringe pump operated at a flow rate of 2 ml/h. The presence of crotyl monophosphate was evaluated. MS analysis showed an [M-H]– ion at m/z 151, corresponding to crotyl monophosphate, from the enzymatic sample but not from the controls (FIGS. 6 and 7).

Example 4

Screening for 1,3-Butadiene Production from Crotyl Monophosphate Using Purified Isoprene Synthases Crotyl monophosphate is synthesized upon request by a company specialized in custom synthesis (Syntheval, France).

The enzymatic assays are carried out under the following conditions at 37° C.:
50 mM Tris-HCl pH7.5
1 to 200 mM cis or trans crotyl monophosphate
1 mM DTT
1 to 20 mM MgCl$_2$
1 to 5 mg/ml isoprene synthase The enzyme-free control reaction is carried out in parallel. The enzymatic mixture is incubated at 37° C. for 72 h in a sealed vial (Interchim).

Volatile compounds in the headspace of the reaction mixture are collected using a gas syringe equipped with an anti-backup mechanism and are directly injected into a GC-430 gas chromatograph (Brucker) equipped with an FID detector and a GAS-PRO column (Agilent). The enzymatic reaction product is identified by direct comparison with standard 1,3-butadiene (Sigma).

The identity of the gas is further confirmed in GC/MS analyses.

Example 5

Screening for Crotyl Monophosphate Phosphorylation Activity

Sequences of isopentenyl monophosphate kinases inferred from the genomes of several members of the Archaea, in particular *Methanothermobacter* (SEQ ID NO:5), *Methanocaldococcus* (SEQ ID NO:6) and *Thermoplasma* (SEQ ID NO:4) genus, are generated by oligonucleotide concatenation to fit the codon usage of *E. coli*. A stretch of 6 histidine codons is inserted after the methionine initiation codon to provide an affinity tag for purification. The genes thus synthesized are cloned in a pET25b expression vector and the proteins are produced according to the protocol described in Example 1. The enzymes are then assayed using the method described in Example 2 with crotyl monophosphate concentrations varying from 0 to 50 mM. The release of ADP that is associated with crotyl monophosphate phosphorylation is quantified using the pyruvate kinase/lactate dehydrogenase coupled assay. Each assay is started by addition of particular enzyme (at a final concentration from 0.05 mg/ml to 1 mg/ml) and the disappearance of NADH is monitored by following the absorbance at 340 nM.

Example 6

Mass Spectrometry Analysis of the Crotyl Monophosphate Phosphorylation Reaction

Enzymatic assays are run in 50 mM Tris-HCl pH 7.5, contained 5 mM MgCl$_2$, 20 mM ATP, 2 mM β-mercaptoethanol and crotyl monophosphate varying in the range from 0 to 50 mM in a final volume of 0.25 ml. The reactions are initiated with the addition of purified isoprenol monophosphate kinase and incubated overnight at 37-55° C. The control reactions contain no enzyme. Following incubation samples are processed by mass spectrometry analysis. An aliquot of 200 μl reaction is removed, centrifuged and the supernatant is transferred to a clean vial. The MS spectra are obtained on ion trapp mass spectrometer (Esquire 3000, Bruker) in negative ion mode by direct injection of sample using a syringe pump operated at a flow rate of 2 ml/h.

Example 7

Screening for 1,3-Butadiene Production from Crotyl Diphosphate Using Purified Isoprene Synthases Crotyl diphosphate is synthesized upon request by a company specialized in custom synthesis, Syntheval (France).
The enzymatic assays are carried out under the following conditions at 37° C.:
50 mM Tris-HCl pH7.5
1 to 200 mM cis or trans crotyl diphosphate
1 mM DTT
1 to 20 mM MgCl$_2$
1 to 5 mg/ml isoprene synthase
The enzyme-free control reaction is carried out in parallel. The enzymatic mixture is incubated at 37° C. for 72 h in a sealed vial (Interchim).
Volatile compounds in the headspace of the reaction mixture are collected using a gas syringe equipped with an antibackup mechanism and are directly injected into a GC-430 gas chromatograph (Brucker) equipped with an FID detector and a GAS-PRO column (Agilent). The enzymatic reaction product is identified by direct comparison with standard 1,3-butadiene (Sigma).
The identity of the gas is further confirmed in GC/MS analyses.

Example 8

Screening of Hydroxymethylglutaryl-CoA (Hmg-CoA) Reductases Using Crotonyl-CoA as a Substrate Sequences of hydroxymethylglutaryl-CoA reductases inferred from the genomes of prokaryotic and eukaryotic organisms are generated to fit the codon usage of E. coli. A stretch of 6 histidine codons is inserted after the methionine initiation codon to provide an affinity tag for purification. The genes thus synthesized are cloned in a pET25b expression vector and the proteins are produced according to the protocol described in Example 1. The reductase activity of the purified enzymes using crotonyl-CoA as a substrate is then determined by measuring the initial decrease in absorbance at 340 nm due to the NADPH oxidation. The standard assay is performed at pH 7.5, 50 mM phosphate buffer, containing 10 mM dithiothreitol, 0.1 mM NADPH and crotonyl-CoA at concentration varying from 0 to 10 mM.

Example 9

Kinetic Parameters of Crotyl Alcohol Phosphorylation

Kinetic parameters of crotyl alcohol phosphorylation were determined using the spectrophotometric assay described in Example 2. Kinetic parameters obtained for purified 4-methyl-5-(2-hydroxyethyl)thiazole kinase from E. coli are presented in Table 2.

TABLE 2

| Substrate | Kinetic parameters | |
|---|---|---|
| | $K_m$, mM | $k_{cat}$, $s^{-1}$ |
| Cis crotyl alcohol | 13.6 | 0.19 |
| Trans crotyl alcohol | 30 | 0.11 |

Example 10

Mass Spectrometry Analysis of the Crotyl Monophosphate Phosphorylation Reaction

Figure 10A:
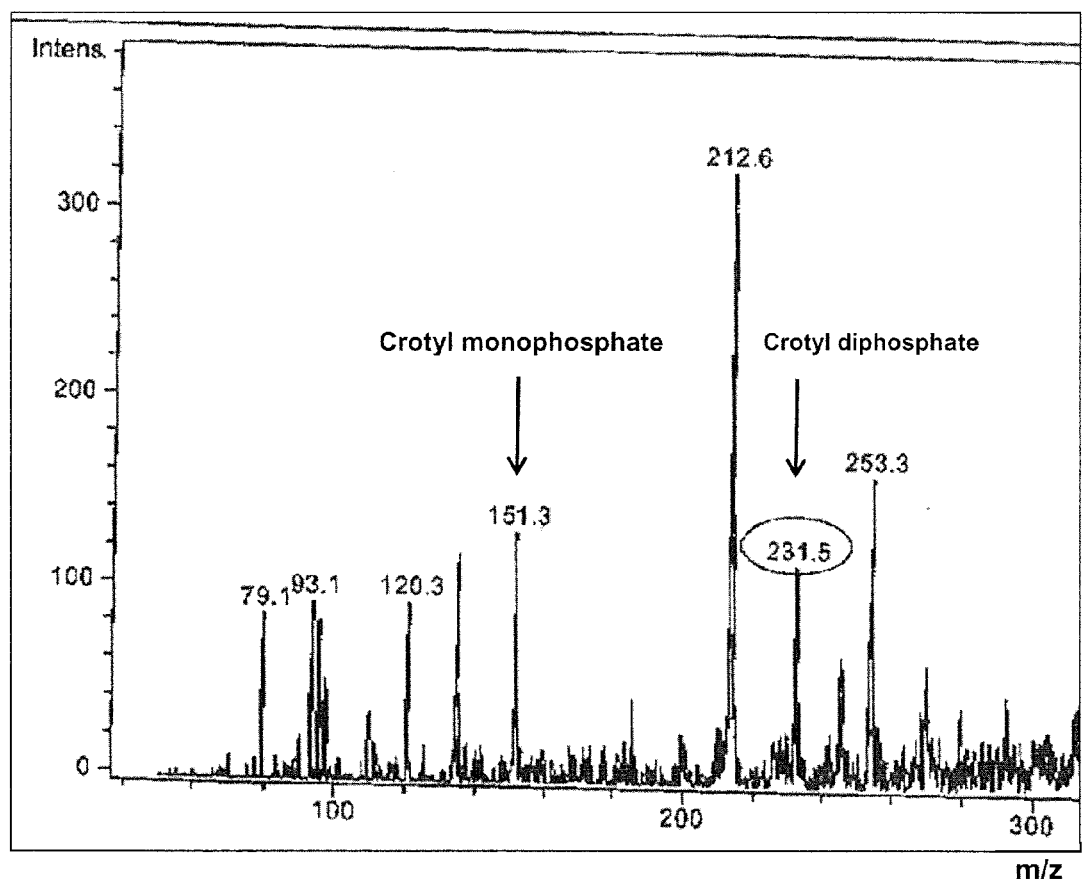
Figure 10B:
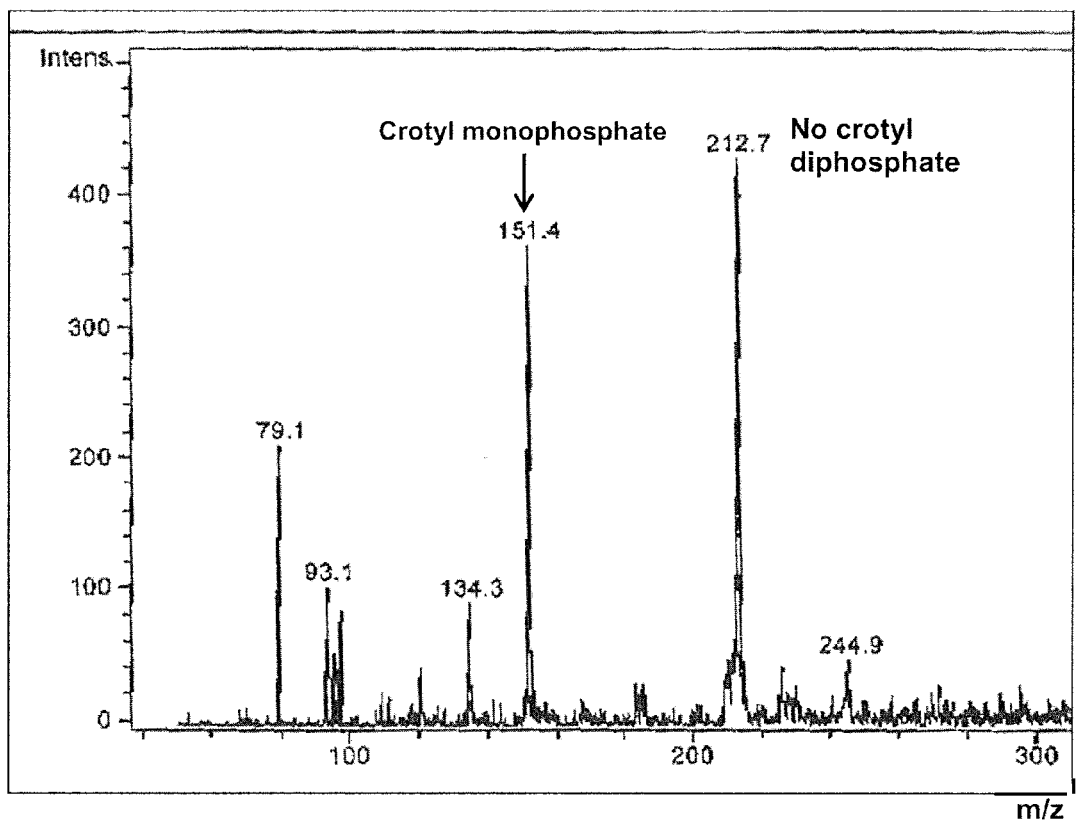

The enzymatic reactions were carried out under the following conditions:
50 mM Tris-HCl pH 7.5
10 mM MgCl$_2$
100 mM KCl
50 mM trans crotyl monophosphate
20 mM ATP
0.1 mg/ml purified isopentenyl monophosphate kinase
Control assays were performed in which either no enzyme was added, or no substrate was added. The assays were incubated overnight without shaking at 37° C. Typically, an aliquot of 200 μl reaction was removed, centrifuged and the supernatant was transferred into a clean vial. The MS spectra were obtained on ion trap mass spectrometer (Esquire 3000, Bruker) in negative ion mode by direct injection of sample using a syringe pump operated at a flow rate of 2 ml/h. The presence of crotyl diphosphate was evaluated. MS analysis showed an [M-H]$^-$ ion at m/z 231.5, corresponding to crotyl diphosphate, from the enzymatic samples but not from the controls. Examples of mass spectrums of enzymatic assay with isopentenyl monophosphate kinase from M. jannaschii and control assay without enzyme are shown in FIGS. 10a and 10b.

Example 11

Kinetic Parameters of the Crotyl Monophosphate Phosphorylation Reaction

Cis crotyl monophosphate and trans crotyl monophosphate were synthesized upon request by a company specialized in custom synthesis (Syntheval, France). Kinetic parameters for the phosphorylation of these substrates were determined using the spectrophotometric assay described in Example 2. Kinetic parameters obtained with purified isopentenyl monophosphate kinases from different members of the Archaea kingdom are presented in Table 3 (cis crotyl monophosphate as a substrate) and Table 4 (trans crotyl monophosphate as a substrate).

TABLE 3

| Isopentenyl monophosphate kinase | Kinetic parameters | |
|---|---|---|
| | $K_m$, mM | $k_{cat}$, $s^{-1}$ |
| Methanocaldococcus jannaschii | 0.20 | 3.4 |

TABLE 3-continued

| Isopentenyl monophosphate kinase | Kinetic parameters | |
|---|---|---|
| | $K_m$, mM | $k_{cat}$, $s^{-1}$ |
| Methanothermobacter thermautotrophicus | 0.94 | 5.7 |
| Thermoplasma acidophilum | 0.61 | 1.8 |

TABLE 4

| | Kinetic parameters | |
|---|---|---|
| Enzyme | $K_m$, mM | $k_{cat}$, $s^{-1}$ |
| Methanocaldococcus jannaschii | 0.49 | 3.0 |
| Methanothermobacter thermautotrophicus | 0.45 | 8.7 |
| Thermoplasma acidophilum | 1 | 2.2 |

Example 12

Enzyme Catalyzed Production of 1,3-Butadiene from Trans Crotyl Monophosphate with Purified Terpene Synthases The enzymatic assays were carried out under the following conditions at 37° C.:
50 mM Tris-HCl pH 7.5
25 mM trans crotyl monophosphate
2 mM DTT
50 mM MgCl$_2$
50 mM KCl
2 mg of the purified terpene synthase was added to 0.5 ml of reaction mixture. An enzyme-free control reaction was carried out in parallel. Assays were incubated at 37° C. for 24 h in a sealed vial of 1.5 ml (Interchim) with shaking.

One ml of the gaseous phase was then collected and directly injected into a Varian GC-430 gas chromatograph equipped with a flame ionization detector (FID). Nitrogen was used as carrier gas with a flow rate of 1.5 ml/min. Volatile compounds were chromatographically separated on RT-Alumina Bond/Na$_2$SO$_4$ column (Restek) using an isothermal mode at 130° C. The enzymatic reaction product was identified by direct comparison with 1,3-butadiene standard (Sigma). Several terpene synthases were shown to catalyze butadiene production from trans crotyl monophosphate (FIG. 11).

Figure 12A:
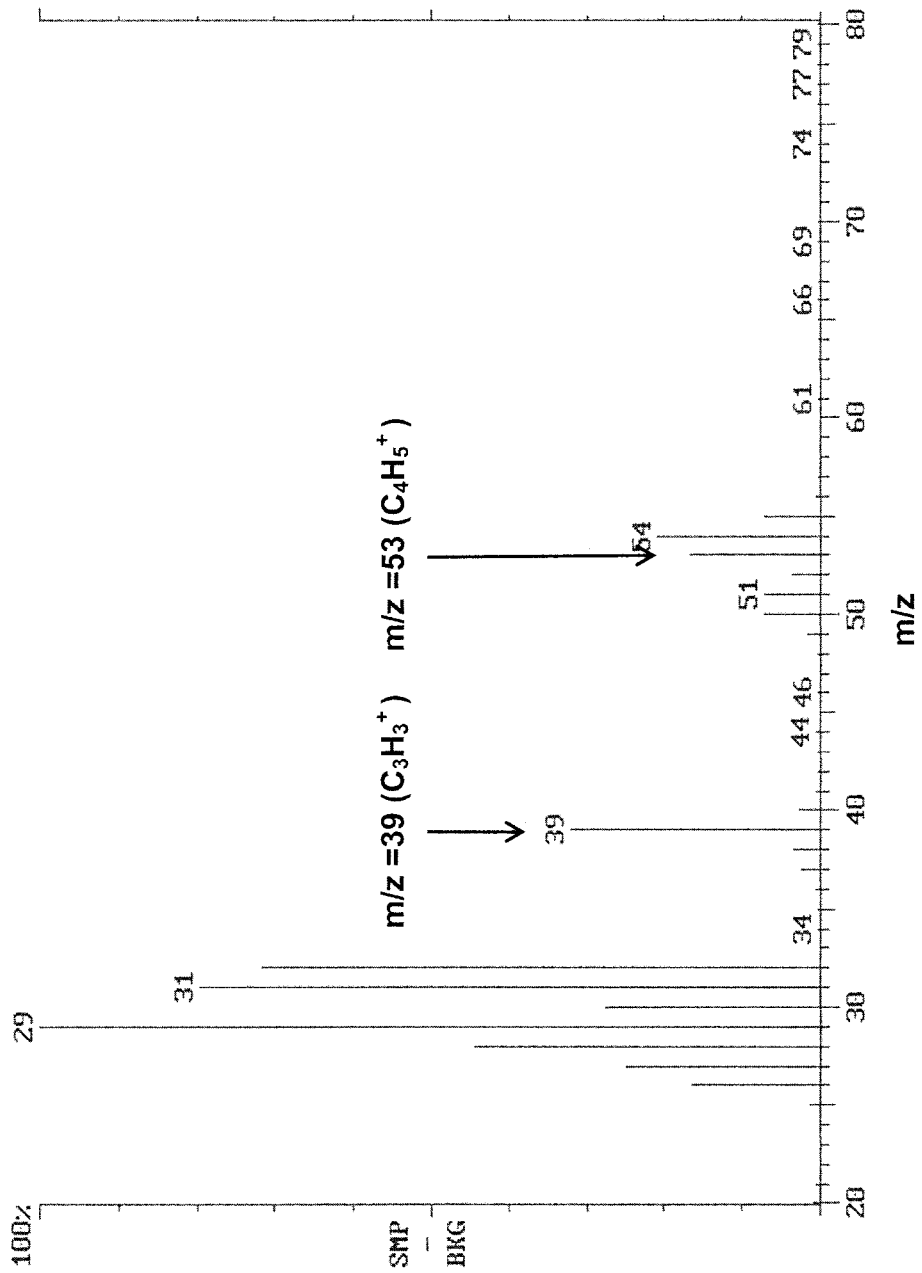
Figure 12B:
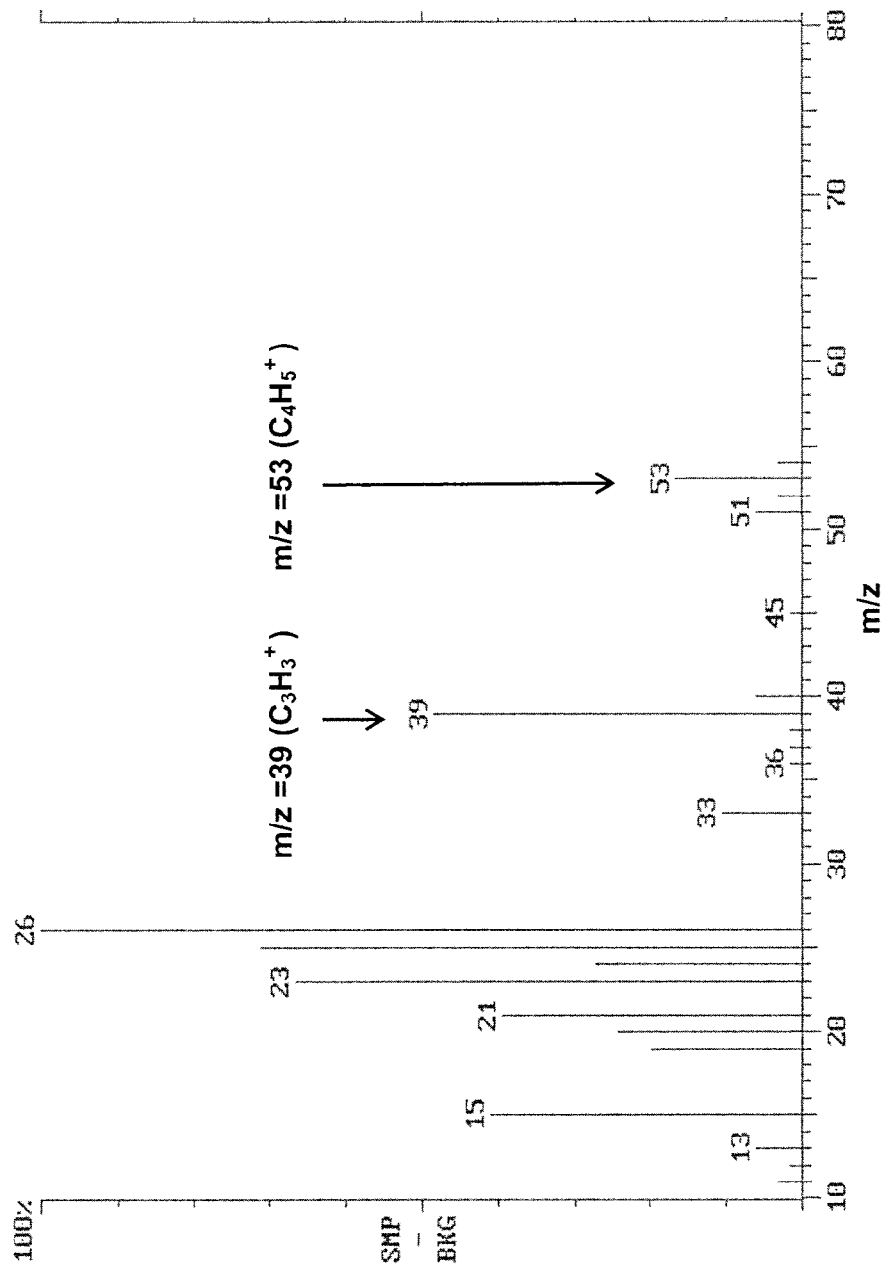

Gas chromatography-mass spectrometry was then used to confirm the identity of the product detected by GC/FID. Assay with E. globulus enzyme (SEQ ID NO: 8) was analyzed on a Varian 3400Cx gas chromatograph equipped with Varian Saturn 3 mass selective detector. A mass spectrum of 1,3-butadiene obtained by enzymatic conversion of trans crotyl monophosphate was similar to that of commercial 1,3-butadiene (FIGS. 12a and 12b).

Example 13

Kinetic Parameters of Enzyme Catalyzed Production of 1,3-Butadiene from Trans Crotyl Monophosphate The kinetic parameters of enzyme catalyzed production of 1,3-butadiene from trans crotyl monophosphate were measured under the following conditions:
50 mM Tris-HCl pH 7.5
20 mM MgCl$_2$
20 mM KCl
2 mM DTT
0-25 mM trans crotyl monophosphate The reaction was initiated by addition of 0.25 mg of purified monoterpene synthase from Eucalyptus globulus to 0.5 ml of reaction mixture. An enzyme-free control reaction was carried out in parallel. Assays were incubated at 37° C. for 0.5-4 h in a sealed vial of 1.5 ml (Interchim) with shaking.

1,3-butadiene production was analyzed using the GC/FID procedure described in Example 12. Monoterpene synthase from E. globulus was found to have a $K_M$ value of 6 mM and a $k_{cat}$ of at least $0.2 \times 10^{-5}$ sec$^{-1}$.

Example 14

Enzyme Catalyzed Production of 1,3-Butadiene from Trans Crotyl Diphosphate with Purified Terpene Synthases The enzymatic assays were carried out under the following conditions at 37° C.:
50 mM Tris-HCl pH 7.5
25 mM trans crotyl diphosphate
2 mM DTT
50 mM MgCl$_2$
50 mM KCl
2 mg of the purified terpene synthase was added to 0.5 ml of reaction mixture. An enzyme-free control reaction was carried out in parallel. Assays were incubated at 37° C. for 24 h in a sealed vial of 1.5 ml (Interchim) with shaking.

One ml of the gaseous phase was then collected and directly injected into a Varian GC-430 gas chromatograph equipped with a flame ionization detector (FID). Nitrogen was used as carrier gas with a flow rate of 1.5 ml/min. Volatile compounds were chromatographically separated on RT-Alumina Bond/Na$_2$SO$_4$ column (Restek) using an isothermal mode at 130° C. The enzymatic reaction product was identified by direct comparison with 1,3-butadiene standard (Sigma). Several terpene synthases were shown to catalyze butadiene production from trans crotyl diphosphate (FIG. 13).

Example 15

Kinetic Parameters of Enzyme Catalyzed Production of 1,3-Butadiene from Trans Crotyl Diphosphate The kinetic parameters of enzyme catalyzed production of 1,3-butadiene from trans crotyl monophosphate were measured under the following conditions:
50 mM Tris-HCl pH 7.5
20 mM MgCl$_2$
20 mM KCl
2 mM DTT
0-25 mM trans crotyl diphosphate The reaction was initiated by addition of 0.25 mg of purified monoterpene synthase from Eucalyptus globulus to 0.5 ml of reaction mixture. An enzyme-free control reaction was carried out in parallel. Assays were incubated at 37° C. for 0.5-4 h in a sealed vial of 1.5 ml (Interchim) with shaking.

1,3-butadiene production was analyzed using the GC/FID procedure described in Example 12. Monoterpene synthase from E. globulus was found to have a $K_M$ value of 7 mM and a $k_{cat}$ of at least $0.3 \times 10^{-4}$ sec$^{-1}$.

Example 16

Screening of Short-Chain Dehydrogenases/Reductases with Crotonyl-CoA as Substrate Sequences of short-chain dehydrogenases/reductases inferred from the genomes of prokaryotic organisms were generated by oligonucleotide concatenation to fit the codon usage of E. coli. A stretch of 6 histidine codons is inserted after the methionine initiation codon to provide an affinity tag for purification. The genes thus synthesized were cloned in a pET25b expression vector and the proteins were produced according to the protocol described in Example 1.

For the reductase assay, a reaction mixture containing 50 mM potassium phosphate pH 7.5, 0.1-0.4 mM NADPH, 100 mM NaCl, 5 mM trans crotonyl-CoA and 0.5-1 mg/ml enzyme in a total volume of 120 µl was used and the reaction was carried out at 37° C. for 20 min. Control assays were performed in which either no enzyme was added, or no substrate was added. Each sample was continuously monitored for the decrease of NADPH at 340 nm on a SpectraMax Plus384 UV/Vis Microplate Reader (Molecular Device). Several enzymes demonstrated crotonyl-CoA reductase activity with NADPH as co-substrate (FIG. 14 which shows a time courses of NADPH oxidation in crotonyl-CoA reduction assay with reductase from *Hahella chejuensis* (SEQ ID NO: 17) and varying concentrations of NADPH, Table 5).

TABLE 5

| Enzyme | Activity, µmol/min/mg protein |
| --- | --- |
| Short-chain dehydrogenase/reductase (Fatty alcohol forming acyl-CoA reductase) from *Marinobacter aquaeolei* VT8 (SEQ ID NO: 13) | 1.4 |
| Short chain alcohol dehydrogenase-like protein from *Marinobacter manganoxydans* (SEQ ID NO: 14) | 7.5 |
| Short chain alcohol dehydrogenase-like protein from *Marinobacter algicola* (SEQ ID NO: 16) | 4 |
| Short chain alcohol dehydrogenase-like protein from *Hahella chejuensis* | 4.9 |
| Short chain alcohol dehydrogenase-like protein from *Marinobacter* sp. ELB17 (SEQ ID NO: 15) | 1.2 |

The products of enzymatic reduction of crotonyl-CoA were next analyzed by high-performance liquid chromatography (HPLC).

Example 17

HPLC Studies of Enzymatic Reduction of Crotonyl-CoA

The enzymatic assays were carried out under the following conditions:
50 mM Potassium phosphate pH 7.5
100 mM KCl
24 mM trans crotonyl-CoA
80 mM NADPH The reactions were initiated by addition of 150 µg of purified dehydrogenase/reductase to 150 µl of reaction mixture. Assays were incubated at 37° C. for 0.5-6 h. The reactions were stopped by heating at 65° C. for 5 minutes, reaction mixtures were centrifuged and 120 µl of the clarified supernatant were transferred into a clean vial. The reaction products were then extracted with an equal volume of ethyl acetate. 100 µl of the upper ethyl acetate phase was transferred into a clean vial for HPLC analysis. Commercial crotonaldehyde and crotyl alcohol were used as reference. HPLC-UV analysis was performed using a 1260 Inifinity LC System (Agilent). 10 µl of samples were separated on Zorbax SB-Aq column (250×4.6 mm, 3.5 µm particle size) with a mobile phase flow rate of 1.5 ml/min. The mobile phase consisted of 95:5 (v/v) $H_2O$/Acetonitrile containing 8.4 mM sulfuric acid. Retention time for trans crotyl alcohol and crotonaldehyde in these conditions were 4.3 and 5.4 min, respectively.

The HPLC analysis showed that crotonaldehyde and crotyl alcohol were formed by enzyme catalyzed reduction of crotonyl-CoA. A typical chromatogram obtained with short chain alcohol dehydrogenase-like protein from H. chejuensis is shown on FIG. 15.

These data indicate that the short-chain dehydrogenase/reductase catalyzes the four-electron reduction of crotonyl-CoA to crotyl alcohol via the aldehyde intermediate.

Example 18

Kinetic Parameters of Crotyl Alcohol Production from Trans Crotonyl-CoA

Kinetic parameters values towards NADPH were determined at fixed concentration of crotonyl-CoA (5 mM) and varying NADPH concentration from 0 to 0.8 mM. NADPH oxidation was measured spectrophotometrically at 340 nm according to the procedure described in Example 16.

The short chain alcohol dehydrogenase-like protein from H. chejuensis was found to have a $K_M$ of 1 mM and a $k_{cat}$ of 6.0 $sec^{-1}$ towards NADPH as substrate.

Kinetic parameters values towards crotonyl-CoA were determined at fixed concentration of NADPH (80 mM) and varying crotonyl-CoA concentration from 0 to 32 mM. Kinetic parameters for the overall reaction were determined by crotyl alcohol quantification using HPLC procedure described in Example 17. The short chain alcohol dehydrogenase-like protein from H. chejuensis was found to have a $K_M$ of 5 mM and a $k_{cat}$ of at least 0.05 $sec^{-1}$.

The invention claimed is:

1. A method for the production of butadiene comprising the enzymatic conversion of crotyl alcohol into butadiene wherein the method comprises:
   (i) enzymatically converting crotyl alcohol into crotyl monophosphate using a hydroxyethylthiazole kinase (EC 2.7.1.50) or a thiamine kinase (EC 2.7.1.89); and
   (ii) enzymatically converting crotyl monophosphate into butadiene, wherein the crotyl monophosphate is directly converted into butadiene in a single enzymatic reaction using a terpene synthase selected from an isoprene synthase (EC 4.2.3.27), a myrcene/ocimene synthase (EC 4.2.3.15), a farnesene synthase (EC 4.2.3.46 or EC 4.2.3.47), a pinene synthase (EC 4.2.3.14) or a monoterpene synthase.

2. The method of claim 1 further comprising the enzymatic conversion of crotonyl-CoA into crotyl alcohol.

3. The method of claim 2 wherein crotonyl-CoA is enzymatically converted into crotonaldehyde and then crotonaldehyde is enzymatically converted into crotyl alcohol.

4. The method of claim 3, wherein the enzymatic conversion of crotonyl-CoA into crotonaldehyde is achieved by the use of
   (i) a hydroxymethylglutaryl-CoA reductase (EC 1.1.1.34); and/or
   (ii) an acetaldehyde dehydrogenase (EC 1.2.1.10); and/or
   (iii) an acyl-CoA reductase.

5. The method of claim 3 wherein the enzymatic conversion of crotonaldehyde into crotyl alcohol is achieved by the use of an enzyme selected from:
   (i) a hydroxymethylglutaryl-CoA reductase (EC 1.1.1.34);
   (ii) an alcohol dehydrogenase (EC 1.1.1.1);
   (iii) an aldehyde reductase; or
   (iv) an aldo-keto reductase.

6. The method of claim 3 wherein the enzymatic conversion of crotonyl-CoA into crotyl alcohol is achieved by the use of an aldehyde/alcohol dehydrogenase or by the use of a hydroxymethylglutaryl-CoA reductase (EC 1.1.1.34) or by the use of a short-chain dehydrogenase/fatty acyl-CoA reductase.

7. The method of claim 1 further comprising the step of providing crotyl alcohol by the enzymatic conversion of crotonaldehyde into crotyl alcohol.

8. The method of claim 7 wherein the conversion of crotonaldehyde into crotyl alcohol is achieved by the use of an enzyme selected from:
   (i) a hydroxymethylglutaryl-CoA reductase (EC 1.1.1.34);
   (ii) an alcohol dehydrogenase (EC 1.1.1.1);
   (iii) an aldehyde reductase; or
   (iv) an aldo-keto reductase.

9. A method for the production of butadiene comprising the enzymatic conversion of crotyl alcohol into butadiene wherein the method comprises:
   (a) enzymatically converting crotyl alcohol into crotyl monophosphate using a hydroxyethylthiazole kinase (EC 2.7.1.50) or a thiamine kinase (EC 2.7.1.89);
   (b) enzymatically converting crotyl monophosphate into crotyl diphosphate using isopentenyl phosphate kinase; and
   (c) enzymatically converting crotyl diphosphate into butadiene using a terpene synthase selected from an isoprene synthase (EC 4.2.3.27), a myrcene/ocimene synthase (EC 4.2.3.15); a farnesene synthase (EC 4.2.3.46 or EC 4.2.3.47); a pinene synthase (EC 4.2.3.14) or a monoterpene synthase.

10. The method of claim 9 further comprising the step of providing crotyl alcohol by the enzymatic conversion of crotonaldehyde into crotyl alcohol.

11. The method of claim 10 wherein the conversion of crotonaldehyde into crotyl alcohol is achieved by the use of
   (i) a hydroxymethylglutaryl-CoA reductase (EC 1.1.1.34); and/or
   (ii) an alcohol dehydrogenase (EC 1.1.1.1); and/or
   (iii) an aldehyde reductase; and/or
   (iv) an aldo-keto reductase.

12. The method of claim 9 further comprising the enzymatic conversion of crotonyl-CoA into crotyl alcohol.

13. The method of claim 12 wherein crotonyl-CoA is enzymatically converted into crotonaldehyde and then crotonaldehyde is enzymatically converted into crotyl alcohol.

14. The method of claim 13, wherein the enzymatic conversion of crotonyl-CoA into crotonaldehyde is achieved by the use of
   (i) a hydroxymethylglutaryl-CoA reductase (EC 1.1.1.34); and/or
   (ii) an acetaldehyde dehydrogenase (EC 1.2.1.10); and/or
   (iii) an acyl-CoA reductase.

15. The method of claim 13 wherein the enzymatic conversion of crotonaldehyde into crotyl alcohol is achieved by the use of an enzyme selected from:
   (i) a hydroxymethylglutaryl-CoA reductase (EC 1.1.1.34); or
   (ii) an alcohol dehydrogenase (EC 1.1.1.1); or
   (iii) an aldehyde reductase; or
   (iv) an aldo-keto reductase.

16. The method of claim 13 wherein the enzymatic conversion of crotonyl-CoA into crotyl alcohol is achieved by the use of an aldehyde/alcohol dehydrogenase or by the use of a hydroxymethylglutaryl-CoA reductase (EC 1.1.1.34) or by the use of a short-chain dehydrogenase/fatty acyl-CoA reductase.

17. A method of producing butadiene comprising enzymatically converting crotyl alcohol into butadiene comprising an in vitro cell-free system using a combination of enzymes comprising:
   (a) a hydroxyethylthiazole kinase (EC 2.7.1.50) or a thiamine kinase (EC 2.7.1.89); and
   (b) an isopentenyl phosphate kinase; and
   (c) a terpene synthase wherein said terpene synthase is selected from an isoprene synthase (EC 4.2.3.27), a myrcene/ocimene synthase (EC 4.2.3.15); a farnesene synthase (EC 4.2.3.46 or EC 4.2.3.47); a pinene synthase (EC 4.2.3.14) or a monoterpene synthase.

18. A recombinant microorganism or plant cell comprising:
   (a) an overexpressed hydroxyethylthiazole kinase (EC 2.7.1.50) or a thiamine kinase (EC 2.7.1.89); and
   (b) an overexpressed isopentenyl phosphate kinase; and
   (c) an overexpressed terpene synthase, wherein said terpene synthase is selected from an isoprene synthase (EC 4.2.3.27), a myrcene/ocimene synthase (EC 4.2.3.15); a farnesene synthase (EC 4.2.3.46 or EC 4.2.3.47); a pinene synthase (EC 4.2.3.14) or a monoterpene synthase and which is capable of converting crotyl alcohol into butadiene.

19. The recombinant microorganism or plant cell of claim 18, wherein the recombinant microorganism or plant cell further expresses an enzyme selected from:
   (a) hydroxymethylglutaryl-CoA reductase (EC 1.1.1.34);
   (b) aldehyde/alcohol dehydrogenase; or
   (c) Short-chain dehydrogenase/fatty acyl-CoA reductase and which is capable of converting crotonyl-CoA into butadiene.

20. The recombinant microorganism or plant cell of claim 18, wherein the recombinant microorganism or plant cell further expresses an enzyme selected from:
   (a) acyl-CoA reductase or acetaldehyde dehydrogenase (EC 1.2.1.10) or hydroxymethylglutaryl-CoA reductase (EC 1.1.1.34) or aldehyde/alcohol dehydrogenase or short-chain dehydrogenase/fatty acyl-CoA reductase and
   (b) alcohol dehydrogenase (EC 1.1.1.1) or aldehyde reductase or aldo-keto reductase
and which is capable of converting crotonyl-CoA into butadiene.

21. The recombinant microorganism or plant cell of claim 20, wherein the acyl-CoA reductase is selected from:
   (a) cinnamoyl-CoA reductase (EC 1.2.1.44);
   (b) long-chain-fatty-acyl-CoA reductase (EC 1.2.1.50); or
   (c) malonyl-CoA reductase (EC 1.2.1.75).

22. The recombinant microorganism or plant cell of claim 18, wherein the recombinant microorganism or plant cell further expresses an enzyme selected from:

(a) acyl-CoA reductase or acetaldehyde dehydrogenase (EC 1.2.1.10); and
(b) alcohol dehydrogenase (EC 1.1.1.1) or aldehyde reductase or aldo-keto reductase or hydroxymethylglutaryl-CoA reductase (EC 1.1.1.34) or aldehyde/alcohol dehydrogenase or short-chain dehydrogenase/fatty acyl-CoA reductase and which is capable of converting crotonyl-CoA into butadiene.

23. The recombinant microorganism or plant cell of claim 22, wherein the acyl-CoA reductase is selected from:
    (a) cinnamoyl-CoA reductase (EC 1.2.1.44);
    (b) long-chain-fatty-acyl-CoA reductase (EC 1.2.1.50); or
    (c) malonyl-CoA reductase (EC 1.2.1.75).

24. An in vitro, cell-free system comprising:
    (a) a hydroxyethylthiazole kinase (EC 2.7.1.50) or a thiamine kinase (EC 2.7.1.89); and
    (b) an isopentenyl phosphate kinase; and
    (c) a terpene synthase wherein said terpene synthase is selected from an isoprene synthase (EC 4.2.3.27), a myrcene/ocimene synthase (EC 4.2.3.15); a farnesene synthase (EC 4.2.3.46 or EC 4.2.3.47); a pinene synthase (EC 4.2.3.14) or a monoterpene synthase.

25. The in vitro cell-free system of claim 24 further comprising crotyl alcohol.

26. A recombinant microorganism or plant cell which overexpresses a heterologous enzyme selected from:
    (a) hydroxymethylglutaryl-CoA reductase (EC 1.1.1.34); or
    (b) short-chain dehydrogenase/fatty acyl-CoA reductase,
and which is capable of converting crotonyl-CoA into crotyl alcohol.

27. A recombinant microorganism or plant cell comprising:
    (a) an overexpressed heterologous acyl-CoA reductase or acetaldehyde dehydrogenase (EC 1.2.1.10) or hydroxymethylglutaryl-CoA reductase (EC 1.1.1.34) or aldehyde/alcohol dehydrogenase or short-chain dehydrogenase/fatty acyl-CoA reductase; and
    (b) an overexpressed heterologous alcohol dehydrogenase (EC 1.1.1.1) or aldehyde reductase or aldo-keto reductase and which is capable of converting crotonyl-CoA into crotyl alcohol.

28. The recombinant microorganism or plant cell of claim 27, wherein the acyl-CoA reductase is selected from:
    (a) cinnamoyl-CoA reductase (EC 1.2.1.44);
    (b) long-chain-fatty-acyl-CoA reductase (EC 1.2.1.50); or
    (c) malonyl-CoA reductase (EC 1.2.1.75).

29. A recombinant microorganism or plant cell comprising:
    (a) an overexpressed heterologous acyl-CoA reductase or acetaldehyde dehydrogenase (EC 1.2.1.10); and
    (b) an overexpressed heterologous alcohol dehydrogenase (EC 1.1.1.1) or aldehyde reductase or aldo-keto reductase or hydroxymethylglutaryl-CoA reductase (EC 1.1.1.34) or aldehyde/alcohol dehydrogenase or short-chain dehydrogenase/fatty acyl-CoA reductase and which is capable of converting crotonyl-CoA into crotyl alcohol.

30. The recombinant microorganism or plant cell of claim 29, wherein the acyl-CoA reductase is selected from:
    (a) cinnamoyl-CoA reductase (EC 1.2.1.44);
    (b) long-chain-fatty-acyl-CoA reductase (EC 1.2.1.50); or
    (c) malonyl-CoA reductase (EC 1.2.1.75).

31. A recombinant microorganism or plant cell comprising:
    (a) an overexpressed hydroxyethylthiazole kinase (EC 2.7.1.50) or a thiamine kinase (EC 2.7.1.89); and
    (b) an overexpressed terpene synthase selected from an isoprene synthase (EC 4.2.3.27), a myrcene/ocimene synthase (EC 4.2.3.15), a farnesene synthase (EC 4.2.3.46 or EC 4.2.3.47), a pinene synthase (EC 4.2.3.14) or a monoterpene synthase.

32. An in vitro, cell-free system comprising:
    (a) a hydroxyethylthiazole kinase (EC 2.7.1.50) or a thiamine kinase (EC 2.7.1.89); and
    (b) a terpene synthase selected from an isoprene synthase (EC 4.2.3.27), a myrcene/ocimene synthase (EC 4.2.3.15), a farnesene synthase (EC 4.2.3.46 or EC 4.2.3.47), a pinene synthase (EC 4.2.3.14) or a monoterpene synthase.

* * * * *

SEQUENCE LISTING

<160> NUMBER OF SEQ ID NOS: 21

<210> SEQ ID NO 1
<211> LENGTH: 272
<212> TYPE: PRT
<213> ORGANISM: Bacillus subtilis

```
<400> SEQUENCE: 1

Met Asp Ala Gln Ser Ala Ala Lys Cys Leu Thr Ala Val Arg Arg His
1               5                   10                  15

Ser Pro Leu Val His Ser Ile Thr Asn Asn Val Thr Asn Phe Thr
            20                  25                  30

Ala Asn Gly Leu Leu Ala Leu Gly Ala Ser Pro Val Met Ala Tyr Ala
            35                  40                  45

Lys Glu Glu Val Ala Asp Met Ala Lys Ile Ala Gly Ala Leu Val Leu
50                  55                  60

Asn Ile Gly Thr Leu Ser Lys Glu Ser Val Glu Ala Met Ile Ile Ala
65                  70                  75                  80

Gly Lys Ser Ala Asn Glu His Gly Val Pro Val Ile Leu Asp Pro Val
                85                  90                  95

Gly Ala Gly Ala Thr Pro Phe Arg Thr Glu Ser Ala Arg Asp Ile Ile
            100                 105                 110

Arg Glu Val Arg Leu Ala Ala Ile Arg Gly Asn Ala Ala Glu Ile Ala
            115                 120                 125

His Thr Val Gly Val Thr Asp Trp Leu Ile Lys Gly Val Asp Ala Gly
130                 135                 140

Glu Gly Gly Gly Asp Ile Ile Arg Leu Ala Gln Gln Ala Ala Gln Lys
145                 150                 155                 160

Leu Asn Thr Val Ile Ala Ile Thr Gly Glu Val Asp Val Ile Ala Asp
            165                 170                 175

Thr Ser His Val Tyr Thr Leu His Asn Gly His Lys Leu Leu Thr Lys
            180                 185                 190

Val Thr Gly Ala Gly Cys Leu Leu Thr Ser Val Val Gly Ala Phe Cys
            195                 200                 205

Ala Val Glu Glu Asn Pro Leu Phe Ala Ala Ile Ala Ala Ile Ser Ser
210                 215                 220

Tyr Gly Val Ala Ala Gln Leu Ala Ala Gln Thr Ala Asp Lys Gly
225                 230                 235                 240

Pro Gly Ser Phe Gln Ile Glu Leu Leu Asn Lys Leu Ser Thr Val Thr
            245                 250                 255

Glu Gln Asp Val Gln Glu Trp Ala Thr Ile Glu Arg Val Thr Val Ser
            260                 265                 270

<210> SEQ ID NO 2
<211> LENGTH: 262
<212> TYPE: PRT
<213> ORGANISM: E. coli

<400> SEQUENCE: 2

Met Gln Val Asp Leu Leu Gly Ser Ala Gln Ser Ala His Ala Leu His
1               5                   10                  15

Leu Phe His Gln His Ser Pro Leu Val His Cys Met Thr Asn Asp Val
            20                  25                  30

Val Gln Thr Phe Thr Ala Asn Thr Leu Leu Ala Leu Gly Ala Ser Pro
            35                  40                  45

Ala Met Val Ile Glu Thr Glu Glu Ala Ser Gln Phe Ala Ala Ile Ala
50                  55                  60

Ser Ala Leu Leu Ile Asn Val Gly Thr Leu Thr Gln Pro Arg Ala Gln
65                  70                  75                  80

Ala Met Arg Ala Ala Val Glu Gln Ala Lys Ser Ser Gln Thr Pro Trp
            85                  90                  95
```

```
Thr Leu Asp Pro Val Ala Val Gly Ala Leu Asp Tyr Arg Arg His Phe
            100                 105                 110

Cys His Glu Leu Leu Ser Phe Lys Pro Ala Ala Ile Arg Gly Asn Ala
            115                 120                 125

Ser Glu Ile Met Ala Leu Ala Gly Ile Ala Asn Gly Gly Arg Gly Val
            130                 135                 140

Asp Thr Thr Asp Ala Ala Ala Asn Ala Ile Pro Ala Ala Gln Thr Leu
145                 150                 155                 160

Ala Arg Glu Thr Gly Ala Ile Val Val Thr Gly Glu Met Asp Tyr
                165                 170                 175

Val Thr Asp Gly His Arg Ile Ile Gly Ile His Gly Gly Asp Pro Leu
            180                 185                 190

Met Thr Lys Val Val Gly Thr Gly Cys Ala Leu Ser Ala Val Val Ala
            195                 200                 205

Ala Cys Cys Ala Leu Pro Gly Asp Thr Leu Glu Asn Val Ala Ser Ala
210                 215                 220

Cys His Trp Met Lys Gln Ala Gly Glu Arg Ala Val Ala Arg Ser Glu
225                 230                 235                 240

Gly Pro Gly Ser Phe Val Pro His Phe Leu Asp Ala Leu Trp Gln Leu
                245                 250                 255

Thr Gln Glu Val Gln Ala
            260

<210> SEQ ID NO 3
<211> LENGTH: 267
<212> TYPE: PRT
<213> ORGANISM: Rhizobium leguminosarum

<400> SEQUENCE: 3

Met Gln Thr Arg Thr Thr Pro Gly Ala Met Leu Lys Ala Met Arg Glu
1               5                   10                  15

Lys Pro Pro Leu Val Gln Cys Ile Thr Asn Tyr Val Ala Met Asn Ile
            20                  25                  30

Ala Ala Asn Val Leu Leu Ala Ala Gly Ala Ser Pro Ala Met Val His
            35                  40                  45

Ala Ala Glu Glu Ala Gly Glu Phe Ala Ala Ile Ala Ser Ala Leu Thr
        50                  55                  60

Ile Asn Ile Gly Thr Leu Ser Thr Gln Trp Ile Asp Gly Met Gln Ala
65                  70                  75                  80

Ala Ala Lys Ala Ala Thr Ser Ala Gly Lys Pro Trp Val Leu Asp Pro
                85                  90                  95

Val Ala His Tyr Ala Thr Ala Phe Arg Arg Asn Ala Val Ala Glu Leu
            100                 105                 110

Leu Ala Leu Lys Pro Thr Ile Ile Arg Gly Asn Ala Ser Glu Ile Ile
            115                 120                 125

Ala Leu Ala Gly Gly Glu Ser Arg Gly Gln Gly Val Asp Ser Arg Asp
        130                 135                 140

Pro Val Glu Gln Ala Glu Gly Ser Ala Arg Trp Leu Ala Glu Arg Gln
145                 150                 155                 160

Arg Ala Val Val Ala Val Thr Gly Ala Val Asp Phe Val Thr Asp Gly
                165                 170                 175

Glu Arg Ala Val Arg Ile Glu Gly Gly Ser Ala Leu Met Pro Gln Val
            180                 185                 190
```

```
Thr Ala Leu Gly Cys Ser Leu Thr Cys Leu Val Gly Ala Phe Ala Ala
            195                 200                 205

Thr Ala Pro Glu Asp Ile Phe Gly Ala Thr Val Ala Ala Leu Ser Thr
        210                 215                 220

Phe Ala Ile Ala Gly Glu Glu Ala Ala Leu Gly Ala Ala Gly Pro Gly
225                 230                 235                 240

Ser Phe Ser Trp Arg Phe Leu Asp Ala Leu Ala Ala Leu Asp Ala Glu
                245                 250                 255

Thr Leu Asp Ala Arg Ala Arg Ile Ser Ala Ala
            260                 265

<210> SEQ ID NO 4
<211> LENGTH: 245
<212> TYPE: PRT
<213> ORGANISM: Thermoplasma acidophilum

<400> SEQUENCE: 4

Met Met Ile Leu Lys Ile Gly Gly Ser Val Ile Thr Asp Lys Ser Ala
1               5                   10                  15

Tyr Arg Thr Ala Arg Thr Tyr Ala Ile Arg Ser Ile Val Lys Val Leu
            20                  25                  30

Ser Gly Ile Glu Asp Leu Val Cys Val Val His Gly Gly Gly Ser Phe
        35                  40                  45

Gly His Ile Lys Ala Met Glu Phe Gly Leu Pro Gly Pro Lys Asn Pro
    50                  55                  60

Arg Ser Ser Ile Gly Tyr Ser Ile Val His Arg Asp Met Glu Asn Leu
65                  70                  75                  80

Asp Leu Met Val Ile Asp Ala Met Ile Glu Met Gly Met Arg Pro Ile
                85                  90                  95

Ser Val Pro Ile Ser Ala Leu Arg Tyr Asp Gly Arg Phe Asp Tyr Thr
            100                 105                 110

Pro Leu Ile Arg Tyr Ile Asp Ala Gly Phe Val Pro Val Ser Tyr Gly
        115                 120                 125

Asp Val Tyr Ile Lys Asp Glu His Ser Tyr Gly Ile Tyr Ser Gly Asp
    130                 135                 140

Asp Ile Met Ala Asp Met Ala Glu Leu Leu Lys Pro Asp Val Ala Val
145                 150                 155                 160

Phe Leu Thr Asp Val Asp Gly Ile Tyr Ser Lys Asp Pro Lys Arg Asn
                165                 170                 175

Pro Asp Ala Val Leu Leu Arg Asp Ile Asp Thr Asn Ile Thr Phe Asp
            180                 185                 190

Arg Val Gln Asn Asp Val Thr Gly Gly Ile Gly Lys Lys Phe Glu Ser
        195                 200                 205

Met Val Lys Met Lys Ser Ser Val Lys Asn Gly Val Tyr Leu Ile Asn
    210                 215                 220

Gly Asn His Pro Glu Arg Ile Gly Asp Ile Gly Lys Glu Ser Phe Ile
225                 230                 235                 240

Gly Thr Val Ile Arg
                245

<210> SEQ ID NO 5
<211> LENGTH: 266
<212> TYPE: PRT
<213> ORGANISM: Methanothermobacter thermautotrophicus str. Delta H

<400> SEQUENCE: 5
```

```
Met Ile Ile Leu Lys Leu Gly Gly Ser Val Ile Thr Arg Lys Asp Ser
1               5                   10                  15

Glu Glu Pro Ala Ile Asp Arg Asp Asn Leu Glu Arg Ile Ala Ser Glu
            20                  25                  30

Ile Gly Asn Ala Ser Pro Ser Ser Leu Met Ile Val His Gly Ala Gly
                35                  40                  45

Ser Phe Gly His Pro Phe Ala Gly Glu Tyr Arg Ile Gly Ser Glu Ile
    50                  55                  60

Glu Asn Glu Glu Asp Leu Arg Arg Arg Phe Gly Phe Ala Leu Thr
65                  70                  75                  80

Gln Asn Trp Val Lys Lys Leu Asn Ser His Val Cys Asp Ala Leu Leu
                85                  90                  95

Ala Glu Gly Ile Pro Ala Val Ser Met Gln Pro Ser Ala Phe Ile Arg
            100                 105                 110

Ala His Ala Gly Arg Ile Ser His Ala Asp Ile Ser Leu Ile Arg Ser
        115                 120                 125

Tyr Leu Glu Glu Gly Met Val Pro Val Val Tyr Gly Asp Val Val Leu
    130                 135                 140

Asp Ser Asp Arg Arg Leu Lys Phe Ser Val Ile Ser Gly Asp Gln Leu
145                 150                 155                 160

Ile Asn His Phe Ser Leu Arg Leu Met Pro Glu Arg Val Ile Leu Gly
                165                 170                 175

Thr Asp Val Asp Gly Val Tyr Thr Arg Asn Pro Lys Lys His Pro Asp
            180                 185                 190

Ala Arg Leu Leu Asp Val Ile Gly Ser Leu Asp Leu Glu Ser Leu
        195                 200                 205

Asp Gly Thr Leu Asn Thr Asp Val Thr Gly Gly Met Val Gly Lys Ile
    210                 215                 220

Arg Glu Leu Leu Leu Leu Ala Glu Lys Gly Val Glu Ser Glu Ile Ile
225                 230                 235                 240

Asn Ala Ala Val Pro Gly Asn Ile Glu Arg Ala Leu Leu Gly Glu Glu
                245                 250                 255

Val Arg Gly Thr Arg Ile Thr Gly Lys His
            260                 265

<210> SEQ ID NO 6
<211> LENGTH: 260
<212> TYPE: PRT
<213> ORGANISM: Methanocaldococcus jannaschii

<400> SEQUENCE: 6

Met Leu Thr Ile Leu Lys Leu Gly Gly Ser Ile Leu Ser Asp Lys Asn
1               5                   10                  15

Val Pro Tyr Ser Ile Lys Trp Asp Asn Leu Glu Arg Ile Ala Met Glu
            20                  25                  30

Ile Lys Asn Ala Leu Asp Tyr Tyr Lys Asn Gln Asn Lys Glu Ile Lys
                35                  40                  45

Leu Ile Leu Val His Gly Gly Ala Phe Gly His Pro Val Ala Lys
    50                  55                  60

Lys Tyr Leu Lys Ile Glu Asp Gly Lys Lys Ile Phe Ile Asn Met Glu
65                  70                  75                  80

Lys Gly Phe Trp Glu Ile Gln Arg Ala Met Arg Arg Phe Asn Asn Ile
                85                  90                  95

Ile Ile Asp Thr Leu Gln Ser Tyr Asp Ile Pro Ala Val Ser Ile Gln
            100                 105                 110
```

```
Pro Ser Ser Phe Val Val Phe Gly Asp Lys Leu Ile Phe Asp Thr Ser
        115                 120                 125

Ala Ile Lys Glu Met Leu Lys Arg Asn Leu Val Pro Val Ile His Gly
    130                 135                 140

Asp Ile Val Ile Asp Lys Asn Gly Tyr Arg Ile Ile Ser Gly Asp
145                 150                 155                 160

Asp Ile Val Pro Tyr Leu Ala Asn Glu Leu Lys Ala Asp Leu Ile Leu
                165                 170                 175

Tyr Ala Thr Asp Val Asp Gly Val Leu Ile Asp Asn Lys Pro Ile Lys
            180                 185                 190

Arg Ile Asp Lys Asn Asn Ile Tyr Lys Ile Leu Asn Tyr Leu Ser Gly
        195                 200                 205

Ser Asn Ser Ile Asp Val Thr Gly Gly Met Lys Tyr Lys Ile Asp Met
    210                 215                 220

Ile Arg Lys Asn Lys Cys Arg Gly Phe Val Phe Asn Gly Asn Lys Ala
225                 230                 235                 240

Asn Asn Ile Tyr Lys Ala Leu Leu Gly Glu Val Glu Gly Thr Glu Ile
                245                 250                 255

Asp Phe Ser Glu
            260

<210> SEQ ID NO 7
<211> LENGTH: 608
<212> TYPE: PRT
<213> ORGANISM: Pueraria lobata

<400> SEQUENCE: 7

Met Ala Thr Asn Leu Leu Cys Leu Ser Asn Lys Leu Ser Ser Pro Thr
1               5                   10                  15

Pro Thr Pro Ser Thr Arg Phe Pro Gln Ser Lys Asn Phe Ile Thr Gln
            20                  25                  30

Lys Thr Ser Leu Ala Asn Pro Lys Pro Trp Arg Val Ile Cys Ala Thr
        35                  40                  45

Ser Ser Gln Phe Thr Gln Ile Thr Glu His Asn Ser Arg Arg Ser Ala
    50                  55                  60

Asn Tyr Gln Pro Asn Leu Trp Asn Phe Glu Phe Leu Gln Ser Leu Glu
65                  70                  75                  80

Asn Asp Leu Lys Val Glu Lys Leu Glu Glu Lys Ala Thr Lys Leu Glu
                85                  90                  95

Glu Glu Val Arg Cys Met Ile Asn Arg Val Asp Thr Gln Pro Leu Ser
            100                 105                 110

Leu Leu Glu Leu Ile Asp Asp Val Gln Arg Leu Gly Leu Thr Tyr Lys
        115                 120                 125

Phe Glu Lys Asp Ile Ile Lys Ala Leu Glu Asn Ile Val Leu Leu Asp
    130                 135                 140

Glu Asn Lys Lys Asn Lys Ser Asp Leu His Ala Thr Ala Leu Ser Phe
145                 150                 155                 160

Arg Leu Leu Arg Gln His Gly Phe Glu Val Ser Gln Asp Val Phe Glu
                165                 170                 175

Arg Phe Lys Asp Lys Glu Gly Gly Phe Ser Gly Glu Leu Lys Gly Asp
            180                 185                 190

Val Gln Gly Leu Leu Ser Leu Tyr Glu Ala Ser Tyr Leu Gly Phe Glu
        195                 200                 205
```

-continued

Gly Glu Asn Leu Leu Glu Glu Ala Arg Thr Phe Ser Ile Thr His Leu
210                 215                 220

Lys Asn Leu Lys Glu Gly Ile Asn Thr Lys Val Ala Glu Gln Val
225                 230                 235                 240

Ser His Ala Leu Glu Leu Pro Tyr His Gln Arg Leu His Arg Leu Glu
            245                 250                 255

Ala Arg Trp Phe Leu Asp Lys Tyr Glu Pro Lys Glu Pro His His Gln
        260                 265                 270

Leu Leu Leu Glu Leu Ala Lys Leu Asp Phe Asn Met Val Gln Thr Leu
    275                 280                 285

His Gln Lys Glu Leu Gln Asp Leu Ser Arg Trp Trp Thr Glu Met Gly
290                 295                 300

Leu Ala Ser Lys Leu Asp Phe Val Arg Asp Arg Leu Met Glu Val Tyr
305                 310                 315                 320

Phe Trp Ala Leu Gly Met Ala Pro Asp Pro Gln Phe Gly Glu Cys Arg
            325                 330                 335

Lys Ala Val Thr Lys Met Phe Gly Leu Val Thr Ile Ile Asp Asp Val
        340                 345                 350

Tyr Asp Val Tyr Gly Thr Leu Asp Glu Leu Gln Leu Phe Thr Asp Ala
    355                 360                 365

Val Glu Arg Trp Asp Val Asn Ala Ile Asn Thr Leu Pro Asp Tyr Met
370                 375                 380

Lys Leu Cys Phe Leu Ala Leu Tyr Asn Thr Val Asn Asp Thr Ser Tyr
385                 390                 395                 400

Ser Ile Leu Lys Glu Lys Gly His Asn Asn Leu Ser Tyr Leu Thr Lys
            405                 410                 415

Ser Trp Arg Glu Leu Cys Lys Ala Phe Leu Gln Glu Ala Lys Trp Ser
        420                 425                 430

Asn Asn Lys Ile Ile Pro Ala Phe Ser Lys Tyr Leu Glu Asn Ala Ser
    435                 440                 445

Val Ser Ser Ser Gly Val Ala Leu Leu Ala Pro Ser Tyr Phe Ser Val
450                 455                 460

Cys Gln Gln Gln Glu Asp Ile Ser Asp His Ala Leu Arg Ser Leu Thr
465                 470                 475                 480

Asp Phe His Gly Leu Val Arg Ser Ser Cys Val Ile Phe Arg Leu Cys
            485                 490                 495

Asn Asp Leu Ala Thr Ser Ala Ala Glu Leu Glu Arg Gly Glu Thr Thr
        500                 505                 510

Asn Ser Ile Ile Ser Tyr Met His Glu Asn Asp Gly Thr Ser Glu Glu
    515                 520                 525

Gln Ala Arg Glu Glu Leu Arg Lys Leu Ile Asp Ala Glu Trp Lys Lys
530                 535                 540

Met Asn Arg Glu Arg Val Ser Asp Ser Thr Leu Leu Pro Lys Ala Phe
545                 550                 555                 560

Met Glu Ile Ala Val Asn Met Ala Arg Val Ser His Cys Thr Tyr Gln
            565                 570                 575

Tyr Gly Asp Gly Leu Gly Arg Pro Asp Tyr Ala Thr Glu Asn Arg Ile
        580                 585                 590

Lys Leu Leu Leu Ile Asp Pro Phe Pro Ile Asn Gln Leu Met Tyr Val
    595                 600                 605

<210> SEQ ID NO 8
<211> LENGTH: 582
<212> TYPE: PRT

<213> ORGANISM: Eucalyptus globulus

<400> SEQUENCE: 8

```
Met Ala Leu Arg Leu Phe Thr Pro His Leu Pro Val Leu Ser Ser
 1               5                  10                  15

Arg Arg Ala Asn Gly Arg Val Arg Cys Ser Ala Ser Thr Gln Ile Ser
                20                  25                  30

Asp Pro Gln Glu Gly Arg Arg Ser Ala Asn Tyr Gln Pro Ser Val Trp
            35                  40                  45

Thr Tyr Asn Tyr Leu Gln Ser Ile Val Ala Gly Gly Arg Gln Ser
        50                  55                  60

Arg Arg Glu Val Glu Gln Lys Glu Lys Val Gln Ile Leu Glu Glu
 65                  70                  75                  80

Glu Val Arg Gly Ala Leu Asn Asp Glu Lys Ala Glu Thr Phe Thr Ile
                85                  90                  95

Phe Ala Thr Val Asp Asp Ile Gln Arg Leu Gly Leu Gly Asp His Phe
            100                 105                 110

Glu Glu Asp Ile Ser Asn Ala Leu Arg Arg Cys Val Ser Lys Gly Ala
            115                 120                 125

Val Phe Met Ser Leu Gln Lys Ser Leu His Gly Thr Ala Leu Gly Phe
130                 135                 140

Arg Leu Leu Arg Gln His Gly Tyr Glu Val Ser Gln Asp Val Phe Lys
145                 150                 155                 160

Ile Phe Leu Asp Glu Ser Gly Ser Phe Val Lys Thr Leu Gly Gly Asp
                165                 170                 175

Val Gln Gly Val Leu Ser Leu Tyr Glu Ala Ser His Leu Ala Phe Glu
            180                 185                 190

Glu Glu Asp Ile Leu His Lys Ala Arg Ser Phe Ala Ile Lys His Leu
            195                 200                 205

Glu Asn Leu Asn Ser Asp Val Asp Lys Asp Leu Gln Asp Gln Val Lys
        210                 215                 220

His Glu Leu Glu Leu Pro Leu His Arg Arg Met Pro Leu Leu Glu Ala
225                 230                 235                 240

Arg Arg Ser Ile Glu Ala Tyr Ser Arg Arg Glu Tyr Thr Asn Pro Gln
                245                 250                 255

Ile Leu Glu Leu Ala Leu Thr Asp Phe Asn Val Ser Gln Ser Thr Leu
            260                 265                 270

Gln Arg Asp Leu Gln Glu Met Leu Gly Trp Trp Asn Asn Thr Gly Leu
        275                 280                 285

Ala Lys Arg Leu Ser Phe Ala Arg Asp Arg Leu Ile Glu Cys Phe Phe
290                 295                 300

Trp Ala Val Gly Ile Ala His Glu Pro Ser Leu Ser Ile Cys Arg Lys
305                 310                 315                 320

Ala Val Thr Lys Ala Phe Ala Leu Ile Leu Val Leu Asp Asp Val Tyr
                325                 330                 335

Asp Val Phe Gly Thr Leu Glu Glu Leu Glu Leu Phe Thr Glu Ala Val
            340                 345                 350

Arg Arg Trp Asp Leu Asn Ala Val Glu Asp Leu Pro Val Tyr Met Lys
        355                 360                 365

Leu Cys Tyr Leu Ala Leu Tyr Asn Ser Val Asn Glu Met Ala Tyr Glu
        370                 375                 380

Thr Leu Lys Glu Lys Gly Glu Asn Val Ile Pro Tyr Leu Ala Lys Ala
385                 390                 395                 400
```

Trp Tyr Asp Leu Cys Lys Ala Phe Leu Gln Glu Ala Lys Trp Ser Asn
                405                 410                 415

Ser Arg Ile Ile Pro Gly Val Glu Glu Tyr Leu Asn Asn Gly Trp Val
            420                 425                 430

Ser Ser Ser Gly Ser Val Met Leu Ile His Ala Tyr Phe Leu Ala Ser
            435                 440                 445

Pro Ser Ile Arg Lys Glu Glu Leu Glu Ser Leu Glu His Tyr His Asp
        450                 455                 460

Leu Leu Arg Leu Pro Ser Leu Ile Phe Arg Leu Thr Asn Asp Ile Ala
465                 470                 475                 480

Ser Ser Ser Ala Glu Leu Glu Arg Gly Glu Thr Thr Asn Ser Ile Arg
                485                 490                 495

Cys Phe Met Gln Glu Lys Gly Ile Ser Glu Leu Glu Ala Arg Glu Cys
            500                 505                 510

Val Lys Glu Glu Ile Asp Thr Ala Trp Lys Lys Met Asn Lys Tyr Met
            515                 520                 525

Val Asp Arg Ser Thr Phe Asn Gln Ser Phe Val Arg Met Thr Tyr Asn
        530                 535                 540

Leu Ala Arg Met Ala His Cys Val Tyr Gln Asp Gly Asp Ala Ile Gly
545                 550                 555                 560

Ser Pro Asp Asp Leu Ser Trp Asn Arg Val His Ser Leu Ile Ile Lys
                565                 570                 575

Pro Ile Ser Pro Ala Ala
            580

<210> SEQ ID NO 9
<211> LENGTH: 595
<212> TYPE: PRT
<213> ORGANISM: Lotus japonicus

<400> SEQUENCE: 9

Met Ala Gln Ser Phe Ser Met Val Leu Asn Ser Ser Phe Thr Ser His
1               5                   10                  15

Pro Ile Phe Cys Lys Pro Gln Lys Leu Ile Ile Arg Gly His Asn Leu
            20                  25                  30

Leu Gln Gly His Arg Ile Asn Ser Pro Ile Pro Cys Tyr Ala Ser Thr
        35                  40                  45

Ser Ser Thr Ser Val Ser Gln Arg Lys Ser Ala Asn Tyr Gln Pro Asn
    50                  55                  60

Ile Trp Asn Tyr Asp Tyr Leu Gln Ser Leu Lys Leu Gly Tyr Ala Asp
65                  70                  75                  80

Ala His Tyr Glu Asp Met Ala Lys Lys Leu Gln Glu Glu Val Arg Arg
                85                  90                  95

Ile Ile Lys Asp Asp Lys Ala Glu Ile Trp Thr Thr Leu Glu Leu Ile
            100                 105                 110

Asp Asp Val Lys Arg Leu Gly Leu Gly Tyr His Phe Glu Lys Glu Ile
        115                 120                 125

Arg Glu Val Leu Asn Lys Phe Leu Ser Leu Asn Thr Cys Val His Arg
    130                 135                 140

Ser Leu Asp Lys Thr Ala Leu Cys Phe Arg Leu Leu Arg Glu Tyr Gly
145                 150                 155                 160

Ser Asp Val Ser Ala Asp Ile Phe Glu Arg Phe Leu Asp Gln Asn Gly
                165                 170                 175

Asn Phe Lys Thr Ser Leu Val Asn Asn Val Lys Gly Met Leu Ser Leu
            180                 185                 190

```
Tyr Glu Ala Ser Phe Leu Ser Tyr Glu Gly Glu Gln Ile Leu Asp Lys
            195                 200                 205

Ala Asn Ala Phe Thr Ser Phe His Leu Lys Ser Ile His Glu Glu Asp
            210                 215                 220

Ile Asn Asn Ile Leu Leu Glu Gln Val Asn His Ala Leu Glu Leu Pro
225                 230                 235                 240

Leu His Arg Arg Ile His Arg Leu Glu Ala Arg Trp Tyr Thr Glu Ser
                245                 250                 255

Tyr Ser Arg Arg Lys Asp Ala Asn Trp Val Leu Leu Glu Ala Ala Lys
                260                 265                 270

Leu Asp Phe Asn Met Val Gln Ser Thr Leu Gln Lys Asp Leu Gln Glu
            275                 280                 285

Met Ser Arg Trp Trp Lys Gly Met Gly Leu Ala Pro Lys Leu Ser Phe
            290                 295                 300

Ser Arg Asp Arg Leu Met Glu Cys Phe Phe Trp Thr Val Gly Met Ala
305                 310                 315                 320

Phe Glu Pro Lys Tyr Ser Asp Leu Arg Lys Gly Leu Thr Lys Val Thr
                325                 330                 335

Ser Leu Ile Thr Thr Ile Asp Asp Ile Tyr Asp Val His Gly Thr Leu
            340                 345                 350

Glu Glu Leu Glu Leu Phe Thr Ala Ile Val Glu Ser Trp Asp Ile Lys
            355                 360                 365

Ala Met Gln Val Leu Pro Glu Tyr Met Lys Ile Ser Phe Leu Ala Leu
370                 375                 380

Tyr Asn Thr Val Asn Glu Leu Ala Tyr Asp Ala Leu Arg Glu Gln Gly
385                 390                 395                 400

His Asp Ile Leu Pro Tyr Leu Thr Lys Ala Trp Ser Asp Met Leu Lys
                405                 410                 415

Ala Phe Leu Gln Glu Ala Lys Trp Cys Arg Glu Lys His Leu Pro Lys
            420                 425                 430

Phe Glu His Tyr Leu Asn Asn Ala Trp Val Ser Val Ser Gly Val Val
            435                 440                 445

Ile Leu Thr His Ala Tyr Phe Leu Leu Asn His Asn Thr Thr Lys Glu
            450                 455                 460

Val Leu Glu Ala Leu Glu Asn Tyr His Ala Leu Leu Lys Arg Pro Ser
465                 470                 475                 480

Ile Ile Phe Arg Leu Cys Asn Asp Leu Gly Thr Ser Thr Ala Glu Leu
                485                 490                 495

Gln Arg Gly Glu Val Ala Asn Ser Ile Leu Ser Cys Met His Glu Asn
            500                 505                 510

Asp Ile Gly Glu Glu Ser Ala His Gln His Ile His Ser Leu Leu Asn
            515                 520                 525

Glu Thr Trp Lys Lys Met Asn Arg Asp Arg Phe Ile His Ser Pro Phe
            530                 535                 540

Pro Glu Pro Phe Val Glu Ile Ala Thr Asn Leu Ala Arg Ile Ala Gln
545                 550                 555                 560

Cys Thr Tyr Gln Thr Gly Asp Gly His Gly Ala Pro Asp Ser Ile Ala
                565                 570                 575

Lys Asn Arg Val Lys Ser Leu Ile Ile Glu Pro Ile Val Leu Asn Gly
                580                 585                 590

Asp Ile Tyr
        595
```

<210> SEQ ID NO 10
<211> LENGTH: 593
<212> TYPE: PRT
<213> ORGANISM: Phaseolus lunatus

<400> SEQUENCE: 10

Met Leu Leu Asn Ser Ser Phe Ile Ser Arg Val Thr Phe Ala Lys Pro
1               5                   10                  15

Leu Lys Pro Val Ala Pro Asn Leu Leu His Arg Arg Ile Ile Phe Pro
            20                  25                  30

Arg Cys Asn Gly Thr Thr Ile Asn Val Asn Ala Ser Glu Arg Lys Ser
        35                  40                  45

Ala Asn Tyr Gln Pro Asn Leu Trp Thr Tyr Asp Phe Leu Gln Ser Leu
    50                  55                  60

Lys His Ala Tyr Ala Asp Thr Arg Tyr Glu Asp Arg Ala Lys Gln Leu
65                  70                  75                  80

Gln Glu Glu Val Arg Lys Met Ile Lys Asp Glu Asn Ser Asp Met Trp
                85                  90                  95

Leu Lys Leu Glu Leu Ile Asn Asp Val Lys Arg Leu Gly Leu Ser Tyr
            100                 105                 110

His Tyr Asp Lys Glu Ile Gly Glu Ala Leu Leu Arg Phe His Ser Ser
        115                 120                 125

Ala Thr Phe Ser Gly Thr Ile Val His Arg Ser Leu His Glu Thr Ala
    130                 135                 140

Leu Cys Phe Arg Leu Leu Arg Glu Tyr Gly Tyr Asp Val Thr Ala Asp
145                 150                 155                 160

Met Phe Glu Arg Phe Lys Glu Arg Asn Gly His Phe Lys Ala Ser Leu
                165                 170                 175

Met Ser Asp Val Lys Gly Met Leu Ser Leu Tyr Gln Ala Ser Phe Leu
            180                 185                 190

Gly Tyr Glu Gly Glu Gln Ile Leu Asp Asp Ala Lys Ala Phe Ser Ser
        195                 200                 205

Phe His Leu Lys Ser Val Leu Ser Glu Gly Arg Asn Asn Met Val Leu
    210                 215                 220

Glu Glu Val Asn His Ala Leu Glu Leu Pro Leu His His Arg Ile Gln
225                 230                 235                 240

Arg Leu Glu Ala Arg Trp Tyr Ile Glu Tyr Tyr Ala Lys Gln Arg Asp
                245                 250                 255

Ser Asn Arg Val Leu Leu Glu Ala Ala Lys Leu Asp Phe Asn Ile Leu
            260                 265                 270

Gln Ser Thr Leu Gln Asn Asp Leu Gln Glu Val Ser Arg Trp Trp Lys
        275                 280                 285

Gly Met Gly Leu Ala Ser Lys Leu Ser Phe Ser Arg Asp Arg Leu Met
    290                 295                 300

Glu Cys Phe Phe Trp Ala Ala Gly Met Val Phe Glu Pro Gln Phe Ser
305                 310                 315                 320

Asp Leu Arg Lys Gly Leu Thr Lys Val Ala Ser Leu Ile Thr Thr Ile
                325                 330                 335

Asp Asp Val Tyr Asp Val Tyr Gly Thr Leu Glu Glu Leu Glu Leu Phe
            340                 345                 350

Thr Ala Ala Val Glu Ser Trp Asp Val Lys Ala Ile Gln Val Leu Pro
        355                 360                 365

Asp Tyr Met Lys Ile Cys Phe Leu Ala Leu Tyr Asn Thr Val Asn Glu
    370                 375                 380

```
Phe Ala Tyr Asp Ala Leu Lys Glu Gln Gly Gln Asp Ile Leu Pro Tyr
385                 390                 395                 400

Leu Thr Lys Ala Trp Ser Asp Leu Leu Lys Ala Phe Leu Gln Glu Ala
                405                 410                 415

Lys Trp Ser Arg Asp Arg His Met Pro Arg Phe Asn Asp Tyr Leu Asn
            420                 425                 430

Asn Ala Trp Val Ser Val Ser Gly Val Val Leu Leu Thr His Ala Tyr
            435                 440                 445

Phe Leu Leu Asn His Ser Ile Thr Glu Glu Ala Leu Glu Ser Leu Asp
450                 455                 460

Ser Tyr His Ser Leu Leu Gln Asn Thr Ser Leu Val Phe Arg Leu Cys
465                 470                 475                 480

Asn Asp Leu Gly Thr Ser Lys Ala Glu Leu Glu Arg Gly Glu Ala Ala
                485                 490                 495

Ser Ser Ile Leu Cys Tyr Arg Arg Glu Ser Gly Ala Ser Glu Glu Gly
                500                 505                 510

Ala Tyr Lys His Ile Tyr Ser Leu Leu Asn Glu Thr Trp Lys Lys Met
            515                 520                 525

Asn Glu Asp Arg Val Ser Gln Ser Pro Phe Pro Lys Ala Phe Val Glu
530                 535                 540

Thr Ala Met Asn Leu Ala Arg Ile Ser His Cys Thr Tyr Gln Tyr Gly
545                 550                 555                 560

Asp Gly His Gly Ala Pro Asp Ser Thr Ala Lys Asn Arg Ile Arg Ser
                565                 570                 575

Leu Ile Ile Glu Pro Ile Ala Leu Tyr Glu Thr Glu Ile Ser Thr Ser
            580                 585                 590

Tyr

<210> SEQ ID NO 11
<211> LENGTH: 583
<212> TYPE: PRT
<213> ORGANISM: Melaleuca alternifolia

<400> SEQUENCE: 11

Met Ala Leu Arg Leu Leu Ser Thr Pro His Leu Pro Gln Leu Cys Ser
1               5                   10                  15

Arg Arg Val Ser Gly Arg Val His Cys Ser Ala Ser Thr Gln Val Ser
            20                  25                  30

Asp Ala Gln Gly Gly Arg Arg Ser Ala Asn Tyr Gln Pro Ser Val Trp
        35                  40                  45

Thr Tyr Asn Tyr Leu Gln Ser Leu Val Ala Asp Asp Ile Arg Arg Ser
50                  55                  60

Arg Arg Glu Val Glu Gln Glu Arg Glu Lys Ala Gln Ile Leu Glu Glu
65                  70                  75                  80

Asp Val Arg Gly Ala Leu Asn Asp Gly Asn Ala Glu Pro Met Ala Ile
                85                  90                  95

Phe Ala Leu Val Asp Asp Ile Gln Arg Leu Gly Leu Gly Arg Tyr Phe
            100                 105                 110

Glu Glu Asp Ile Ser Lys Ala Leu Arg Arg Cys Leu Ser Gln Tyr Ala
        115                 120                 125

Val Thr Gly Ser Leu Gln Lys Ser Leu His Thr Ala Leu Ser Phe
130                 135                 140

Arg Val Leu Arg Gln His Gly Phe Glu Val Ser Gln Asp Val Phe Lys
145                 150                 155                 160
```

```
Ile Phe Met Asp Glu Ser Gly Ser Phe Met Lys Thr Leu Gly Gly Asp
            165                 170                 175

Val Gln Gly Met Leu Ser Leu Tyr Glu Ala Ser His Leu Ala Phe Glu
        180                 185                 190

Glu Glu Asp Ile Leu His Lys Ala Lys Thr Phe Ala Ile Lys His Leu
    195                 200                 205

Glu Asn Leu Asn His Asp Ile Asp Gln Asp Leu Gln Asp His Val Asn
210                 215                 220

His Glu Leu Glu Leu Pro Leu His Arg Arg Met Pro Leu Leu Glu Ala
225                 230                 235                 240

Arg Arg Phe Ile Glu Ala Tyr Ser Arg Ser Asn Val Asn Pro Arg
                245                 250                 255

Ile Leu Glu Leu Ala Val Met Lys Phe Asn Ser Ser Gln Leu Thr Leu
            260                 265                 270

Gln Arg Asp Leu Gln Asp Met Leu Gly Trp Trp Asn Asn Val Gly Leu
        275                 280                 285

Ala Lys Arg Leu Ser Phe Ala Arg Asp Arg Leu Met Glu Cys Phe Phe
    290                 295                 300

Trp Ala Val Gly Ile Ala Arg Glu Pro Ala Leu Ser Asn Cys Arg Lys
305                 310                 315                 320

Gly Val Thr Lys Ala Phe Ser Leu Ile Leu Val Leu Asp Asp Val Tyr
                325                 330                 335

Asp Val Phe Gly Thr Leu Asp Glu Leu Glu Leu Phe Thr Asp Ala Val
            340                 345                 350

Arg Arg Trp His Glu Asp Ala Val Glu Asn Leu Pro Gly Tyr Met Lys
        355                 360                 365

Leu Cys Phe Leu Ala Leu Tyr Asn Ser Val Asn Asp Met Ala Tyr Glu
    370                 375                 380

Thr Leu Lys Glu Thr Gly Glu Asn Val Thr Pro Tyr Leu Thr Lys Val
385                 390                 395                 400

Trp Tyr Asp Leu Cys Lys Ala Phe Leu Gln Glu Ala Lys Trp Ser Tyr
                405                 410                 415

Asn Lys Ile Thr Pro Gly Val Glu Glu Tyr Leu Asn Asn Gly Trp Val
            420                 425                 430

Ser Ser Ser Gly Gln Val Met Leu Thr His Ala Tyr Phe Leu Ser Ser
        435                 440                 445

Pro Ser Leu Arg Lys Glu Glu Leu Glu Ser Leu Glu His Tyr His Asp
    450                 455                 460

Leu Leu Arg Leu Pro Ser Leu Ile Phe Arg Leu Thr Asn Asp Leu Ala
465                 470                 475                 480

Thr Ser Ser Ala Glu Leu Gly Arg Gly Glu Thr Thr Asn Ser Ile Leu
                485                 490                 495

Cys Tyr Met Arg Glu Lys Gly Phe Ser Glu Ser Glu Ala Arg Lys Gln
            500                 505                 510

Val Ile Glu Gln Ile Asp Thr Ala Trp Arg Gln Met Asn Lys Tyr Met
        515                 520                 525

Val Asp His Ser Thr Phe Asn Arg Ser Phe Met Gln Met Thr Tyr Asn
    530                 535                 540

Leu Ala Arg Met Ala His Cys Val Tyr Gln Asp Gly Asp Ala Ile Gly
545                 550                 555                 560

Ala Pro Asp Asp Gln Ser Trp Asn Arg Val His Ser Leu Ile Ile Lys
                565                 570                 575
```

```
Pro Val Ser Leu Ala Pro Cys
        580
```

<210> SEQ ID NO 12
<211> LENGTH: 601
<212> TYPE: PRT
<213> ORGANISM: Vitis vinifera

<400> SEQUENCE: 12

```
Met Ala Leu His Leu Phe Tyr Phe Pro Lys Gln Cys Phe Leu Thr His
1               5                   10                  15

Asn Leu Pro Gly His Pro Met Lys Lys Pro Pro Arg Gly Thr Thr Ala
            20                  25                  30

Gln Ile Arg Cys Ser Ala Asn Glu Gln Ser Phe Ser Leu Met Thr Glu
        35                  40                  45

Ser Arg Ser Ala His Tyr Gln Pro Ala Phe Trp Ser Tyr Asp Phe
    50                  55                  60

Val Glu Ser Leu Lys Lys Arg Glu Glu Ile Cys Asp Gly Ser Val Lys
65                  70                  75                  80

Glu Leu Glu Lys Met Tyr Glu Asp Arg Ala Arg Lys Leu Glu Asp Glu
                85                  90                  95

Val Lys Trp Met Ile His Glu Lys Ser Ala Glu Pro Leu Thr Leu Leu
            100                 105                 110

Glu Phe Ile Asp Asp Ile Gln Arg Leu Gly Leu Gly His Arg Phe Glu
        115                 120                 125

Asn Asp Ile Lys Arg Ser Leu Asp Lys Ile Leu Leu Leu Glu Gly Ser
    130                 135                 140

Asn Ala Gly Lys Gly Glu Ser Leu His His Thr Ala Leu Arg Phe Arg
145                 150                 155                 160

Ile Leu Lys Gln His Gly Tyr Lys Val Ser Gln Glu Val Phe Glu Gly
                165                 170                 175

Phe Thr Asp Gln Asn Gly His Phe Lys Ala Cys Leu Cys Lys Asp Val
            180                 185                 190

Lys Gly Met Leu Ser Leu Tyr Glu Ala Ser Tyr Leu Ala Ser Glu Gly
        195                 200                 205

Glu Thr Leu Leu His Glu Ala Met Ala Phe Leu Lys Met His Leu Lys
    210                 215                 220

Asp Leu Glu Gly Thr Leu Asp Lys Ser Leu Glu Glu Leu Val Asn His
225                 230                 235                 240

Ala Met Glu Leu Pro Leu His Arg Arg Met Pro Arg Leu Glu Ala Arg
                245                 250                 255

Trp Phe Ile Glu Ala Tyr Lys Arg Arg Glu Gly Ala Asp Asp Val Leu
            260                 265                 270

Leu Glu Leu Ala Ile Leu Asp Phe Asn Met Val Gln Trp Thr Leu Gln
        275                 280                 285

Asp Asp Leu Gln Asp Met Ser Arg Trp Trp Lys Asp Met Gly Leu Ala
    290                 295                 300

Ser Lys Leu His Phe Ala Arg Asp Arg Leu Met Glu Cys Phe Phe Trp
305                 310                 315                 320

Thr Val Gly Met Ala Phe Glu Pro Glu Phe Ser Asn Cys Arg Lys Gly
                325                 330                 335

Leu Thr Lys Val Thr Ser Phe Ile Thr Thr Ile Asp Asp Val Tyr Asp
            340                 345                 350

Val Tyr Gly Ser Val Asp Glu Leu Glu Leu Phe Thr Asp Ala Val Ala
        355                 360                 365
```

```
Arg Trp Asp Ile Asn Met Val Asn Asn Leu Pro Gly Tyr Met Lys Leu
    370                 375                 380

Cys Phe Leu Ala Leu Tyr Asn Thr Val Asn Glu Met Ala Tyr Asp Thr
385                 390                 395                 400

Leu Lys Glu Gln Gly His Asn Ile Leu Pro Tyr Leu Thr Lys Ala Trp
                405                 410                 415

Ala Asp Leu Cys Lys Val Phe Leu Val Glu Ala Lys Trp Cys His Lys
                420                 425                 430

Glu Tyr Thr Pro Thr Phe Glu Glu Tyr Leu Glu Asn Gly Trp Arg Ser
                435                 440                 445

Val Ser Gly Ala Ala Ile Leu Ile His Ala Tyr Phe Leu Met Ser Lys
    450                 455                 460

Asn Ile Thr Lys Glu Ala Leu Glu Cys Leu Glu Asn Asp His Glu Leu
465                 470                 475                 480

Leu Arg Trp Pro Ser Thr Ile Phe Arg Leu Cys Asn Asp Leu Ala Thr
                485                 490                 495

Ser Lys Ala Glu Leu Glu Arg Gly Glu Ser Ala Asn Ser Ile Ser Cys
                500                 505                 510

Tyr Met His Gln Thr Gly Val Ser Glu Glu Asp Ala Arg Glu His Met
                515                 520                 525

Lys Ile Leu Ile Asp Glu Ser Trp Lys Lys Met Asn Lys Val Arg Glu
    530                 535                 540

Met Asp Ser Asp Ser Pro Phe Ala Lys Pro Phe Val Glu Thr Ala Ile
545                 550                 555                 560

Asn Leu Ala Arg Ile Ala Gln Cys Thr Tyr Gln Tyr Gly Asp Ser His
                565                 570                 575

Gly Ala Pro Asp Ala Arg Ser Lys Arg Val Leu Ser Leu Ile Val
                580                 585                 590

Glu Pro Ile Pro Met Asn Leu Lys Lys
    595                 600

<210> SEQ ID NO 13
<211> LENGTH: 661
<212> TYPE: PRT
<213> ORGANISM: Marinobacter aquaeolei VT8

<400> SEQUENCE: 13

Met Asn Tyr Phe Leu Thr Gly Gly Thr Gly Phe Ile Gly Arg Phe Leu
1               5                   10                  15

Val Glu Lys Leu Leu Ala Arg Gly Gly Thr Val Tyr Val Leu Val Arg
                20                  25                  30

Glu Gln Ser Gln Asp Lys Leu Glu Arg Leu Arg Glu Arg Trp Gly Ala
            35                  40                  45

Asp Asp Lys Gln Val Lys Ala Val Ile Gly Asp Leu Thr Ser Lys Asn
        50                  55                  60

Leu Gly Ile Asp Ala Lys Thr Leu Lys Ser Leu Lys Gly Asn Ile Asp
65                  70                  75                  80

His Val Phe His Leu Ala Ala Val Tyr Asp Met Gly Ala Asp Glu Glu
                85                  90                  95

Ala Gln Ala Ala Thr Asn Ile Glu Gly Thr Arg Ala Ala Val Gln Ala
            100                 105                 110

Ala Glu Ala Met Gly Ala Lys His Phe His His Val Ser Ser Ile Ala
        115                 120                 125
```

```
Ala Ala Gly Leu Phe Lys Gly Ile Phe Arg Glu Asp Met Phe Glu Glu
130                 135                 140
Ala Glu Lys Leu Asp His Pro Tyr Leu Arg Thr Lys His Glu Ser Glu
145                 150                 155                 160
Lys Val Val Arg Glu Glu Cys Lys Val Pro Phe Arg Ile Tyr Arg Pro
            165                 170                 175
Gly Met Val Ile Gly His Ser Glu Thr Gly Glu Met Asp Lys Val Asp
            180                 185                 190
Gly Pro Tyr Tyr Phe Phe Lys Met Ile Gln Lys Ile Arg His Ala Leu
            195                 200                 205
Pro Gln Trp Val Pro Thr Ile Gly Ile Glu Gly Gly Arg Leu Asn Ile
210                 215                 220
Val Pro Val Asp Phe Val Val Asp Ala Leu Asp His Ile Ala His Leu
225                 230                 235                 240
Glu Gly Glu Asp Gly Asn Cys Phe His Leu Val Asp Ser Asp Pro Tyr
                245                 250                 255
Lys Val Gly Glu Ile Leu Asn Ile Phe Cys Glu Ala Gly His Ala Pro
            260                 265                 270
Arg Met Gly Met Arg Ile Asp Ser Arg Met Phe Gly Phe Ile Pro Pro
            275                 280                 285
Phe Ile Arg Gln Ser Ile Lys Asn Leu Pro Pro Val Lys Arg Ile Thr
290                 295                 300
Gly Ala Leu Leu Asp Asp Met Gly Ile Pro Pro Ser Val Met Ser Phe
305                 310                 315                 320
Ile Asn Tyr Pro Thr Arg Phe Asp Thr Arg Glu Leu Glu Arg Val Leu
                325                 330                 335
Lys Gly Thr Asp Ile Glu Val Pro Arg Leu Pro Ser Tyr Ala Pro Val
            340                 345                 350
Ile Trp Asp Tyr Trp Glu Arg Asn Leu Asp Pro Asp Leu Phe Lys Asp
            355                 360                 365
Arg Thr Leu Lys Gly Thr Val Glu Gly Lys Val Cys Val Val Thr Gly
370                 375                 380
Ala Thr Ser Gly Ile Gly Leu Ala Thr Ala Glu Lys Leu Ala Glu Ala
385                 390                 395                 400
Gly Ala Ile Leu Val Ile Gly Ala Arg Thr Lys Glu Thr Leu Asp Glu
                405                 410                 415
Val Ala Ala Ser Leu Glu Ala Lys Gly Gly Asn Val His Ala Tyr Gln
            420                 425                 430
Cys Asp Phe Ser Asp Met Asp Asp Cys Asp Arg Phe Val Lys Thr Val
            435                 440                 445
Leu Asp Asn His Gly His Val Asp Val Leu Val Asn Asn Ala Gly Arg
450                 455                 460
Ser Ile Arg Arg Ser Leu Ala Leu Ser Phe Asp Arg Phe His Asp Phe
465                 470                 475                 480
Glu Arg Thr Met Gln Leu Asn Tyr Phe Gly Ser Val Arg Leu Ile Met
                485                 490                 495
Gly Phe Ala Pro Ala Met Leu Glu Arg Arg Gly His Val Val Asn
            500                 505                 510
Ile Ser Ser Ile Gly Val Leu Thr Asn Ala Pro Arg Phe Ser Ala Tyr
            515                 520                 525
Val Ser Ser Lys Ser Ala Leu Asp Ala Phe Ser Arg Cys Ala Ala Ala
530                 535                 540
```

```
Glu Trp Ser Asp Arg Asn Val Thr Phe Thr Thr Ile Asn Met Pro Leu
545                 550                 555                 560

Val Lys Thr Pro Met Ile Ala Pro Thr Lys Ile Tyr Asp Ser Val Pro
                565                 570                 575

Thr Leu Thr Pro Asp Glu Ala Ala Gln Met Val Ala Asp Ala Ile Val
            580                 585                 590

Tyr Arg Pro Lys Arg Ile Ala Thr Arg Leu Gly Val Phe Ala Gln Val
        595                 600                 605

Leu His Ala Leu Ala Pro Lys Met Gly Glu Ile Ile Met Asn Thr Gly
    610                 615                 620

Tyr Arg Met Phe Pro Asp Ser Pro Ala Ala Gly Ser Lys Ser Gly
625                 630                 635                 640

Glu Lys Pro Lys Val Ser Thr Glu Gln Val Ala Phe Ala Ala Ile Met
                645                 650                 655

Arg Gly Ile Tyr Trp
            660

<210> SEQ ID NO 14
<211> LENGTH: 540
<212> TYPE: PRT
<213> ORGANISM: Marinobacter manganoxydans

<400> SEQUENCE: 14

Met Asn Tyr Phe Leu Thr Gly Gly Thr Gly Phe Ile Gly Arg Phe Leu
1               5                   10                  15

Val Glu Lys Leu Leu Ala Arg Gly Gly Thr Val His Val Leu Val Arg
            20                  25                  30

Glu Gln Ser Gln Asp Lys Leu Asp Lys Leu Arg Glu Arg Trp Gly Ala
        35                  40                  45

Asp Glu Thr Gln Val Lys Ala Val Ile Gly Asp Leu Thr Ser Lys Asn
    50                  55                  60

Leu Gly Ile Asp Ala Lys Thr Met Lys Ala Leu Lys Gly Lys Ile Asp
65                  70                  75                  80

His Phe Phe His Leu Ala Ala Val Tyr Asp Met Gly Ala Asp Glu Glu
                85                  90                  95

Ala Gln Gln Ala Thr Asn Ile Glu Gly Thr Arg Ala Ala Val Asn Ala
            100                 105                 110

Ala Glu Ala Met Gly Ala Lys His Phe His His Val Ser Ser Ile Ala
        115                 120                 125

Ala Ala Gly Leu Phe Lys Gly Ile Phe Arg Glu Asp Met Phe Glu Glu
    130                 135                 140

Ala Glu Lys Leu Asp His Pro Tyr Leu Arg Thr Lys His Glu Ser Glu
145                 150                 155                 160

Lys Val Val Arg Glu Glu Cys Lys Val Pro Phe Arg Ile Tyr Arg Pro
                165                 170                 175

Gly Met Val Ile Gly His Thr Ala Thr Gly Glu Met Asp Lys Val Asp
            180                 185                 190

Gly Pro Tyr Tyr Phe Phe Lys Met Ile Gln Lys Ile Arg His Ala Leu
        195                 200                 205

Pro Gln Trp Val Pro Thr Ile Gly Val Glu Gly Gly Arg Leu Asn Ile
    210                 215                 220

Val Pro Val Asp Phe Val Val Asn Ala Met Asp His Ile Ala His Leu
225                 230                 235                 240

Glu Gly Glu Asp Gly Lys Cys Phe His Leu Val Asp Thr Asp Pro Tyr
                245                 250                 255
```

```
Lys Val Gly Glu Ile Leu Asn Ile Phe Ser Glu Ala Gly His Ala Pro
            260                 265                 270

Arg Met Gly Met Arg Ile Asp Ser Arg Met Phe Gly Phe Ile Pro Pro
            275                 280                 285

Phe Ile Arg Gln Ser Leu Lys Asn Leu Pro Pro Val Lys Arg Leu Thr
290                 295                 300

Ser Ala Ile Leu Asp Asp Met Gly Ile Pro Ser Val Met Ser Phe
305                 310                 315                 320

Ile Asn Tyr Pro Thr Arg Phe Asp Ala Arg Glu Thr Glu Arg Val Leu
            325                 330                 335

Lys Gly Thr Gly Ile Glu Val Pro Arg Leu Pro Asp Tyr Ala Pro Val
            340                 345                 350

Ile Trp Asp Tyr Trp Glu Arg Asn Leu Asp Pro Asp Leu Phe Lys Asp
            355                 360                 365

Arg Thr Leu Lys Gly Thr Val Glu Gly Arg Val Cys Val Val Thr Gly
        370                 375                 380

Ala Thr Ser Gly Ile Gly Leu Ala Thr Ala Gln Lys Leu Ala Asp Ala
385                 390                 395                 400

Gly Ala Ile Leu Val Ile Gly Ala Arg Lys Leu Glu Arg Leu Lys Glu
            405                 410                 415

Val Ala Ala Glu Leu Glu Ser Arg Gly Ala Ser Val His Ala Tyr Pro
            420                 425                 430

Cys Asp Phe Ser Asp Met Asp Ala Cys Asp Glu Phe Val Lys Thr Val
            435                 440                 445

Leu Asp Asn His Gly Gln Val Asp Val Leu Val Asn Asn Ala Gly Arg
450                 455                 460

Ser Ile Arg Arg Ser Leu Asp Leu Ser Phe Asp Arg Phe His Asp Phe
465                 470                 475                 480

Glu Arg Thr Met Gln Leu Asn Tyr Phe Gly Ser Val Arg Leu Ile Met
            485                 490                 495

Gly Phe Ala Pro Lys Met Leu Glu Asn Arg Arg Gly His Val Val Asn
            500                 505                 510

Ile Ser Ser Ile Gly Val Leu Thr Asn Ala Pro Arg Phe Ser Ala Tyr
            515                 520                 525

Val Ala Ser Lys Ser Ala Leu Asp Ala Phe Ser Arg
            530                 535                 540

<210> SEQ ID NO 15
<211> LENGTH: 661
<212> TYPE: PRT
<213> ORGANISM: Marinobacter sp. ELB17

<400> SEQUENCE: 15

Met Asn Tyr Phe Val Thr Gly Gly Thr Gly Phe Ile Gly Arg Phe Leu
1               5                   10                  15

Ile Ala Arg Leu Leu Ala Arg Gly Ala Ile Val His Val Leu Val Arg
            20                  25                  30

Glu Gln Ser Val Gln Lys Leu Ala Asp Leu Arg Glu Lys Leu Gly Ala
        35                  40                  45

Asp Glu Lys Gln Ile Lys Ala Val Val Gly Asp Leu Thr Ala Pro Gly
    50                  55                  60

Leu Gly Leu Asp Lys Lys Thr Leu Lys Gln Leu Ser Gly Lys Ile Asp
65                  70                  75                  80
```

```
His Phe Phe His Leu Ala Ala Ile Tyr Asp Met Ser Ala Ser Glu Glu
                 85                  90                  95

Ser Gln Gln Ala Ala Asn Ile Asp Gly Thr Arg Ala Ala Val Ala Ala
            100                 105                 110

Ala Glu Ala Leu Gly Ala Gly Ile Phe His His Val Ser Ser Ile Ala
        115                 120                 125

Val Ala Gly Leu Phe Lys Gly Thr Phe Arg Glu Asp Met Phe Ala Glu
130                 135                 140

Ala Gly Lys Leu Asp His Pro Tyr Phe Ser Thr Lys His Glu Ser Glu
145                 150                 155                 160

Arg Val Val Arg Asp Glu Cys Lys Leu Pro Phe Arg Ile Tyr Arg Pro
                165                 170                 175

Gly Met Val Ile Gly Asp Ser Ala Thr Gly Glu Met Asp Lys Val Asp
                180                 185                 190

Gly Pro Tyr Tyr Phe Phe Lys Met Ile Gln Lys Ile Arg Gly Ala Leu
            195                 200                 205

Pro Gln Trp Val Pro Thr Ile Gly Leu Glu Gly Gly Arg Leu Asn Ile
        210                 215                 220

Val Pro Val Asn Phe Val Ala Asp Ala Leu Asp His Ile Ala His Leu
225                 230                 235                 240

Pro Asp Glu Asp Gly Lys Cys Phe His Leu Val Asp Ser Asp Pro Tyr
                245                 250                 255

Lys Val Gly Glu Ile Leu Asn Ile Phe Cys Glu Ala Gly His Ala Pro
                260                 265                 270

Lys Met Gly Met Arg Ile Asp Ser Arg Met Phe Gly Phe Val Pro Pro
            275                 280                 285

Phe Ile Arg Gln Ser Leu Lys Asn Leu Pro Pro Val Lys Arg Met Gly
        290                 295                 300

Arg Ala Leu Leu Asp Asp Leu Gly Ile Pro Ala Ser Val Leu Ser Phe
305                 310                 315                 320

Ile Asn Tyr Pro Thr Arg Phe Asp Ala Arg Glu Thr Glu Arg Val Leu
                325                 330                 335

Gln Gly Thr Gly Ile Glu Val Pro Arg Leu Pro Asp Tyr Ala Pro Val
            340                 345                 350

Ile Trp Asp Tyr Trp Glu Arg Asn Leu Asp Pro Asp Leu Phe Thr Asp
        355                 360                 365

Arg Thr Leu Arg Gly Thr Val Glu Gly Lys Val Cys Val Val Thr Gly
370                 375                 380

Ala Thr Ser Gly Ile Gly Leu Ala Thr Ala Glu Lys Leu Ala Asp Ala
385                 390                 395                 400

Gly Ala Ile Leu Val Ile Gly Ala Arg Thr Gln Glu Thr Leu Asp Gln
                405                 410                 415

Val Ser Ala Gln Leu Asn Ala Arg Gly Ala Asp Val His Ala Tyr Gln
            420                 425                 430

Cys Asp Phe Ala Asp Met Asp Ala Cys Asp Arg Phe Ile Gln Thr Val
        435                 440                 445

Ser Glu Asn His Gly Ala Val Asp Val Leu Ile Asn Asn Ala Gly Arg
450                 455                 460

Ser Ile Arg Arg Ser Leu Asp Lys Ser Phe Asp Arg Phe His Asp Phe
465                 470                 475                 480

Glu Arg Thr Met Gln Leu Asn Tyr Phe Gly Ser Leu Arg Leu Ile Met
                485                 490                 495
```

```
Gly Phe Ala Pro Ala Met Leu Glu Arg Arg Gly His Ile Ile Asn
            500                 505                 510
Ile Ser Ser Ile Gly Val Leu Thr Asn Ala Pro Arg Phe Ser Ala Tyr
    515                 520                 525
Val Ala Ser Lys Ala Ala Leu Asp Ser Phe Ser Arg Cys Ala Ala Ala
    530                 535                 540
Glu Trp Ser Asp Arg His Val Cys Phe Thr Thr Ile Asn Met Pro Leu
545                 550                 555                 560
Val Lys Thr Pro Met Ile Ala Pro Thr Lys Ile Tyr Asp Ser Val Pro
                565                 570                 575
Thr Leu Ser Pro Glu Glu Ala Ala Asp Met Val Val Asn Ala Ile Val
            580                 585                 590
Tyr Arg Pro Lys Arg Ile Ala Thr Arg Met Gly Val Phe Ala Gln Val
        595                 600                 605
Leu Asn Ala Val Ala Pro Lys Ala Ser Glu Ile Leu Met Asn Thr Gly
    610                 615                 620
Tyr Lys Met Phe Pro Asp Ser Met Pro Lys Lys Gly Lys Glu Val Ser
625                 630                 635                 640
Ala Glu Lys Gly Ala Ser Thr Asp Gln Val Ala Phe Ala Ala Ile Met
                645                 650                 655
Arg Gly Ile His Trp
            660

<210> SEQ ID NO 16
<211> LENGTH: 661
<212> TYPE: PRT
<213> ORGANISM: Marinobacter algicola DG893

<400> SEQUENCE: 16

Met Asn Tyr Phe Leu Thr Gly Gly Thr Gly Phe Ile Gly Arg Phe Leu
1               5                   10                  15
Val Glu Lys Leu Leu Ala Arg Gly Gly Thr Val His Val Leu Val Arg
            20                  25                  30
Glu Gln Ser Gln Glu Lys Leu Asp Lys Leu Arg Glu Arg Trp Gly Ala
        35                  40                  45
Asp Glu Ser Arg Val Lys Ala Val Ile Gly Asp Leu Thr Ser Pro Asn
    50                  55                  60
Leu Gly Ile Asp Ala Lys Thr Met Lys Ser Leu Lys Gly Asn Ile Asp
65                  70                  75                  80
His Phe Phe His Leu Ala Ala Val Tyr Asp Met Gly Ala Asp Glu Lys
                85                  90                  95
Ser Gln Gln Ala Thr Asn Ile Glu Gly Thr His Ser Ala Val Asn Ala
            100                 105                 110
Ala Ala Ala Met Glu Ala Gly Cys Phe His His Val Ser Ser Ile Ala
        115                 120                 125
Ala Ala Gly Leu Phe Lys Gly Thr Phe Arg Glu Asp Met Phe Glu Glu
    130                 135                 140
Ala Glu Lys Leu Asp His Pro Tyr Leu Leu Thr Lys His Glu Ser Glu
145                 150                 155                 160
Lys Val Val Arg Glu Ser Cys Lys Val Pro Phe Arg Ile Tyr Arg Pro
                165                 170                 175
Gly Met Val Val Gly His Ser Lys Thr Gly Glu Met Asp Lys Val Asp
            180                 185                 190
Gly Pro Tyr Tyr Phe Phe Lys Met Ile Gln Lys Ile Arg His Ala Leu
        195                 200                 205
```

-continued

```
Pro Gln Trp Val Pro Thr Ile Gly Ile Glu Gly Gly Arg Leu Asn Ile
    210                 215                 220

Val Pro Val Asp Phe Val Asn Ala Met Asp His Ile Ala His Leu
225                 230                 235                 240

Lys Gly Glu Asp Gly Asn Cys Phe His Leu Val Asp Ser Asp Pro Tyr
                245                 250                 255

Lys Val Gly Glu Ile Leu Asn Ile Phe Ser Glu Ala Gly His Ala Pro
                260                 265                 270

Arg Met Ala Met Arg Ile Asp Ser Arg Met Phe Gly Phe Val Pro Pro
            275                 280                 285

Phe Ile Arg Gln Ser Leu Lys Asn Leu Pro Pro Val Lys Arg Leu Thr
    290                 295                 300

Thr Ala Leu Leu Asp Asp Met Gly Ile Pro Pro Ser Val Leu Ser Phe
305                 310                 315                 320

Ile Asn Tyr Pro Thr Arg Phe Asp Ala Arg Glu Thr Glu Arg Val Leu
                325                 330                 335

Lys Asp Thr Gly Ile Val Val Pro Arg Leu Glu Ser Tyr Ala Ala Val
                340                 345                 350

Leu Trp Asp Phe Trp Glu Arg Asn Leu Asp Pro Asp Leu Phe Lys Asp
            355                 360                 365

Arg Thr Leu Arg Gly Thr Val Glu Gly Lys Val Cys Val Ile Thr Gly
    370                 375                 380

Gly Thr Ser Gly Ile Gly Leu Ala Thr Ala Gln Lys Leu Ala Asp Ala
385                 390                 395                 400

Gly Ala Ile Leu Val Ile Gly Ala Arg Lys Lys Glu Arg Leu Met Glu
                405                 410                 415

Val Ala Ala Glu Leu Glu Ala Arg Gly Gly Asn Val His Ala Tyr Gln
                420                 425                 430

Cys Asp Phe Ala Asp Met Asp Asp Cys Asp Arg Phe Val Lys Thr Val
            435                 440                 445

Leu Asp Asn His Gly His Val Asp Val Leu Val Asn Asn Ala Gly Arg
    450                 455                 460

Ser Ile Arg Arg Ser Leu Ala Leu Ser Phe Asp Arg Phe His Asp Phe
465                 470                 475                 480

Glu Arg Thr Met Gln Leu Asn Tyr Phe Gly Ser Val Arg Leu Ile Met
                485                 490                 495

Gly Phe Ala Pro Ala Met Leu Glu Arg Arg Gly His Val Val Asn
            500                 505                 510

Ile Ser Ser Ile Gly Val Leu Thr Asn Ala Pro Arg Phe Ser Ala Tyr
    515                 520                 525

Val Ala Ser Lys Ser Ala Leu Asp Thr Phe Ser Arg Cys Ala Ala Ala
530                 535                 540

Glu Trp Ser Asp Arg Asn Val Thr Phe Thr Thr Ile Asn Met Pro Leu
545                 550                 555                 560

Val Lys Thr Pro Met Ile Ala Pro Thr Lys Ile Tyr Asp Ser Val Pro
                565                 570                 575

Thr Leu Thr Pro Asp Glu Ala Ala Glu Met Val Ala Asp Ala Ile Val
                580                 585                 590

Tyr Arg Pro Lys Arg Ile Ala Thr Arg Leu Gly Ile Phe Ala Gln Val
            595                 600                 605

Met Gln Ala Leu Ala Pro Lys Met Gly Glu Ile Val Met Asn Thr Gly
    610                 615                 620
```

Tyr Arg Met Phe Pro Asp Ser Pro Ala Ala Ala Gly Ser Arg Ser Gly
625                 630                 635                 640

Ala Lys Pro Lys Val Ser Ser Glu Gln Val Ala Phe Ala Ala Ile Met
            645                 650                 655

Arg Gly Ile Tyr Trp
            660

<210> SEQ ID NO 17
<211> LENGTH: 661
<212> TYPE: PRT
<213> ORGANISM: Hahella chejuensis

<400> SEQUENCE: 17

Met Asn Tyr Phe Val Thr Gly Gly Thr Gly Phe Ile Gly Arg Phe Leu
1               5                   10                  15

Val Pro Lys Leu Leu Lys Arg Gly Gly Thr Val Tyr Leu Leu Val Arg
            20                  25                  30

Glu Ala Ser Leu Pro Lys Leu Asp Glu Leu Arg Glu Arg Trp Asn Ala
        35                  40                  45

Ser Asp Glu Gln Val Val Gly Val Gly Asp Leu Ala Gln Pro Met
50                  55                  60

Leu Gly Val Ser Glu Lys Asp Ala Ala Met Leu Arg Gly Lys Val Gly
65                  70                  75                  80

His Phe Phe His Leu Ala Ala Ile Tyr Asp Met Gln Ala Ser Ala Glu
                85                  90                  95

Ser Gln Glu Gln Ala Asn Ile Glu Gly Thr Arg Asn Ala Val Lys Leu
            100                 105                 110

Ala Asp Ser Leu Lys Ala Ala Cys Phe His His Val Ser Ser Ile Ala
        115                 120                 125

Ala Ala Gly Leu Tyr Arg Gly Ile Phe Arg Glu Asp Met Phe Glu Glu
    130                 135                 140

Ala Glu Lys Leu Asp Asn Pro Tyr Leu Arg Thr Lys His Glu Ser Glu
145                 150                 155                 160

Lys Val Val Arg Glu Glu Cys Gln Thr Pro Trp Arg Val Tyr Arg Pro
                165                 170                 175

Gly Met Val Val Gly His Ser Lys Thr Gly Glu Ile Asp Lys Ile Asp
            180                 185                 190

Gly Pro Tyr Tyr Phe Phe Lys Leu Ile Gln Lys Leu Arg Ser Ala Leu
        195                 200                 205

Pro Gln Trp Met Pro Thr Val Gly Leu Glu Gly Gly Arg Ile Asn Ile
    210                 215                 220

Val Pro Val Asp Phe Val Val Asp Ala Met Asp His Ile Ala His Ala
225                 230                 235                 240

Glu Gly Glu Asp Gly Lys Cys Phe His Leu Thr Asp Pro Asp Pro Tyr
                245                 250                 255

Lys Val Gly Glu Ile Leu Asn Ile Phe Ala Glu Ala Gly His Ala Pro
            260                 265                 270

Lys Met Ala Met Arg Ile Asp Ala Arg Met Phe Gly Phe Ile Pro Pro
        275                 280                 285

Met Ile Arg Gln Gly Ile Ala Arg Leu Pro Val Gln Arg Met Lys
    290                 295                 300

Asn Ala Val Leu Asn Asp Leu Gly Ile Pro Asp Glu Val Met Ser Phe
305                 310                 315                 320

Ile Asn Tyr Pro Thr Arg Phe Asp Asn Arg Glu Thr Glu Arg Leu Leu
                325                 330                 335

Lys Gly Thr Ala Ile Ala Val Pro Arg Leu Gln Asp Tyr Ser Pro Ala
            340                 345                 350

Ile Trp Asp Tyr Trp Glu Arg His Leu Asp Pro Asp Leu His Lys Asp
            355                 360                 365

Arg Thr Leu Arg Gly Ala Val Glu Gly Arg Val Cys Val Ile Thr Gly
370                 375                 380

Ala Thr Ser Gly Ile Gly Leu Ser Ala Ala Arg Lys Leu Ala Glu Ala
385                 390                 395                 400

Gly Ala Lys Val Val Ile Ala Ala Arg Thr Leu Glu Lys Leu Gln Glu
                405                 410                 415

Val Lys Lys Glu Leu Glu Glu Leu Gly Gly Glu Val Tyr Glu Tyr Ser
            420                 425                 430

Val Asp Leu Ser Asp Leu Glu Asp Cys Asp Arg Phe Val Ala Asn Val
            435                 440                 445

Leu Lys Asp Leu Gly His Val Asp Val Leu Val Asn Asn Ala Gly Arg
450                 455                 460

Ser Ile Arg Arg Ser Ile Gln His Ala Phe Asp Arg Phe His Asp Phe
465                 470                 475                 480

Glu Arg Thr Met Gln Leu Asn Tyr Phe Gly Ser Leu Arg Leu Ile Met
                485                 490                 495

Gly Phe Ala Pro Ser Met Leu Glu Arg Arg Gly His Ile Val Asn
            500                 505                 510

Ile Ser Ser Ile Gly Val Leu Thr Asn Ala Pro Arg Phe Ser Ala Tyr
            515                 520                 525

Val Ala Ser Lys Ala Ala Leu Asp Ala Phe Ser Arg Cys Ala Ala Ala
            530                 535                 540

Glu Phe Ser Asp Lys Asn Val Thr Phe Thr Thr Ile Asn Met Pro Leu
545                 550                 555                 560

Val Arg Thr Pro Met Ile Ser Pro Thr Lys Ile Tyr Asp Ser Val Pro
                565                 570                 575

Thr Leu Thr Pro Glu Glu Ala Ala Asp Leu Val Ala Glu Ala Ile Ile
            580                 585                 590

His Arg Pro Lys Arg Ile Ala Thr Arg Leu Gly Val Phe Ala Gln Val
            595                 600                 605

Leu His Ser Met Ala Pro Lys Phe Ser Glu Ile Met Asn Thr Gly
            610                 615                 620

Phe Lys Met Phe Pro Asp Ser Ser Ala Ala Thr Gly Gly Lys Asp Gly
625                 630                 635                 640

Glu Lys Pro Lys Val Ser Thr Glu Gln Val Ala Phe Ala Ala Ile Met
                645                 650                 655

Arg Gly Ile His Trp
            660

<210> SEQ ID NO 18
<211> LENGTH: 6
<212> TYPE: PRT
<213> ORGANISM: Unknown
<220> FEATURE:
<223> OTHER INFORMATION: NAD(P)(H)-binding motif conserved region found
      in multiple species

<400> SEQUENCE: 18

Gly Thr Gly Phe Ile Gly
1               5

```
<210> SEQ ID NO 19
<211> LENGTH: 5
<212> TYPE: PRT
<213> ORGANISM: Unknown
<220> FEATURE:
<223> OTHER INFORMATION: Terpene synthase highly conserved C-terminal
      domain found in multiple species
<220> FEATURE:
<221> NAME/KEY: MOD_RES
<222> LOCATION: (3)..(4)
<223> OTHER INFORMATION: Xaa can be any amino acid

<400> SEQUENCE: 19

Asp Asp Xaa Xaa Asp
1               5

<210> SEQ ID NO 20
<211> LENGTH: 7
<212> TYPE: PRT
<213> ORGANISM: Unknown
<220> FEATURE:
<223> OTHER INFORMATION: NAD(P)(H)-binding motif conserved region found
      in multiple species
<220> FEATURE:
<221> NAME/KEY: MOD_RES
<222> LOCATION: (2)
<223> OTHER INFORMATION: Xaa can be any amino acid
<220> FEATURE:
<221> NAME/KEY: MOD_RES
<222> LOCATION: (4)..(5)
<223> OTHER INFORMATION: Xaa can be any amino acid
<220> FEATURE:
<221> NAME/KEY: MOD_RES
<222> LOCATION: (6)
<223> OTHER INFORMATION: Xaa can be des-Xaa or any amino acid

<400> SEQUENCE: 20

Gly Xaa Gly Xaa Xaa Xaa Gly
1               5

<210> SEQ ID NO 21
<211> LENGTH: 7
<212> TYPE: PRT
<213> ORGANISM: Unknown
<220> FEATURE:
<223> OTHER INFORMATION: NAD(P)(H)-binding motif conserved region found
      in multiple species
<220> FEATURE:
<221> NAME/KEY: MOD_RES
<222> LOCATION: (2)..(4)
<223> OTHER INFORMATION: Xaa can be any amino acid
<220> FEATURE:
<221> NAME/KEY: MOD_RES
<222> LOCATION: (6)
<223> OTHER INFORMATION: Xaa can be any amino acid

<400> SEQUENCE: 21

Gly Xaa Xaa Xaa Gly Xaa Gly
1               5
```